(12) United States Patent
Shasky et al.

(10) Patent No.: US 9,970,015 B2
(45) Date of Patent: *May 15, 2018

(54) *ASPERGILLUS FUMIGATUS* CELLULOLYTIC ENZYME COMPOSITIONS AND USES THEREOF

(71) Applicant: Novozymes, Inc., Davis, CA (US)

(72) Inventors: Jeffrey Shasky, Davis, CA (US); Brett McBrayer, Sacramento, CA (US)

(73) Assignee: Novozymes, Inc., Davis, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/489,035

(22) Filed: Apr. 17, 2017

(65) Prior Publication Data

US 2017/0218377 A1 Aug. 3, 2017

Related U.S. Application Data

(62) Division of application No. 14/238,688, filed as application No. PCT/US2012/052161 on Aug. 23, 2012, now Pat. No. 9,663,772.

(60) Provisional application No. 61/526,805, filed on Aug. 24, 2011.

(51) Int. Cl.
| *C12N 9/00* | (2006.01) |
| *C12N 9/24* | (2006.01) |
| *C12N 9/42* | (2006.01) |
| *C12P 7/00* | (2006.01) |
| *C12N 15/52* | (2006.01) |
| *C12N 15/80* | (2006.01) |
| *C12N 9/38* | (2006.01) |
| *C12N 1/14* | (2006.01) |
| *C12P 9/00* | (2006.01) |

(52) U.S. Cl.
CPC ............... *C12N 15/52* (2013.01); *C12N 1/14* (2013.01); *C12N 9/2437* (2013.01); *C12N 9/2471* (2013.01); *C12N 15/80* (2013.01); *C12P 9/00* (2013.01); *C12P 2203/00* (2013.01)

(58) Field of Classification Search
None
See application file for complete search history.

(56) References Cited

U.S. PATENT DOCUMENTS

| 8,580,536 | B2 | 11/2013 | McBrayer et al. | |
| 9,175,277 | B2 * | 11/2015 | McBrayer | C12N 1/22 |
| 9,476,036 | B2 * | 10/2016 | Shasky | C12N 9/2437 |
| 9,587,262 | B2 * | 3/2017 | McBrayer | C12N 1/22 |
| 2010/0124769 | A1 | 5/2010 | Brown et al. | |

FOREIGN PATENT DOCUMENTS

| WO | 2005047499 A1 | 5/2005 |
| WO | 2006078256 A2 | 7/2006 |
| WO | 2010138754 A1 | 12/2010 |
| WO | 2011050037 A1 | 4/2011 |
| WO | 2011057140 A1 | 5/2011 |
| WO | 2011059740 A1 | 5/2011 |
| WO | 2012061517 A1 | 5/2012 |
| WO | 2012103322 A1 | 8/2012 |

OTHER PUBLICATIONS

Nierman et al, 2005, Nature 438, 1151-1156.
Fedorova et al, 2008—Uniport Access No. BOYBXO.
Nierman et al, 2008, NCBI Accession No. XP_748511.1.
Nierman et al, 2008, NCBI Accession No. XP_001258843.1.

* cited by examiner

*Primary Examiner* — Yong D Pak
(74) *Attorney, Agent, or Firm* — Robert Starnes

(57) ABSTRACT

The present invention relates to recombinant *Trichoderma* host cells producing *Aspergillus fumigatus* cellulolytic enzyme compositions and methods of producing and using the compositions.

17 Claims, 8 Drawing Sheets

ASPERGILLUS FUMIGATUS CELLULOLYTIC ENZYME COMPOSITIONS AND USES THEREOF

CROSS-REFERENCE TO RELATED APPLICATIONS

This application is a divisional application of U.S. application Ser. No. 14/238,688 filed Feb. 12, 2014, now U.S. Pat. No. 9,663,772, which is a 35 U.S.C. § 371 national application of PCT/US2012/052161 filed Aug. 23, 2012, which claims priority or the benefit under 35 U.S.C. § 119 of U.S. Provisional Application No. 61/526,805 filed on Aug. 24, 2011, the contents of which are fully incorporated herein by reference.

STATEMENT AS TO RIGHTS TO INVENTIONS MADE UNDER FEDERALLY SPONSORED RESEARCH AND DEVELOPMENT

This invention was made with Government support under Cooperative Agreement DE-FC36-08GO18080 awarded by the Department of Energy. The government has certain rights in this invention.

REFERENCE TO A SEQUENCE LISTING

This application contains a Sequence Listing in computer readable form, which is incorporated herein by reference.

BACKGROUND OF THE INVENTION

Field of the Invention

The present invention relates to recombinant *Trichoderma* host cells producing *Aspergillus fumigatus* cellulolytic enzyme compositions and methods of producing and using the compositions.

Description of the Related Art

Cellulose is a polymer of glucose linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol.

One of the most commercially-utilized cellulolytic enzyme systems is that of *Trichoderma reesei* (teleomorph *Hypocrea jecorina*), which secretes endoglucanases that cleave cellulose chains internally, exocellobiohydrolases that degrade cellulose chains processively from the ends, releasing cellobiose, and beta-glucosidases that hydrolyze cellobiose to glucose. *T. reesei* as a cellulolytic enzyme production system has several advantages such as high yields of secreted proteins, productive under large-scale fermentation, a very active and well understood base cellulolytic enzyme system, and a sequenced and well annotated genome. However, disadvantages of the *T. reesei* cellulolytic enzyme system are that other organisms produce cellulolytic enzymes that are individually superior; hemicellulose-degrading enzymes are insufficient for hemicellulose-rich substrates, and beta-glucosidases are limiting under high solids hydrolysis.

*Aspergillus fumigatus* reportedly produces several cellulases (Nierman et al., 2005, *Nature* 438: 1151-1156). WO 2011/057140 discloses an *Aspergillus fumigatus* cellobiohydrolase I and gene thereof. WO 2011/057140 discloses an *Aspergillus fumigatus* cellobiohydrolase II and gene thereof. WO 2005/047499 discloses an *Aspergillus fumigatus* beta-glucosidase and gene thereof. WO 2010/138754 discloses an *Aspergillus fumigatus* GH61 polypeptide having cellulolytic enhancing activity and gene thereof. WO 2011/057140 discloses an *Aspergillus fumigatus* endoglucanase II and gene thereof. WO 2006/078256 discloses *Aspergillus fumigatus* GH10 xylanases. WO 2011/057140 discloses an *Aspergillus fumigatus* beta-xylosidase and gene thereof.

There is a need in the art for new cellulolytic enzyme systems that can be produced in commercial quantities and can deconstruct cellulosic material more efficiently.

The present invention provides recombinant *Trichoderma* host cells encoding *Aspergillus fumigatus* cellulolytic enzyme compositions and methods of producing and using the compositions.

SUMMARY OF THE INVENTION

The present invention relates to recombinant *Trichoderma* host cells, comprising polynucleotides encoding (i) an *Aspergillus fumigatus* cellobiohydrolase I; (ii) an *Aspergillus fumigatus* cellobiohydrolase II; (iii) an *Aspergillus fumigatus* beta-glucosidase; and (iv) an *Aspergillus fumigatus* GH61 polypeptide having cellulolytic enhancing activity; or homologs thereof.

The present invention also relates to methods of producing an enzyme composition, comprising: (a) cultivating a *Trichoderma* host cell of the present invention under conditions conducive for production of the enzyme composition; and optionally (b) recovering the enzyme composition.

The present invention also relates to enzyme compositions comprising a recovered fermentation broth of a recombinant *Trichoderma* host cell of the present invention.

The present invention also relates to processes for degrading a cellulosic material, comprising: treating the cellulosic material with an enzyme composition comprising a recovered fermentation broth of the present invention.

The present invention also relates to processes for producing a fermentation product, comprising: (a) saccharifying a cellulosic material with an enzyme composition comprising a recovered fermentation broth of the present invention; (b) fermenting the saccharified cellulosic material with one or more (e.g., several) fermenting microorganisms to produce the fermentation product; and (c) recovering the fermentation product from the fermentation.

The present invention further relates to processes of fermenting a cellulosic material, comprising: fermenting the cellulosic material with one or more (e.g., several) fermenting microorganisms, wherein the cellulosic material is saccharified with an enzyme composition comprising a recovered fermentation broth of the present invention.

DEFINITIONS

Figure 1:
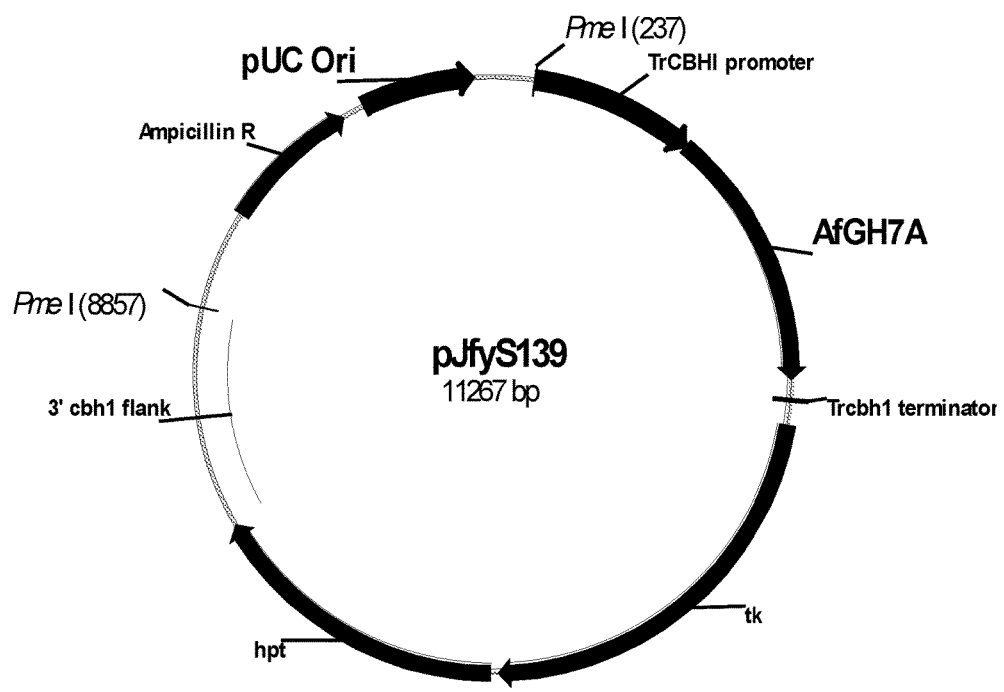
FIG. 1 shows a restriction map of plasmid pJfyS139.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Allelic variant: The term "allelic variant" means any of two or more (e.g., several) alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 μmole of glucuronic or 4-O-methylglucuronic acid per minute at pH 5, 40° C.

Aspartic protease: The term "aspartic protease" means a protease that uses an aspartate residue(s) for catalyzing the hydrolysis of peptide bonds in peptides and proteins. Aspartic proteases are a family of protease enzymes that use an aspartate residue for catalytic hydrolysis of their peptide substrates. In general, they have two highly-conserved aspartates in the active site and are optimally active at acidic pH (Szecsi, 1992, Scand. *J. Clin. Lab. In vest.* Suppl. 210: 5-22). For purposes of the present invention, aspartic protease activity is determined according to the procedure described by Aikawa et al., 2001, *J. Biochem.* 129: 791-794.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20 (polyoxyethylene sorbitan monolaurate).

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 μmole of p-nitrophenolate anion produced per minute at 40° C., pH 5 from 1 mM p-nitrophenyl-beta-D-xyloside as substrate in 100 mM sodium citrate containing 0.01% TWEEN® 20.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters*, 149: 152-156; van Tilbeurgh and Claeyssens, 1985, *FEBS Letters*, 187: 283-288; and Tomme et al., 1988, *Eur. J. Biochem.* 170: 575-581. In the present invention, the Tomme et al. method can be used to determine cellobiohydrolase activity.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1)

measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a polypeptide. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Flanking: The term "flanking" means DNA sequences extending on either side of a specific DNA sequence, locus, or gene. The flanking DNA is immediately adjacent to another DNA sequence, locus, or gene that is to be integrated into the genome of a filamentous fungal cell.

Fragment: The term "fragment" means a polypeptide having one or more (e.g., several) amino acids absent from the amino and/or carboxyl terminus of a mature polypeptide main; wherein the fragment has enzyme activity. In one aspect, a fragment contains at least 85%, e.g., at least 90% or at least 95% of the amino acid residues of the mature polypeptide of an enzyme.

Hemicellulolytic enzyme or hemicellulase: The term "hemicellulolytic enzyme" or "hemicellulase" means one or more (e.g., several) enzymes that hydrolyze a hemicellulosic material. See, for example, Shallom, D. and Shoham, Y. Microbial hemicellulases. *Current Opinion In Microbiology*, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 50° C., 55° C., or 60° C., and pH, e.g., 5.0 or 5.5.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Homologous 3' or 5' region: The term "homologous 3' region" means a fragment of DNA that is identical in sequence or has a sequence identity of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to a region in the genome and when combined with a homologous 5' region can target integration of a piece of DNA to a specific site in the genome by homologous recombination. The term "homologous 5' region" means a fragment of DNA that is identical in sequence to a region in the genome and when combined with a homologous 3' region can target integration of a piece of DNA to a specific site in the genome by homologous recombination. The homologous 5' and 3' regions must be linked in the genome which means they are on the same chromosome and within at least 200 kb of one another.

Homologous flanking region: The term "homologous flanking region" means a fragment of DNA that is identical or has a sequence identity of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to a region in the genome and is located immediately upstream or downstream of a specific site in the genome into which extracellular DNA is targeted for integration.

Homologous repeat: The term "homologous repeat" means a fragment of DNA that is repeated at least twice in the recombinant DNA introduced into a host cell and which can facilitate the loss of the DNA, i.e., selectable marker that is inserted between two homologous repeats, by homologous recombination. A homologous repeat is also known as a direct repeat.

Host cell: The term "host cell" means any cell type that is susceptible to transformation, transfection, transduction, or the like with a nucleic acid construct or expression vector comprising a polynucleotide encoding a polypeptide. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide of an *A. fumigatus* cellobiohydrolase I is amino acids 27 to 532 of SEQ ID NO: 2 based on the SignalP program (Nielsen et al., 1997, *Protein Engineering* 10: 1-6) that predicts amino acids 1 to 26 of SEQ ID NO: 2 are a signal peptide. In another aspect, the mature polypeptide of an *A. fumigatus* cellobiohydrolase II is amino acids 20 to 454 of SEQ ID NO: 4 based on the SignalP program that predicts amino acids 1 to 19 of SEQ ID NO: 4 are a signal peptide. In another aspect, the mature polypeptide of an *A. fumigatus* beta-glucosidase is amino acids 20 to 863 of SEQ ID NO: 6 based on the SignalP program that predicts amino acids 1 to 19 of SEQ ID NO: 6 are a signal peptide. In another aspect, the mature polypeptide of an *A. fumigatus* GH61 polypeptide is amino acids 22 to 250 of SEQ ID NO: 8 based on the SignalP program that predicts amino acids 1 to 21 of SEQ ID NO: 8 are a signal peptide. In another aspect, the mature polypeptide of an *A. fumigatus* endoglucanase I is amino acids 19 to 407 of SEQ ID NO: 10 based on the SignalP program that predicts amino acids 1 to 18 of SEQ ID NO: 10 are a signal peptide. In another aspect, the mature polypeptide of an *A. fumigatus* endoglucanase II is amino acids 19 to 329 of SEQ ID NO: 12 based on the SignalP program that predicts amino acids 1 to 18 of SEQ ID NO: 12 are a signal peptide. In another aspect, the mature polypeptide of an *A. fumigatus* xylanase I is amino acids 18 to 364 of SEQ ID NO: 14 based on the SignalP program that predicts amino acids 1 to 17 of SEQ ID NO: 14 are a signal peptide. In another aspect, the mature polypeptide of an *A. fumigatus* xylanase II is amino acids 20 to 323 of SEQ ID NO: 16 based on the SignalP program that predicts amino acids 1 to 19 of SEQ ID NO: 16 are a signal peptide. In another aspect, the mature polypeptide of an *A. fumigatus* xylanase III is amino acids 20 to 397 of SEQ ID NO: 18 based on the SignalP program that predicts amino acids 1 to 19 of SEQ ID NO: 18 are a signal peptide. In another aspect, the mature polypeptide of an *A. fumigatus* beta-xylosidase is amino acids 21 to 792 of SEQ ID NO: 20 based on the SignalP program that predicts amino acids 1 to 20 of SEQ ID NO: 20 are a signal peptide. In another aspect, the mature polypeptide of an *A. fumigatus* swollenin is amino acids 18 to 470 of SEQ ID NO: 22 based on the SignalP program that predicts amino acids 1 to 17 of SEQ ID NO: 22 are a signal peptide.

In another aspect, the mature polypeptide of a *T. reesei* cellobiohydrolase I is amino acids 18 to 514 of SEQ ID NO: 24 based on the SignalP program that predicts amino acids 1 to 17 of SEQ ID NO: 24 are a signal peptide. In another aspect, the mature polypeptide of a *T. reesei* cellobiohydrolase II is amino acids 19 to 471 of SEQ ID NO: 26 based on the SignalP program that predicts amino acids 1 to 18 of SEQ ID NO: 26 are a signal peptide. In another aspect, the mature polypeptide of a *T. reesei* beta-glucosidase is amino acids 20 to 744 of SEQ ID NO: 28 based on the SignalP program that predicts amino acids 1 to 19 of SEQ ID NO: 28 are a signal peptide. In another aspect, the mature polypeptide of a *T. reesei* endoglucanase I is amino acids 23 to 459 of SEQ ID NO: 30 based on the SignalP program that predicts amino acids 1 to 22 of SEQ ID NO: 30 are a signal peptide. In another aspect, the mature polypeptide of a *T. reesei* endoglucanase II is amino acids 22 to 418 of SEQ ID NO: 32 based on the SignalP program that predicts amino acids 1 to 21 of SEQ ID NO: 32 are a signal peptide. In another aspect, the mature polypeptide of a *T. reesei* xylanase I is amino acids 20 to 229 of SEQ ID NO: 34 based on the SignalP program that predicts amino acids 1 to 19 of SEQ ID NO: 34 are a signal peptide. In another aspect, the mature polypeptide of a *T. reesei* xylanase II is amino acids 20 to 223 of SEQ ID NO: 36 based on the SignalP program that predicts amino acids 1 to 19 of SEQ ID NO: 36 are a signal peptide. In another aspect, the mature polypeptide of a *T. reesei* xylanase III is amino acids 17 to 347 of SEQ ID NO: 38 based on the SignalP program that predicts amino acids 1 to 16 of SEQ ID NO: 38 are a signal peptide. In another aspect, the mature polypeptide of a *T. reesei* beta-xylosidase is amino acids 21 to 797 of SEQ ID NO: 40 based on the SignalP program that predicts amino acids 1 to 20 of SEQ ID NO: 40 are a signal peptide. In another aspect, the mature polypeptide of a *T. reesei* swollenin is amino acids 19 to 493 of SEQ ID NO: 42 based on the SignalP program that predicts amino acids 1 to 18 of SEQ ID NO: 42 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having enzyme activity. In one aspect, the mature polypeptide coding sequence of an *A. fumigatus* cellobiohydrolase I is nucleotides 79 to 1596 of SEQ ID NO: 1 or the cDNA sequence thereof based on the SignalP program (Nielsen et al., 1997, supra) that predicts nucleotides 1 to 78 of SEQ ID NO: 1 encode a signal peptide. In another aspect, the mature polypeptide coding sequence of an *A. fumigatus* cellobiohydrolase II is nucleotides 58 to 1700 of SEQ ID NO: 3 or the cDNA sequence thereof based on the SignalP program that predicts nucleotides 1 to 57 of SEQ ID NO: 3 encode a signal peptide. In another aspect, the mature polypeptide coding sequence of an *A. fumigatus* beta-glucosidase is nucleotides 58 to 2580 of SEQ ID NO: 5 or the cDNA sequence thereof based on the SignalP program that predicts nucleotides 1 to 57 of SEQ ID NO: 5 encode a signal peptide. In another aspect, the mature polypeptide coding sequence of an *A. fumigatus* GH61 polypeptide is nucleotides 64 to 859 of SEQ ID NO: 7 or the cDNA sequence thereof based on the SignalP program that predicts nucleotides 1 to 63 of SEQ ID NO: 7 encode a signal peptide. In another aspect, the mature polypeptide coding sequence of an *A. fumigatus* endoglucanase I is nucleotides 55 to 1221 of SEQ ID NO: 9 or the cDNA sequence thereof based on the SignalP program that predicts nucleotides 1 to 54 of SEQ ID NO: 9 encode a signal peptide. In another aspect, the mature polypeptide coding sequence of an *A. fumigatus* endoglucanase II is nucleotides 55 to 1248 of SEQ ID NO: 11 or the cDNA sequence thereof based on the SignalP program that predicts nucleotides 1 to 54 of SEQ ID NO: 11 encode a signal peptide. In another aspect, the mature polypeptide coding sequence of an *A. fumigatus* xylanase I is nucleotides 52 to 1145 of SEQ ID NO: 13 or the cDNA sequence thereof based on the SignalP program that predicts nucleotides 1 to 51 of SEQ ID NO: 13 encode a signal peptide. In another aspect, the mature polypeptide coding sequence of an *A. fumigatus* xylanase II is nucleotides 58 to 1400 of SEQ ID NO: 15 or the cDNA sequence thereof based on the SignalP program that predicts nucleotides 1 to 57 of SEQ ID NO: 15 encode a signal peptide. In another aspect, the mature polypeptide coding sequence of an *A. fumigatus* xylanase III is nucleotides 107 to 1415 of SEQ ID NO: 17 or the cDNA sequence thereof based on the SignalP program that predicts nucleotides 1 to 106 of SEQ ID NO: 17 encode a signal peptide. In another aspect, the mature polypeptide coding sequence of an *A. fumigatus* beta-xylosidase is nucleotides 61 to 2373 of SEQ ID NO: 19 or the cDNA sequence thereof based on the SignalP program that predicts nucleotides 1 to 60 of SEQ ID NO: 19 encode a signal peptide. In another aspect, the mature polypeptide coding sequence of an *A. fumigatus* swollenin is nucleotides 52 to 1657 of SEQ ID NO: 21 or the cDNA sequence thereof based on the SignalP program that predicts nucleotides 1 to 51 of SEQ ID NO: 21 encode a signal peptide.

In another aspect, the mature polypeptide coding sequence of a *T. reesei* cellobiohydrolase I is nucleotides 52 to 1545 of SEQ ID NO: 23 or the cDNA sequence thereof based on the SignalP program that predicts nucleotides 1 to 51 of SEQ ID NO: 23 encode a signal peptide. In another aspect, the mature polypeptide coding sequence of a *T. reesei* cellobiohydrolase II is nucleotides 55 to 1608 of SEQ ID NO: 25 or the cDNA sequence thereof based on the SignalP program that predicts nucleotides 1 to 54 of SEQ ID NO: 25 encode a signal peptide. In another aspect, the mature polypeptide coding sequence of a *T. reesei* beta-glucosidase is nucleotides 58 to 2612 of SEQ ID NO: 27 or the cDNA sequence thereof based on the SignalP program that predicts nucleotides 1 to 57 of SEQ ID NO: 27 encode a signal peptide. In another aspect, the mature polypeptide coding sequence of a *T. reesei* endoglucanase I is nucleotides 67 to 1374 of SEQ ID NO: 29 or the cDNA sequence thereof based on the SignalP program that predicts nucleotides 1 to 66 of SEQ ID NO: 29 encode a signal peptide. In another aspect, the mature polypeptide coding sequence of a *T. reesei* endoglucanase II is nucleotides 64 to 1254 of SEQ ID NO: 31 or the cDNA sequence thereof based on the SignalP program that predicts nucleotides 1 to 63 of SEQ ID NO: 31 encode a signal peptide. In another aspect, the mature polypeptide coding sequence of a *T. reesei* xylanase I is nucleotides 58 to 749 of SEQ ID NO: 33 or the cDNA sequence thereof based on the SignalP program that predicts nucleotides 1 to 57 of SEQ ID NO: 33 encode a signal peptide. In another aspect, the mature polypeptide coding sequence of a *T. reesei* xylanase II is nucleotides 58 to 778 of SEQ ID NO: 35 or the cDNA sequence thereof based on the SignalP program that predicts nucleotides 1 to 57 of SEQ ID NO: 35 encode a signal peptide. In another aspect, the mature polypeptide coding sequence of a *T. reesei* xylanase III is nucleotides 49 to 1349 of SEQ ID NO: 37 or the cDNA sequence thereof based on the SignalP program that predicts nucleotides 1 to 48 of SEQ ID NO: 37 encode a signal peptide. In another aspect, the mature polypeptide coding sequence of a *T. reesei* beta-xylosidase is nucleotides 61 to 2391 of SEQ ID NO: 39 or the cDNA sequence thereof based on the SignalP program that predicts nucleotides 1 to 60 of SEQ ID NO: 39 encode a signal peptide. In another aspect, the mature polypeptide coding sequence of a *T. reesei* swollenin is nucleotides 55 to 2776 of SEQ ID NO: 41 or the cDNA sequence thereof based on the SignalP program that predicts nucleotides 1 to 54 of SEQ ID NO: 41 encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more (e.g., several) control sequences.

Operably linked: The term "operably linked" means a configuration in which a control sequence is placed at an appropriate position relative to the coding sequence of a polynucleotide such that the control sequence directs expression of the coding sequence.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In a preferred aspect, a mixture of CELLUCLAST® 1.5 L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Pretreated corn stover: The term "PCS" or "Pretreated Corn Stover" means a cellulosic material derived from corn stover by treatment with heat and dilute sulfuric acid, alkaline pretreatment, or neutral pretreatment.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment–
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment–Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having enzyme activity. In one aspect, a subsequence contains at least 85%, e.g., at least 90% or at least 95% of the nucleotides of the mature polypeptide coding sequence of an enzyme.

Subtilisin-like serine protease: The term "subtilisin-like serine protease" means a protease with a substrate specificity similar to subtilisin that uses a serine residue for catalyzing the hydrolysis of peptide bonds in peptides and proteins. Subtilisin-like proteases (subtilases) are serine proteases characterized by a catalytic triad of the three amino acids aspartate, histidine, and serine. The arrangement of these catalytic residues is shared with the prototypical subtilisin from *Bacillus licheniformis* (Siezen and Leunissen, 1997, *Protein Science* 6: 501-523). Subtilisin-like serine protease activity can be determined using a synthetic substrate, N-succinyl-L-Ala-L-Ala-L-Pro-L-Phe-p-nitroanilide (AAPF) (Bachem AG, Bubendorf, Switzerland) in 100 mM NaCl-100 mM MOPS pH 7.0 at 50° C. for 3 hours and then the absorbance at 405 nm is measured.

Targeted integration: The term "targeted integration" means the stable integration of extracellular DNA at a defined genomic locus.

Transformant: The term "transformant" means a cell which has taken up extracellular DNA (foreign, artificial or modified) and expresses the gene(s) contained therein.

Transformation: The term "transformation" means the introduction of extracellular DNA into a cell, i.e., the genetic alteration of a cell resulting from the direct uptake, incorporation and expression of exogenous genetic material (exogenous DNA) from its surroundings and taken up through the cell membrane(s).

Transformation efficiency: The term "transformation efficiency" means the efficiency by which cells can take up the extracellular DNA and express the gene(s) contained therein, which is calculated by dividing the number of positive transformants expressing the gene(s) by the amount of DNA used during a transformation procedure.

Trypsin-like serine protease: The term "trypsin-like serine protease" means a protease with a substrate specificity similar to trypsin that uses a serine residue for catalyzing the hydrolysis of peptide bonds in peptides and proteins. For purposes of the present invention, trypsin-like serine protease activity is determined according to the procedure described by Dienes et al., 2007, *Enzyme and Microbial Technology* 40: 1087-1094.

Variant: The term "variant" means a polypeptide having enzyme activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by *Schizophyllum commune*, *FEBS Letters* 580(19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

DETAILED DESCRIPTION OF THE INVENTION

The present invention relates to recombinant *Trichoderma* host cells, comprising polynucleotides encoding (i) an *Aspergillus fumigatus* cellobiohydrolase I; (ii) an *Aspergillus fumigatus* cellobiohydrolase II; (iii) an *Aspergillus fumigatus* beta-glucosidase; and (iv) an *Aspergillus fumigatus* GH61 polypeptide having cellulolytic enhancing activity; or homologs thereof. In one aspect, the recombinant *Trichoderma* host cells further comprise one or more (e.g., several) polynucleotides encoding one or more (e.g., several) enzymes selected from the group consisting of: (i) an *Aspergillus fumigatus* endoglucanase I; (ii) an *Aspergillus fumigatus* endoglucanase II; (iii) an *Aspergillus fumigatus* xylanase; (iv) an *Aspergillus fumigatus* beta-xylosidase; and (v) an *Aspergillus fumigatus* swollenin; or homologs thereof.

The recombinant *Trichoderma* host cells of the present invention unexpectedly produce enzyme compositions of *Aspergillus fumigatus* cellulolytic enzymes that are more efficient in the deconstruction of cellulosic material than a native cellulolytic enzyme composition produced by *T. reesei* or *A. fumigatus*.

*Aspergillus fumigatus* Cellulases and Hemicellulases

In the present invention, any *Aspergillus fumigatus* cellobiohydrolase I, *Aspergillus fumigatus* cellobiohydrolase II, *Aspergillus fumigatus* beta-glucosidase, *Aspergillus fumigatus* GH61 polypeptide having cellulolytic enhancing activity, *Aspergillus fumigatus* endoglucanase I, *Aspergillus fumigatus* endoglucanase II, *Aspergillus fumigatus* xylanase, *Aspergillus fumigatus* beta-xylosidase, and *Aspergillus fumigatus* swollenin, or homologs thereof, may be used.

In one aspect, the *Aspergillus fumigatus* cellobiohydrolase I or a homolog thereof is selected from the group consisting of: (i) a cellobiohydrolase I comprising or consisting of the mature polypeptide of SEQ ID NO: 2; (ii) a cellobiohydrolase I comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 2; (iii) a cellobiohydrolase I encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 1; and (iv) a cellobiohydrolase I encoded by a polynucleotide that hybridizes under at least high stringency conditions, e.g., very high stringency conditions, with the mature polypeptide coding sequence of SEQ ID NO: 1 or the full-length complement thereof.

In another aspect, the *Aspergillus fumigatus* cellobiohydrolase II or a homolog thereof is selected from the group consisting of: (i) a cellobiohydrolase II comprising or consisting of the mature polypeptide of SEQ ID NO: 4; (ii) a cellobiohydrolase II comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 4; (iii) a cellobiohydrolase II encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 3; and (iv) a cellobiohydrolase II encoded by a polynucleotide that hybridizes under at least high stringency conditions, e.g., very high stringency conditions, with the mature polypeptide coding sequence of SEQ ID NO: 3 or the full-length complement thereof.

In another aspect, the *Aspergillus fumigatus* beta-glucosidase or a homolog thereof is selected from the group consisting of: (i) a beta-glucosidase comprising or consisting of the mature polypeptide of SEQ ID NO: 6; (ii) a beta-glucosidase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 6; (iii) a beta-glucosidase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 5; and (iv) a beta-glucosidase encoded by a polynucleotide that hybridizes under at least high stringency conditions, e.g., very high stringency conditions, with the mature polypeptide coding sequence of SEQ ID NO: 5 or the full-length complement thereof.

In another aspect, the *Aspergillus fumigatus* GH61 polypeptide having cellulolytic enhancing activity or a homolog thereof is selected from the group consisting of: (i) a GH61 polypeptide having cellulolytic enhancing activity comprising or consisting of the mature polypeptide of SEQ ID NO: 8; (ii) a GH61 polypeptide having cellulolytic enhancing activity comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 8; (iii) a GH61 polypeptide having cellulolytic enhancing activity encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 7; and (iv) a GH61 polypeptide having cellulolytic enhancing activity encoded by a polynucleotide that hybridizes under at least high stringency conditions, e.g., very high stringency conditions, with the mature polypeptide coding sequence of SEQ ID NO: 7 or the full-length complement thereof.

In another aspect, the *Aspergillus fumigatus* endoglucanase I or a homolog thereof is selected from the group consisting of: (i) an endoglucanase I comprising or consisting of the mature polypeptide of SEQ ID NO: 10; (ii) an endoglucanase I comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 10; (iii) an endoglucanase I encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 9; and (iv) an endoglucanase I encoded by a polynucleotide that hybridizes under at least high stringency conditions, e.g., very high stringency conditions, with the mature polypeptide coding sequence of SEQ ID NO: 9 or the full-length complement thereof.

In another aspect, the *Aspergillus fumigatus* endoglucanase II or a homolog thereof is selected from the group consisting of: an endoglucanase II comprising or consisting of the mature polypeptide of SEQ ID NO: 12; (i) an endoglucanase II comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 12; (ii) an endoglucanase II encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 11; and (iii) an endoglucanase II encoded by a polynucleotide that hybridizes under at least high stringency conditions, e.g., very high stringency conditions, with the mature polypeptide coding sequence of SEQ ID NO: 11 or the full-length complement thereof.

In another aspect, the *Aspergillus fumigatus* xylanase or a homolog thereof is selected from the group consisting of: (i)

a xylanase comprising or consisting of the mature polypeptide of SEQ ID NO: 14, SEQ ID NO: 16, or SEQ ID NO: 18; (ii) a xylanase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 14, SEQ ID NO: 16, or SEQ ID NO: 18; (iii) a xylanase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 13, SEQ ID NO: 15, or SEQ ID NO: 17; and (iv) a xylanase encoded by a polynucleotide that hybridizes under at least high stringency conditions, e.g., very high stringency conditions, with the mature polypeptide coding sequence of SEQ ID NO: 13, SEQ ID NO: 15, or SEQ ID NO: 17; or the full-length complement thereof.

In another aspect, the *Aspergillus fumigatus* beta-xylosidase or a homolog thereof is selected from the group consisting of: (i) a beta-xylosidase comprising or consisting of the mature polypeptide of SEQ ID NO: 20; (ii) a beta-xylosidase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 20; (iii) a beta-xylosidase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 19; and (iv) a beta-xylosidase encoded by a polynucleotide that hybridizes under at least high stringency conditions, e.g., very high stringency conditions, with the mature polypeptide coding sequence of SEQ ID NO: 19 or the full-length complement thereof.

In another aspect, the *Aspergillus fumigatus* swollenin or a homolog thereof is selected from the group consisting of: (i) a swollenin comprising or consisting of the mature polypeptide of SEQ ID NO: 22; (ii) a swollenin comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 22; (iii) a swollenin encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 21; and (iv) a swollenin encoded by a polynucleotide that hybridizes under at least high stringency conditions, e.g., very high stringency conditions, with the mature polypeptide coding sequence of SEQ ID NO: 21 or the full-length complement thereof.

The polynucleotide of SEQ ID NO: 1, 3, 5, 7, 9, 11, 13, 15, 17, 19, or 21, or a subsequence thereof, as well as the polypeptide of SEQ ID NO: 2, 4, 6, 8, 10, 12, 14, 16, 18, 20, or 22, or a fragment thereof, may be used to design nucleic acid probes to identify and clone DNA encoding enzymes according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library may be screened for DNA that hybridizes with the probes described above and encodes an enzyme. Genomic or other DNA may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, 3, 5, 7, 9, 11, 13, 15, 17, 19, or 21, or a subsequence thereof, the carrier material is used in a Southern blot.

For purposes of the present invention, hybridization indicates that the polynucleotide hybridizes to a labeled nucleic acid probe corresponding to (i) SEQ ID NO: 1, 3, 5, 7, 9, 11, 13, 15, 17, 19, or 21; (ii) the mature polypeptide coding sequence of SEQ ID NO: 1, 3, 5, 7, 9, 11, 13, 15, 17, 19, or 21; (iii) the cDNA sequence thereof; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is SEQ ID NO: 1, 3, 5, 7, 9, 11, 13, 15, 17, 19, or 21, or the mature polypeptide coding sequence thereof. In another aspect, the nucleic acid probe is a polynucleotide that encodes the polypeptide of SEQ ID NO: 2, 4, 6, 8, 10, 12, 14, 16, 18, 20, or 22; the mature polypeptide thereof; or a fragment thereof.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Aspergillus fumigatus* and thus, for example, may be an allelic or species variant of the polypeptide encoding region of the polynucleotide.

A chemically modified or protein engineered mutant of an *A. fumigatus* enzyme above (or protein) may also be used.

An *A. fumigatus* enzyme may also be hybrid enzyme in which a region of the *A. fumigatus* enzyme is fused at the N-terminus or the C-terminus of a region of another enzyme.

An *A. fumigatus* enzyme may further be a fusion polypeptide or cleavable fusion polypeptide in which another enzyme is fused at the N-terminus or the C-terminus of the *A. fumigatus* enzyme. A fusion polypeptide is produced by fusing a polynucleotide encoding another enzyme to a polynucleotide encoding the *A. fumigatus* enzyme. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The *Aspergillus fumigatus* enzyme may be further one or more (e.g., several) *A. fumigatus* enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, and a mannosidase.

The *Aspergillus fumigatus* enzyme may be even further one or more (e.g., several) *A. fumigatus* enzymes selected from the group consisting of an esterase, an expansin, a laccase, a ligninolytic enzyme, a pectinase, a peroxidase, and a protease.

Trichoderma Host Cells

The *Trichoderma* host cell may be any *Trichoderma* cell useful in the recombinant production of an enzyme or protein. For example, the *Trichoderma* cell may be a *Trichoderma harzianum*, *Trichoderma koningii*, *Trichoderma longibrachiatum*, *Trichoderma reesei*, or *Trichoderma viride* cell. In one aspect, the *Trichoderma* cell is a *Trichoderma harzianum* cell. In another aspect, the *Trichoderma* cell is a *Trichoderma koningii* cell. In another aspect, the *Trichoderma* cell is a *Trichoderma longibrachiatum* cell. In another aspect, the *Trichoderma* cell is a *Trichoderma reesei* cell. In another aspect, the *Trichoderma* cell is a *Trichoderma viride* cell.

In another aspect, the *Trichoderma reesei* cell is *Trichoderma reesei* RutC30. In another aspect, the *Trichoderma reesei* cell is *Trichoderma reesei* TV10. In another aspect, the *Trichoderma reesei* cell is a mutant of *Trichoderma reesei* RutC30. In another aspect, the *Trichoderma reesei* cell is mutant of *Trichoderma reesei* TV10. In another aspect, the *Trichoderma reesei* cell is a morphological mutant of *Trichoderma reesei*. See, for example, WO 97/26330, which is incorporated herein by reference in its entirety.

The *Trichoderma* cell may be transformed by a process involving protoplast formation, transformation of the protoplasts, and regeneration of the cell wall in a manner known per se. Suitable procedures for transformation of *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422.

One or more (e.g., several) native cellulase and/or hemicellulase genes may be inactivated in the *Trichoderma* host cell by disrupting or deleting the genes, or a portion thereof, which results in the mutant cell producing less or none of the cellulase and/or hemicellulase than the parent cell when cultivated under the same conditions. In one aspect, the one or more (e.g., several) cellulase genes encode enzymes selected from the group consisting of cellobiohydrolase I, cellobiohydrolase II, endoglucanase I, endoglucanase II, beta-glucosidase, and swollenin. In another aspect, the one or more (e.g., several) hemicellulase genes encode enzymes selected from the group consisting of xylanase I, xylanase II, xylanase III, and beta-xylosidase. In another aspect, the one or more (e.g., several) hemicellulase genes encode enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, and a mannosidase.

The mutant cell may be constructed by reducing or eliminating expression of a polynucleotide encoding a *Trichoderma* cellulase or hemicellulase using methods well known in the art, for example, insertions, disruptions, replacements, or deletions. In a preferred aspect, the polynucleotide is inactivated. The polynucleotide to be modified or inactivated may be, for example, the coding region or a part thereof essential for activity, or a regulatory element required for expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the polynucleotide may also be accomplished by insertion, substitution, or deletion of one or more (e.g., several) nucleotides in the gene or a regulatory element required for transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene. By homologous recombination, the defective nucleic acid sequence replaces the endogenous polynucleotide. It may be desirable that the defective polynucleotide also encodes a marker that may be used for selection of transformants in which the polynucleotide has been modified or destroyed. In an aspect, the polynucleotide is disrupted with a selectable marker such as those described herein.

Modification or inactivation of the polynucleotide may also be accomplished by inhibiting expression of an enzyme encoded by the polynucleotide in a cell by administering to the cell or expressing in the cell a double-stranded RNA (dsRNA) molecule, wherein the dsRNA comprises a subsequence of a polynucleotide encoding the enzyme. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA for inhibiting transcription. In another preferred aspect, the dsRNA is micro RNA for inhibiting translation. In another aspect, the double-stranded RNA (dsRNA) molecules comprise a portion of the mature polypeptide coding sequence of SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, and/or SEQ ID NO: 41 for inhibiting expression of the polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs can be used in gene-silencing to selectively degrade RNA using a dsRNAi of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art; see, for example, U.S. Pat. Nos. 6,489,127; 6,506,559; 6,511,824; and 6,515,109.

In one aspect, the *Trichoderma* cellobiohydrolase I or a homolog thereof is selected from the group consisting of: (i) a cellobiohydrolase I comprising or consisting of the mature polypeptide of SEQ ID NO: 24; (ii) a cellobiohydrolase I comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 24; (iii) a cellobiohydrolase I encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 23; and (iv) a cellobiohydrolase I encoded by a polynucleotide that hybridizes under at least high stringency conditions, e.g., very high stringency conditions, with the mature polypeptide coding sequence of SEQ ID NO: 23 or the full-length complement thereof.

In another aspect, the *Trichoderma* cellobiohydrolase II or a homolog thereof is selected from the group consisting of: (i) a cellobiohydrolase II comprising or consisting of the mature polypeptide of SEQ ID NO: 26; (ii) a cellobiohydrolase II comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 26; (iii) a cellobiohydrolase II encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 25; and (iv) a cellobiohydrolase II encoded by a polynucleotide that hybridizes under at least high stringency conditions, e.g., very high stringency conditions, with the mature polypeptide coding sequence of SEQ ID NO: 25 or the full-length complement thereof.

In another aspect, the *Trichoderma* beta-glucosidase or a homolog thereof is selected from the group consisting of: (i) a beta-glucosidase comprising or consisting of the mature polypeptide of SEQ ID NO: 28; (ii) a beta-glucosidase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 28; (iii) a beta-glucosidase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 27; and (iv) a beta-glucosidase encoded by a polynucleotide that hybridizes under at least high stringency conditions, e.g., very high stringency conditions, with the mature polypeptide coding sequence of SEQ ID NO: 27 or the full-length complement thereof.

In another aspect, the *Trichoderma* endoglucanase I or a homolog thereof is selected from the group consisting of: (i) an endoglucanase I comprising or consisting of the mature polypeptide of SEQ ID NO: 30; (ii) an endoglucanase I comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 30; (iii) an endoglucanase I encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 29; and (iv) an endoglucanase I encoded by a polynucleotide that hybridizes under at least high stringency conditions, e.g., very high stringency conditions, with the mature polypeptide coding sequence of SEQ ID NO: 29 or the full-length complement thereof.

In another aspect, the *Trichoderma* endoglucanase II or a homolog thereof is selected from the group consisting of: (i) an endoglucanase II comprising or consisting of the mature polypeptide of SEQ ID NO: 32; (ii) an endoglucanase II comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 32; (iii) an endoglucanase II encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 31; and (iv) an endoglucanase II encoded by a polynucleotide that hybridizes under at least high stringency conditions, e.g., very high stringency conditions, with the mature polypeptide coding sequence of SEQ ID NO: 31 or the full-length complement thereof.

In another aspect, the *Trichoderma* xylanase or a homolog thereof is selected from the group consisting of: (i) a xylanase comprising or consisting of the mature polypeptide of SEQ ID NO: 34; (ii) a xylanase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 34; (iii) a xylanase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 33; and (iv) a xylanase encoded by a polynucleotide that hybridizes under at least high stringency conditions, e.g., very high stringency conditions, with the mature polypeptide coding sequence of SEQ ID NO: 33; or the full-length complement thereof.

In another aspect, the *Trichoderma* xylanase or a homolog thereof is selected from the group consisting of: (i) a xylanase comprising or consisting of the mature polypeptide of SEQ ID NO: 36; (ii) a xylanase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 36; (iii) a xylanase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 35; and (iv) a xylanase encoded by a polynucleotide that hybridizes under at least high stringency conditions, e.g., very high stringency conditions, with the mature polypeptide coding sequence of SEQ ID NO: 35; or the full-length complement thereof.

In another aspect, the *Trichoderma* xylanase or a homolog thereof is selected from the group consisting of: (i) a xylanase comprising or consisting of the mature polypeptide of SEQ ID NO: 38; (ii) a xylanase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 38; (iii) a xylanase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 37; and (iv) a xylanase encoded by a polynucleotide that hybridizes under at least high stringency conditions, e.g., very high stringency conditions, with the mature polypeptide coding sequence of SEQ ID NO: 37; or the full-length complement thereof.

In another aspect, the *Trichoderma* beta-xylosidase or a homolog thereof is selected from the group consisting of: (i) a beta-xylosidase comprising or consisting of the mature polypeptide of SEQ ID NO: 40; (ii) a beta-xylosidase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 40; (iii) a beta-xylosidase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 39; and (iv) a beta-xylosidase encoded by a polynucleotide that hybridizes under at least high stringency conditions, e.g., very high stringency conditions, with the mature polypeptide coding sequence of SEQ ID NO: 39 or the full-length complement thereof.

In another aspect, the *Trichoderma* swollenin or a homolog thereof is selected from the group consisting of: (i) a swollenin comprising or consisting of the mature polypeptide of SEQ ID NO: 42; (ii) a swollenin comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 42; (iii) a swollenin encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 41; and (iv) a swollenin encoded by a polynucleotide that hybridizes under at least high stringency conditions, e.g., very high stringency conditions, with the mature polypeptide coding sequence of SEQ ID NO: 41 or the full-length complement thereof.

In one aspect, a *Trichoderma* cellobiohydrolase I gene is inactivated. In another aspect, a *Trichoderma* cellobiohydrolase II gene is inactivated. In another aspect, a *Trichoderma* endoglucanase I gene is inactivated. In another aspect, a *Trichoderma* endoglucanase II gene is inactivated. In another aspect, a *Trichoderma* beta-glucosidase gene is inactivated. In another aspect, a *Trichoderma* xylanase gene is inactivated. In another aspect, a *Trichoderma* beta-xylosidase gene is inactivated. In another aspect, a *Trichoderma* swollenin gene is inactivated.

In another aspect, a *Trichoderma* cellobiohydrolase I gene and a *Trichoderma* cellobiohydrolase II gene are inactivated.

In another aspect, two or more (e.g., several) of the genes selected from the group consisting of cellobiohydrolase I, cellobiohydrolase II, endoglucanase I, endoglucanase II, beta-glucosidase, xylanase I, xylanase II, xylanase III, beta-xylosidase, and swollenin genes are inactivated. In another aspect, three or more (e.g., several) of the genes selected from the group consisting of cellobiohydrolase I, cellobiohydrolase II, endoglucanase I, endoglucanase II, beta-glucosidase, xylanase I, xylanase II, xylanase III, beta-xylosidase, and swollenin genes are inactivated. In another aspect, four or more (e.g., several) of the genes selected from the group consisting of cellobiohydrolase I, cellobiohydrolase II, endoglucanase I, endoglucanase II, beta-glucosidase, xylanase I, xylanase II, xylanase III, beta-xylosidase, and swollenin genes are inactivated. In another aspect, five or more (e.g., several) of the genes selected from the group consisting of cellobiohydrolase I, cellobiohydrolase II, endoglucanase I, endoglucanase II, beta-glucosidase, xylanase I, xylanase II, xylanase III, beta-xylosidase, and swollenin genes are inactivated. In another aspect, six or more (e.g., several) of the genes selected from the group consisting of cellobiohydrolase I, cellobiohydrolase II, endoglucanase I, endoglucanase II, beta-glucosidase, xylanase I, xylanase II, xylanase III, beta-xylosidase, and swollenin genes are inactivated. In another aspect, seven or more (e.g., several) of the genes selected from the group consisting of cellobiohydrolase I, cellobiohydrolase II, endoglucanase I, endoglucanase II, beta-glucosidase, xylanase I, xylanase II, xylanase III, beta-xylosidase, and swollenin genes are inactivated. In another aspect, eight or more (e.g., several) of the genes selected from the group consisting of cellobiohydrolase I, cellobiohydrolase II, endoglucanase I, endoglucanase II, beta-glucosidase, xylanase I, xylanase II, xylanase III, beta-xylosidase, and swollenin genes are inactivated. In another aspect, nine or more (e.g., several) of the genes selected from the group consisting of cellobiohydrolase I, cellobiohydrolase II, endoglucanase I, endoglucanase II, beta-glucosidase, xylanase I, xylanase II, xylanase III, beta-xylosidase, and swollenin genes are inactivated.

In another aspect, the cellobiohydrolase I, cellobiohydrolase II, endoglucanase I, endoglucanase II, beta-glucosidase, and beta-xylosidase genes are inactivated. In another aspect, the cellobiohydrolase I, cellobiohydrolase II, endoglucanase I, endoglucanase II, beta-glucosidase, xylanase I, xylanase II, xylanase III, beta-xylosidase, and swollenin genes are inactivated.

In another aspect, one or more (e.g., several) protease genes are inactivated. In another aspect, the one or more (e.g., several) protease genes are subtilisin-like serine protease, aspartic protease, and trypsin-like serine protease genes as described in WO 2011/075677, which is incorporated herein by reference in its entirety.

In each of the aspects above, the *Trichoderma* enzyme is a *Trichoderma harzianum*, *Trichoderma koningii*, *Trichoderma longibrachiatum*, *Trichoderma reesei*, or *Trichoderma viride* enzyme. In another aspect, the *Trichoderma* enzyme is a *Trichoderma harzianum* enzyme. In another aspect, the *Trichoderma* enzyme is a *Trichoderma koningii* enzyme. In another aspect, the *Trichoderma* enzyme is a *Trichoderma longibrachiatum* enzyme. In another aspect, the *Trichoderma* enzyme is a *Trichoderma reesei* cell. In another aspect, the *Trichoderma* enzyme is a *Trichoderma viride* enzyme.

Nucleic Acid Constructs

Nucleic acid constructs comprising a polynucleotide encoding an *Aspergillus fumigatus* enzyme or protein can be constructed by operably linking one or more (e.g., several) control sequences to the polynucleotide to direct the expression of the coding sequence in a *Trichoderma* host cell under conditions compatible with the control sequences. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a *Trichoderma* host cell for expression of a polynucleotide encoding an enzyme or protein. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs in a *Trichoderma* host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147, which is incorporated herein in its entirety.

The control sequence may also be a transcription terminator, which is recognized by a *Trichoderma* host cell to terminate transcription. The terminator is operably linked to the 3'-terminus of the polynucleotide encoding the polypeptide. Any terminator that is functional in the host cell may be used in the present invention.

Preferred terminators for *Trichoderma* host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

The control sequence may also be a leader, a nontranslated region of an mRNA that is important for translation by a *Trichoderma* host cell. The leader is operably linked to the 5'-terminus of the polynucleotide encoding the polypeptide. Any leader that is functional in the host cell may be used.

Preferred leaders for *Trichoderma* host cells are obtained from the genes for *Aspergillus oryzae* TAKA amylase and *Aspergillus nidulans* triose phosphate isomerase.

The control sequence may also be a polyadenylation sequence, a sequence operably linked to the 3'-terminus of the polynucleotide and, when transcribed, is recognized by a *Trichoderma* host cell as a signal to add polyadenosine residues to transcribed mRNA. Any polyadenylation sequence that is functional in the host cell may be used.

Preferred polyadenylation sequences for *Trichoderma* host cells are obtained from the genes for *Aspergillus nidulans* anthranilate synthase, *Aspergillus niger* glucoamylase, *Aspergillus niger* alpha-glucosidase *Aspergillus oryzae* TAKA amylase, *Fusarium oxysporum* trypsin-like protease, *Trichoderma reesei* cellobiohydrolase I, *Trichoderma reesei* cellobiohydrolase II, and *Trichoderma reesei* endoglucanase V.

The control sequence may also be a signal peptide coding region that encodes a signal peptide linked to the N-terminus of a polypeptide and directs the polypeptide into a cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for *Trichoderma* host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, *Rhizomucor miehei* aspartic proteinase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, and *Trichoderma reesei* endoglucanase V.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Myceliophthora thermophila* laccase (WO 95/33836) and *Rhizomucor miehei* aspartic proteinase.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of a *Trichoderma* host cell. Examples of regulatory sequences are those that cause expression of the gene to be turned on or off in response to a chemical or physical stimulus, including the presence of a regulatory compound. Regulatory sequences include the *Aspergillus niger* glucoamylase promoter, *Aspergillus oryzae* TAKA alpha-amylase promoter, *Aspergillus oryzae* glucoamylase promoter, *Trichoderma reesei* cellobiohydrolase I promoter, and *Trichoderma reesei* cellobiohydrolase II promoter. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

Recombinant expression vectors can be constructed comprising a polynucleotide encoding an *Aspergillus fumigatus* enzyme or protein, a promoter, a terminator, and transcriptional and translational stop signals. The various nucleotide and control sequences may be joined together to produce a recombinant expression vector that may include one or more (e.g., several) convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (e.g., several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of selectable markers for use in a *Trichoderma* host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes. Examples of bacterial selectable markers are markers that confer antibiotic resistance such as ampicillin, chloramphenicol, kanamycin, neomycin, spectinomycin, or tetracycline resistance.

The selectable marker may be a dual selectable marker system as described in WO 2010/039889 A2, which is incorporated herein by reference in its entirety. In one aspect, the selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in a *Trichoderma* host cell. The origin of replication may be any plasmid replicator mediating autonomous replication that functions in a cell. The term "origin of replication" or "plasmid replicator" means a polynucleotide that enables a plasmid or vector to replicate in vivo.

Examples of origins of replication useful in a *Trichoderma* host cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide may be inserted into a *Trichoderma* host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors are well known to one skilled in the art (see, e.g., Sambrook et al., 1989, supra).

Methods of Production

The present invention also relates to methods of producing an enzyme composition comprising *Aspergillus fumigatus* cellulases and/or hemicellulases, comprising (a) cultivating a *Trichoderma* recombinant host cell of the present invention under conditions conducive for production of the enzyme composition; and (b) recovering the enzyme composition.

The *Trichoderma* host cells are cultivated in a nutrient medium suitable for production of the enzyme composition using methods known in the art. For example, the cell may be cultivated by shake flask cultivation, or small-scale or large-scale fermentation (including continuous, batch, fed-batch, or solid state fermentations) in laboratory or industrial fermentors in a suitable medium and under conditions allowing the enzyme(s) to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection).

The *A. fumigatus* cellulases and/or hemicellulases may be detected using methods known in the art that are specific for the enzyme. These detection methods include, but are not limited to, use of specific antibodies, formation of an enzyme product, or disappearance of an enzyme substrate. For example, an enzyme assay may be used to determine activity.

The *A. fumigatus* cellulases and/or hemicellulases may be recovered using methods known in the art. For example, the enzyme may be recovered from the nutrient medium by conventional procedures including, but not limited to, collection, centrifugation, filtration, extraction, spray-drying, evaporation, or precipitation. In one aspect, the whole fermentation broth is recovered.

The *A. fumigatus* cellulases and/or hemicellulases may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

Enzyme Compositions

The present invention also relates to enzyme composition comprising a recovered fermentation broth of a recombinant *Trichoderma* host cell of the present invention. In one aspect, the enzyme composition may have one or more components of the fermentation broth removed. In another aspect, the enzyme composition may have no components of the fermentation broth removed.

The enzyme composition comprises (i) an *Aspergillus fumigatus* cellobiohydrolase I; (ii) an *Aspergillus fumigatus* cellobiohydrolase II; (iii) an *Aspergillus fumigatus* beta-glucosidase; and (iv) an *Aspergillus fumigatus* GH61 polypeptide having cellulolytic enhancing activity, or homologs thereof, as described herein. In one aspect, the enzyme composition further comprises one or more (e.g., several) enzymes selected from the group consisting of: (i) an *Aspergillus fumigatus* endoglucanase I; (ii) an *Aspergillus fumigatus* endoglucanase II; (iii) an *Aspergillus fumigatus* xylanase; (iv) an *Aspergillus fumigatus* beta-xylosidase; (v) an *Aspergillus fumigatus* swollenin; or (vi) combinations thereof; or a homolog or homologs thereof, as described herein. In another aspect, the enzyme composition further comprises an *Aspergillus fumigatus* endoglucanase I. In another aspect, the enzyme composition further comprises an *Aspergillus fumigatus* endoglucanase II. In another aspect, the enzyme composition further comprises an *Aspergillus fumigatus* xylanase. In another aspect, the enzyme composition further comprises an *Aspergillus fumigatus* beta-xylosidase. In another aspect, the enzyme composition further comprises an *Aspergillus fumigatus* swollenin.

In another aspect, the enzyme composition further comprises a *Trichoderma* endoglucanase I. In another aspect, the enzyme composition further comprises a *Trichoderma reesei* endoglucanase I. In another aspect, the enzyme composition further comprises a *Trichoderma reesei* Cel7B endoglucanase I (GENBANK™ accession no. M15665). In another aspect, the *Trichoderma reesei* endoglucanase I is native to the host cell. In another aspect, the *Trichoderma reesei* endoglucanase I is the mature polypeptide of SEQ ID NO: 30.

In another aspect, the enzyme composition further comprises a *Trichoderma* endoglucanase II. In another aspect, the enzyme composition further comprises a *Trichoderma reesei* endoglucanase II. In another aspect, the enzyme composition further comprises a *Trichoderma reesei* Cel5A endoglucanase II (GENBANK™ accession no. M19373). In another aspect, the *Trichoderma reesei* endoglucanase II is native to the host cell. In another aspect, the *Trichoderma reesei* endoglucanase I is the mature polypeptide of SEQ ID NO: 32.

The enzyme composition may further comprise one or more (e.g., several) enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The enzyme(s) may be native or foreign to the *Trichoderma* host cell.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Uses

The present invention is also directed to the following processes for using an enzyme composition comprising a recovered fermentation broth of the present invention.

The present invention also relates to processes for degrading a cellulosic material, comprising: treating the cellulosic material with an enzyme composition comprising a recovered fermentation broth of the present invention. In one aspect, the processes further comprise recovering the degraded or converted cellulosic material. Soluble products of degradation or conversion of the cellulosic material can be separated from insoluble cellulosic material using a method known in the art such as, for example, centrifugation, filtration, or gravity settling.

The present invention also relates to processes of producing a fermentation product, comprising: (a) saccharifying a cellulosic material with an enzyme composition comprising a recovered fermentation broth of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition comprising a recovered fermentation broth of the present invention. In one aspect, the fermenting of the cellulosic material produces a fermentation product. In another aspect, the processes further comprise recovering the fermentation product from the fermentation.

The processes of the present invention can be used to saccharify the cellulosic material to fermentable sugars and to convert the fermentable sugars to many useful fermentation products, e.g., fuel, potable ethanol, and/or platform chemicals (e.g., acids, alcohols, ketones, gases, and the like). The production of a desired fermentation product from the cellulosic material typically involves pretreatment, enzymatic hydrolysis (saccharification), and fermentation.

The processing of the cellulosic material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include fluidized bed, upflow blanket, immobilized, and extruder type reactors for hydrolysis and/or fermentation.

Pretreatment.

In practicing the processes of the present invention, any pretreatment process known in the art can be used to disrupt plant cell wall components of the cellulosic material (Chandra et al., 2007, Substrate pretreatment: The key to effective enzymatic hydrolysis of lignocellulosics?, *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on temperature range and addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze explosion (AFEX), ammonia percolation (APR), ionic liquid, and organosolv pretreatments.

A catalyst such as $H_2SO_4$ or $SO_2$ (typically 0.3 to 5% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze explosion (AFEX).

Lime pretreatment is performed with calcium oxide or calcium hydroxide at temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. and Biotechnol. Vol.* 105-108, p. 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt % acid, e.g., 0.05 to 5 wt % acid or 0.1 to 2 wt % acid. The acid is contacted with the cellulosic material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material is present during pretreatment in amounts preferably between 10-80 wt %, e.g., 20-70 wt % or 30-60 wt %, such as around 40 wt %. The pretreated cellulosic material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperatures in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification.

In the hydrolysis step, also known as saccharification, the cellulosic material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition comprising a recovered fermentation broth of the present invention.

Enzymatic hydrolysis is preferably carried out in a suitable aqueous environment under conditions that can be readily determined by one skilled in the art. In one aspect, hydrolysis is performed under conditions suitable for the activity of the enzyme(s), i.e., optimal for the enzyme(s). The hydrolysis can be carried out as a fed batch or continuous process where the cellulosic material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 5.0 to about 5.5. The dry solids content is in the range of preferably about 5 to about 50 wt %, e.g., about 10 to about 40 wt % or about 20 to about 30 wt %.

In the processes of the present invention, the enzyme composition comprising a recovered fermentation broth of the present invention can be added prior to or during fermentation, e.g., during saccharification or during or after propagation of the fermenting microorganism(s).

The enzyme composition comprising a recovered fermentation broth of the present invention may be in any form suitable for use, such as, for example, a crude fermentation broth with or without cells removed, a cell lysate with or without cellular debris, a semi-purified or purified enzyme preparation, or a *Trichoderma* host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amount of *Aspergillus fumigatus* cellulases or hemicellulases depends on several factors including, but not limited to, the mixture of component cellulolytic and/or hemicellulolytic enzymes, the cellulosic material, the concentration of cellulosic material, the pretreatment(s) of the cellulosic material, temperature, time, pH, and inclusion of fermenting organism (e.g., yeast for Simultaneous Saccharification and Fermentation).

In one aspect, an effective amount of cellulolytic or hemicellulolytic enzyme to the cellulosic material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic material.

In another aspect, the GH61 polypeptide having cellulolytic enhancing activity is used in the presence of a soluble activating divalent metal cation according to WO 2008/151043, e.g., manganese sulfate.

In another aspect, a GH61 polypeptide having cellulolytic enhancing activity is used in the presence of a dioxy compound, a bicyclic compound, a heterocyclic compound, a nitrogen-containing compound, a quinone compound, a sulfur-containing compound, or a liquor obtained from a pretreated cellulosic material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1,2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of the bicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothienopyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid δ-lactone; 4-hydroxycoumarin; dihydrobenzofuran; 5-(hydroxymethyl) furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more (e.g., several) nitrogen atoms. In one aspect, the nitrogen-containing compound comprises an amine, imine, hydroxylamine, or nitroxide moiety. Non-limiting examples of the nitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of the quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more (e.g., several) sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound described above is about 0.1 µM to about 1 M, e.g., about 0.5 µM to about 0.75 M, about 0.75 µM to about 0.5 M, about 1 µM to about 0.25 M, about 1 µM to about 0.1 M, about 5 µM to about 50 mM, about 10 µM to about 25 mM, about 50 µM to about 25 mM, about 10 µM to about 10 mM, about 5 µM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

Fermentation.

The fermentable sugars obtained from the hydrolyzed cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Preferred yeast includes strains of *Candida, Kluyveromyces,* and *Saccharomyces,* e.g., *Candida sonorensis, Kluyveromyces marxianus,* and *Saccharomyces cerevisiae.*

Examples of fermenting organisms that can ferment pentose sugars in their native state include bacterial and fungal organisms, such as some yeast. Preferred xylose fermenting yeast include strains of *Candida*, preferably *C. sheatae* or *C. sonorensis*; and strains of *Pichia*, preferably *P. stipitis*, such as *P. stipitis* CBS 5773. Preferred pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum,* and *Zymomonas mobilis* (Philippidis, 1996, supra).

Other fermenting organisms include strains of *Bacillus,* such as *Bacillus coagulans; Candida,* such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis,* and *C. scehatae; Clostridium,* such as *C. acetobutylicum, C. thermocellum,* and *C. phytofermentans; E. coli,* especially *E. coli* strains that have been genetically modified to improve the yield of ethanol; *Geobacillus* sp.; *Hansenula,* such as *Hansenula anomala; Klebsiella,* such as *K. oxytoca; Kluyveromyces,* such as *K. marxianus, K. lactis, K. thermotolerans,* and *K. fragilis; Schizosaccharomyces,* such as *S. pombe; Thermoanaerobacter,* such as *Thermoanaerobacter saccharolyticum;* and *Zymomonas,* such as *Zymomonas mobilis.*

In a preferred aspect, the yeast is a *Bretannomyces*. In a more preferred aspect, the yeast is *Bretannomyces clausenii*. In another preferred aspect, the yeast is a *Candida*. In another more preferred aspect, the yeast is *Candida sonorensis*. In another more preferred aspect, the yeast is *Candida boidinii*. In another more preferred aspect, the yeast is *Candida* blankii. In another more preferred aspect, the yeast is *Candida brassicae*. In another more preferred aspect, the yeast is *Candida diddensii*. In another more preferred aspect, the yeast is *Candida entomophiliia*. In another more preferred aspect, the yeast is *Candida pseudotropicalis*. In another more preferred aspect, the yeast is *Candida sceha-* tae. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermotolerans*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Saccharomyces* spp. In another more preferred aspect, the yeast is *Saccharomyces cerevisiae*. In another more preferred aspect, the yeast is *Saccharomyces distaticus*. In another more preferred aspect, the yeast is *Saccharomyces uvarum*.

In a preferred aspect, the bacterium is a *Bacillus*. In a more preferred aspect, the bacterium is *Bacillus coagulans*. In another preferred aspect, the bacterium is a *Clostridium*. In another more preferred aspect, the bacterium is *Clostridium acetobutylicum*. In another more preferred aspect, the bacterium is *Clostridium phytofermentans*. In another more preferred aspect, the bacterium is *Clostridium thermocellum*. In another more preferred aspect, the bacterium is *Geobacillus* sp. In another more preferred aspect, the bacterium is a *Thermoanaerobacter*. In another more preferred aspect, the bacterium is *Thermoanaerobacter saccharolyticum*. In another preferred aspect, the bacterium is a *Zymomonas*. In another more preferred aspect, the bacterium is *Zymomonas mobilis*.

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae*, *Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae*, *Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli*, *Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis, Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis*.

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more (e.g., several) hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

In another preferred aspect, the fermentation product is isoprene.

In another preferred aspect, the fermentation product is a ketone. It will be understood that the term "ketone" encompasses a substance that contains one or more (e.g., several) ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

The present invention is further described by the following examples that should not be construed as limiting the scope of the invention.

EXAMPLES

Strains

*Trichoderma reesei* strain 981-O-8 (D4) is a mutagenized strain of *Trichoderma reesei* RutC30 (ATCC 56765; Montenecourt and Eveleigh, 1979, *Adv. Chem. Ser.* 181: 289-301).

*Trichoderma reesei* strain AgJg115-104-7B1 (PCT/US2010/061105, WO 2011/075677) is a ku70− derivative of *T. reesei* strain 981-O-8 (D4).

Media and Buffer Solutions

2XYT plus ampicillin plates were composed of 16 g of tryptone, 10 g of yeast extract, 5 g of sodium chloride, 15 g of Bacto agar, and deionized water to 1 liter. One ml of a 100 mg/ml solution of ampicillin was added after the autoclaved medium was cooled to 55° C.

SOC medium was composed of 20 g of Bacto-tryptone, 5 g of Bacto yeast extract, 0.5 g of NaCl, 2.5 ml of 1 M KCl, and deionized water to 1 liter. The pH was adjusted to 7.0 with 10 N NaOH before autoclaving. Then 20 ml of sterile 1 M glucose was added immediately before use.

LB plates were composed of 10 g of tryptone, 5 g of yeast extract, 5 g of NaCl, 15 g of Bacto agar, and deionized water to 1 liter.

COVE salt solution was composed of 26 g of KCl, 26 g of $MgSO_4.7H_2O$, 76 g of $KH_2PO_4$, 50 ml of COVE trace metals solution, and deionized water to 1 liter.

COVE trace metals solution was composed of 0.04 g of $NaB_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, 10 g of $ZnSO_4.7H_2O$, and deionized water to 1 liter.

COVE plates were composed of 342.3 g of sucrose, 20 ml of COVE salt solution, 10 ml of 1 M acetamide, 10 ml of 1.5 M CsCl, 25 g of Noble agar (Difco), and deionized water to 1 liter.

COVE2 plates were composed of 30 g of sucrose, 20 ml of COVE salt solution, 10 ml of 1 M acetamide, 25 g of Noble agar (Difco), and deionized water to 1 liter.

*Trichoderma* trace metals solution was composed of 216 g of $FeCl_3.6H_2O$, 58 g of $ZnSO_4.7H_2O$, 27 g of $MnSO_4.H_2O$, 10 g of $CuSO_4.5H_2O$, 2.4 g of $H_3BO_3$, 336 g of citric acid, and deionized water to 1 liter.

CIM medium was composed of 20 g of cellulose, 10 g of corn steep solids, 1.45 g of $(NH_4)_2SO_4$, 2.08 g of $KH_2PO_4$, 0.28 g of $CaCl_2$, 0.42 g of $MgSO_4.7H_2O$, 0.42 ml of *Trichoderma* trace metals solution, 1-2 drops of antifoam, and deionized water to 1 liter; pH adjusted to 6.0.

YP medium was composed of 10 g of yeast extract, 20 g of Bacto peptone, and deionized water to 1 liter.

YPG medium was composed of 4 g of yeast extract, 1 g of $K_2HPO_4$, 0.5 g of $MgSO_4$, 15.0 g of glucose, and deionized water to 1 liter (pH 6.0).

PEG buffer was composed of 500 g of polyethylene glycol 4000 (PEG 4000), 10 mM $CaCl_2$, 10 mM Tris-HCl pH 7.5, and deionized water to 1 liter; filter sterilized.

PDA plates were composed of 39 g of Potato Dextrose Agar (Difco) and deionized water to 1 liter.

PDA overlay medium was composed of 39 g of Potato Dextrose Agar (Difco), 2.44 g of uridine, and deionized water to 1 liter. The previously autoclaved medium was melted in a microwave and then cooled to 55° C. before use.

STC was composed of 1 M sorbitol, 10 mM $CaCl_2$, and 10 mM Tris-HCl, pH 7.5; filter sterilized.

TE buffer was composed of 1 M Tris pH 8.0 and 0.5 M EDTA pH 8.0.

20×SSC was composed of 175.3 g of NaCl, 88.2 g of sodium citrate, and deionized water to 1 liter.

TrMM-G medium was composed of 20 ml of COVE salt solution, 6 g of $(NH_4)_2SO_4$, 0.6 g of $CaCl_2$, 25 g of Nobel agar (Difco), 20 g of glucose, and deionized water to 1 liter.

NZY+ medium was composed of 5 g of NaCl, 3 g of $MgSO_4.7H_2O$, 5 g of yeast extract, 10 g of NZ amine, 1.2 g of $MgCl_2$, 4 g of glucose, and deionized water to 1 liter.

NNCYP07-PCS medium was composed of 5.0 g of $NaNO_3$, 3.0 g of $NH_4Cl$, 2.0 g of MES (free acid), 2.5 g of citric acid, 0.2 g of $CaCl_2$ $2H_2O$, 1.0 g of Bacto Peptone, 5.0 g of yeast extract, 0.2 g of $MgSO_4$ $7H_2O$, 4.0 g of $K_2HPO_4$, 1.0 ml of COVE trace metals solution, 80.0 g of pretreated corn stover (PCS), and deionized water to 1 liter.

Example 1: Construction of a *Trichoderma reesei* cbh1-*Aspergillus fumigatus* cbh1 Replacement Construct pJfyS139

The *Aspergillus fumigatus* cellobiohydrolase I (cbh1) coding sequence (SEQ ID NO: 1 [DNA sequence] and SEQ ID NO: 2 [deduced amino acid sequence]) was amplified from pEJG93 (WO 2011/057140) using the gene-specific forward and reverse primers shown below. The region in italics represents vector homology to the site of insertion for an IN-FUSION® reaction and the underlined portion is an introduced Pac I site.

```
Forward primer:
                                    (SEQ ID NO: 43)
5'-cgcggactgcgcaccATGCTGGCCTCCACCTTCTCCTACC-3'

Reverse primer:
                                    (SEQ ID NO: 44)
5'-ctttcgccacggagcttaattaaCTACAGGCACTGAGAGTAAT
AATCA-3'
```

The amplification reaction was composed of 20 ng of pEJG93, 200 μM dNTP's, 0.4 μM primers, 1× HERCULASE® Reaction Buffer (Stratagene, La Jolla, Calif., USA), and 1.875 units of HERCULASE® Hot Start High-Fidelity DNA Polymerase (Stratagene, La Jolla, Calif., USA) in a final volume of 50 μl. The amplification reaction was incubated in an EPPENDORF® MASTERCYCLER® 5333 epgradient S (Eppendorf Scientific, Inc., Westbury, N.Y., USA) programmed for 1 cycle at 95° C. for 2 minutes; 30 cycles each at 95° C. for 30 seconds, 55° C. for 30 seconds, and 72° C. for 1 minute; and 1 cycle at 72° C. for 7 minutes. The PCR products were separated by 1% agarose gel electrophoresis using 40 mM Tris base, 20 mM sodium acetate, 1 mM disodium EDTA (TAE) buffer where a 1.6 kb fragment was excised from the gel and extracted using a MINELUTE® Gel Extraction Kit (QIAGEN Inc., Valencia, Calif., USA) according to the manufacturer's protocol.

The 1.6 kb PCR product was inserted into Nco I/Pac I-digested pSMai155 (WO 05/074647) using an IN-FUSION® Advantage PCR Cloning Kit (Clontech, Palo Alto, Calif., USA) according to the manufacturer's protocol. The IN-FUSION® reaction was composed of 1× IN-FUSION® Reaction Buffer (Clontech, Palo Alto, Calif., USA), 125 ng of Nco I/Pac I-digested pSMai155, 100 ng of the 1.6 kb PCR product, and 1 µl of IN-FUSION® Enzyme (Clontech, Palo Alto, Calif., USA) in a 10 µl reaction volume. The reaction was incubated for 15 minutes at 37° C. followed by 15 minutes at 50° C. After the incubation period 40 µl of TE buffer were added to the reaction. A 2 µl aliquot was used to transform ONE SHOT® TOP10 competent cells (Invitrogen, Carlsbad, Calif., USA) according to the manufacturer's protocol. The cells were heat shocked at 42° C. for 30 seconds and 250 µl of SOC medium were added. The tubes were incubated at 37° C., 200 rpm for 1 hour and 250 µl were plated onto 150 mm diameter 2XYT plus ampicillin plates and incubated at 37° C. overnight. The resulting transformants were screened by sequencing and one clone containing the insert with no PCR errors was identified and designated pJfyS139-A. Plasmid pJfyS139-A was used for insertion of the Herpes simplex virus thymidine kinase (tk) gene.

The Herpes simplex virus tk coding sequence (SEQ ID NO: 45 [DNA sequence] and SEQ ID NO: 46 [deduced amino acid sequence]) was liberated from pJfyS1579-8-6 (WO 2010/039840) by digesting the plasmid with Bgl II and Bam HI. The digestion was subjected to 1% agarose gel electrophoresis using TAE buffer where a 2.3 kb band was excised from the gel and extracted using a MINELUTE® Gel Extraction Kit. The tk gene cassette was inserted into Bam HI-digested, calf intestine phosphatase-treated pJfyS139-A using a QUICK LIGATION™ Kit (New England Biolabs, Inc., Ipswich, Mass. USA) according to the manufacturer's protocol. The ligation reaction was composed of 50 ng of the Bam HI-digested, calf intestine phosphatase-treated pJfyS139-A, 50 ng of the 2.3 kb tk gene insert, 1× QUICK LIGATION™ Buffer (New England Biolabs, Inc., Ipswich, Mass. USA), and 5 units of QUICK LIGASE™ (New England Biolabs, Inc., Ipswich, Mass. USA) in a final volume of 20 µl. The reaction was incubated at room temperature for 5 minutes and 2 µl of the reaction were used to transform ONE SHOT® TOP10 competent cells according to the manufacturer's protocol. The cells were heat shocked at 42° C. for 30 seconds and 250 µl of SOC medium were added. The tubes were incubated at 37° C., 200 rpm for 1 hour and 250 µl were plated onto 150 mm diameter 2XYT plus ampicillin plates and incubated at 37° C. overnight. The resulting transformants were screened by restriction digestion analysis with Xma I to determine the presence and orientation of the insert and a clone containing the insert was identified and designated pJfyS139-B. Plasmid pJfyS139-B was used for insertion of a *T. reesei* 3' cbh1 gene flanking sequence.

The 3' cbh1 gene flanking sequence was amplified from *T. reesei* RutC30 genomic DNA using the forward and reverse primers below. The underlined portion represents an introduced Not I site for cloning.

```
Forward Primer:
                                    (SEQ ID NO: 47)
5'-ttagactgcggccgcGTGGCGAAAGCCTGACGCACCGGTAGAT-3'

Reverse Primer:
                                    (SEQ ID NO: 48)
5'-agtagttagcggccgcACGGCACGGTTAAGCAGGGTCTTGC-3'
```

*Trichoderma reesei* RutC30 was grown in 50 ml of YP medium supplemented with 2% glucose (w/v) in a 250 ml baffled shake flask at 28° C. for 2 days with agitation at 200 rpm. Mycelia were harvested by filtration using MIRACLOTH® (Calbiochem, La Jolla, Calif., USA), washed twice in deionized water, and frozen under liquid nitrogen. Frozen mycelia were ground by mortar and pestle to a fine powder. Total DNA was isolated using a DNEASY® Plant Maxi Kit (QIAGEN Inc., Valencia, Calif., USA) with the lytic incubation extended to 2 hours.

The amplification reaction was composed of 150 ng of *T. reesei* RutC30 genomic DNA, 200 µM dNTP's, 0.4 µM primers, 1× HERCULASE® Reaction Buffer, and 1.875 units of HERCULASE® Hot Start High-Fidelity DNA Polymerase in a final volume of 50 µl. The amplification reaction was incubated in an EPPENDORF® MASTERCYCLER® 5333 epgradient S programmed for 1 cycle at 95° C. for 2 minutes; 30 cycles each at 95° C. for 30 seconds, 60° C. for 30 seconds, and 72° C. for 1 minute 30 seconds; and 1 cycle at 72° C. for 7 minutes.

The PCR reaction was subjected to a MINELUTE® Nucleotide Removal Kit (QIAGEN Inc., Valencia, Calif., USA) according to the manufacturer's protocol. The resulting PCR mixture was digested with Not I and the digested PCR products were separated by 1% agarose gel electrophoresis using TAE buffer. A 1.3 kb fragment containing the 3' cbh1 gene flanking sequence was excised from the gel and extracted using a MINELUTE® Gel Extraction Kit. The 1.3 kb fragment was inserted into Not I-linearized, calf intestine phosphatase-treated pJfyS139-B using a QUICK LIGATION™ Kit. The QUICK LIGATION™ reaction was composed of 100 ng of the Not I-linearized, calf intestine phosphatase-treated pJfyS139-B, 20 ng of the 1.3 kb fragment, 1× QUICK LIGATION™ Buffer, and 5 units of QUICK LIGASE™ in a final volume of 20 µl. The reaction was incubated at room temperature for 5 minutes and 2 µl of the reaction was used to transform ONE SHOT® TOP10 competent cells according to the manufacturer's protocol. The cells were heat shocked at 42° C. for 30 seconds and 250 µl of SOC medium were added. The tubes were incubated at 37° C., 200 rpm for 1 hour and 250 µl were plated onto 150 mm diameter 2XYT plus ampicillin plates and incubated at 37° C. overnight. The resulting transformants were screened by restriction digestion analysis with Xma I to determine the presence and orientation of the insert and positive clones were sequenced. A clone containing the 3' cbh1 gene flanking sequence with no PCR errors was designated pJfyS139 (FIG. 1). Plasmid pJfyS139 was used as the vector to replace the *T. reesei* cbh1 gene.

Example 2: *Trichoderma reesei* Protoplast Generation and Transformation

Protoplast preparation and transformation were performed using a modified protocol by Penttila et al., 1987, *Gene* 61: 155-164. Briefly, *Trichoderma reesei* strain AgJg115-104-7B1 (PCT/US2010/061105, WO 2011/075677) was cultivated in 25 ml of YP medium supplemented with 2% (w/v) glucose and 10 mM uridine at 27° C. for 17 hours with gentle agitation at 90 rpm. Mycelia were collected by filtration using a Vacuum Driven Disposable Filtration System (Millipore, Bedford, Mass., USA) and washed twice with deionized water and twice with 1.2 M sorbitol. Protoplasts were generated by suspending the washed mycelia in 20 ml of 1.2 M sorbitol containing 15 mg of GLUCANEX® 200 G (Novozymes A/S, Bagsvaerd, Denmark) per ml and 0.36 units of chitinase (Sigma Chemical Co., St. Louis, Mo., USA) per ml for 15-25 minutes at 34° C. with gentle shaking at 90 rpm. Protoplasts were collected by centrifuging for 7 minutes at 400×g and washed twice with cold 1.2 M sorbitol. The protoplasts were counted using a haemocytometer and re-suspended to a final concentration of 1×10⁸ protoplasts per ml in STC. Excess protoplasts were stored in a Cryo 1° C. Freezing Container (Nalgene, Rochester, N.Y., USA) at −80° C.

Approximately 100 μg of a transforming plasmid described in the following Examples were digested with Pme I. The digestion reaction was purified by 1% agarose gel electrophoresis using TAE buffer. A DNA band was excised from the gel and extracted using a QIAQUICK® Gel Extraction Kit (QIAGEN Inc., Valencia, Calif., USA). The resulting purified DNA was added to 100 μl of the protoplast solution and mixed gently. PEG buffer (250 μl) was added, mixed, and incubated at 34° C. for 30 minutes. STC (3 ml) was then added, mixed, and spread onto PDA plates supplemented with 1 M sucrose. After incubation at 28° C. for 16 hours, 20 ml of an overlay PDA medium supplemented with 35 μg of hygromycin B per ml were added to each plate. The plates were incubated at 28° C. for 4-7 days.

Example 3: Replacement of the Native *Trichoderma reesei* cbh1 Gene with the *Aspergillus fumigatus* cbh1 Coding Sequence In order to replace the *Trichoderma reesei* native cbh1 gene (SEQ ID NO: 23 [DNA sequence] and SEQ ID NO: 24 [deduced amino acid sequence]) with the *Aspergillus fumigatus* cbh1 coding sequence (SEQ ID NO: 1 [DNA sequence] and SEQ ID NO: 2 [deduced amino acid sequence]), *Trichoderma reesei* ku70− strain AgJg115-104-7B1 (PCT/US2010/061105, WO 2011/075677) was transformed with 4×2 μg of Pme I-linearized pJfyS139 (Example 1) according to the procedure described in Example 2. Seven transformants were obtained and each one was picked and transferred to a PDA plate and incubated for 7 days at 28° C. Genomic DNA was isolated from the transformants according to the procedure described in Example 1 and each transformant submitted to Southern analysis.

For Southern analysis, 2 μg of genomic DNA was digested with 33 units of Bgl II in a 50 μl reaction volume and subjected to 1% agarose electrophoresis in TAE buffer. The DNA in the gel was depurinated with one 10 minute wash in 0.25 N HCl, denatured with two 15 minute washes in 0.5 N NaOH-1.5 M NaCl, neutralized with one 30 minute wash in 1 M Tris pH 8-1.5 M NaCl, and incubated in 20×SSC for 5 minutes. The DNA was transferred to a NYTRAN® Supercharge membrane (Whatman, Inc., Florham Park, N.J., USA) using a TURBOBLOTTER™ System (Whatman, Inc., Florham Park, N.J., USA) according to the manufacturer's protocol. The DNA was UV crosslinked to the membrane using a STRATALINKER™ UV Crosslinker (Stratagene, La Jolla, Calif., USA) and prehybridized for 1 hour at 42° C. in 20 ml of DIG Easy Hyb (Roche Diagnostics Corporation, Indianapolis, Ind., USA).

A probe hybridizing to the 3' cbh1 gene flanking sequence was generated using a PCR Dig Probe Synthesis Kit (Roche Diagnostics Corporation, Indianapolis, Ind., USA) according to the manufacturer's instructions with the forward and reverse primers shown below. The PCR reaction was composed of 1× HERCULASE® Reaction Buffer, 400 nM of each primer, 200 μM DIG-labeled dUTP-containing dNTPs, 20 ng of pJfyS139, and 1.5 units of HERCULASE® Hot Start High-Fidelity DNA Polymerase. The amplification reaction was incubated in an EPPENDORF® MASTERCYCLER® 5333 epgradient S programmed for 1 cycle at 95° C. for 2 minutes; 25 cycles each at 95° C. for 30 seconds, 55° C. for 30 seconds, and 72° C. for 40 seconds; and 1 cycle at 72° C. for 7 minutes.

```
Forward primer:
                                      (SEQ ID NO: 49)
5'-AAAAAACAAACATCCCGTTCATAAC-3'

Reverse primer:
                                      (SEQ ID NO: 50)
5'-AACAAGGTTTACCGGTTTCGAAAAG-3'
```

The probe was purified by 1% agarose gel electrophoresis using TAE buffer where a 0.5 kb band corresponding to the probe was excised from the gel and extracted using a MINELUTE® Gel Extraction Kit. The probe was boiled for 5 minutes, chilled on ice for 2 minutes, and added to 10 ml of DIG Easy Hyb to produce the hybridization solution. Hybridization was performed at 42° C. for 15-17 hours. The membrane was then washed under low stringency conditions in 2×SSC plus 0.1% SDS for 5 minutes at room temperature followed by two high stringency washes in 0.5×SSC plus 0.1% SDS for 15 minutes each at 65° C. The probe-target hybrids were detected by chemiluminescent assay (Roche Diagnostics, Indianapolis, Ind., USA) according to the manufacturer's instructions. Southern analysis indicated that 3 of the 7 transformants contained the replacement cassette at the cbh1 locus and one transformant, *T. reesei* JfyS139-8, was chosen for curing the hpt and tk markers.

A fresh plate of spores was generated by transferring spores of a 7 day old PDA plate grown at 28° C. to a PDA plate and incubating for 7 days at 28° C. Spores were collected in 10 ml of 0.01% TWEEN® 20 using a sterile spreader. The concentration of spores was determined using a hemocytometer and 10⁵ spores were spread onto 150 mm plates containing TrMM-G medium supplemented with 1 μM 5-fluoro-2'-deoxyuridine (FdU).

Three hundred FdU-resistant spore isolates were obtained and DNA was extracted from 2 of the spore isolates as described above. The isolates were analyzed by Southern analysis as described above and the results indicated that both spore isolates had excised the hpt/tk region between the homologous repeats of the replacement cassette. One strain designated *T. reesei* JfyS139-8A was chosen for replacing the cbhII gene.

Example 4: Construction of an Empty *Trichoderma reesei* cbhII Replacement Construct pJfyS142

To generate a construct to replace the *Trichoderma reesei* cbhII gene (SEQ ID NO: 25 [DNA sequence] and SEQ ID NO: 26 [deduced amino acid sequence]) with the *Aspergillus fumigatus* cbhII coding sequence (SEQ ID NO: 3 [DNA sequence] and SEQ ID NO: 4 [deduced amino acid sequence]), the *T. reesei* cbhII promoter was first amplified from *T. reesei* RutC30 genomic DNA using the gene-specific forward and reverse primers shown below. The region in italics represents vector homology to the site of insertion in an IN-FUSION® reaction. *T. reesei* RutC30 genomic DNA was prepared according to the procedure described in Example

```
Forward primer:
                                      (SEQ ID NO: 51)
5'-acgaattgtttaaacgtcgacCCAAGTATCCAGAGGTGTATGGAAAT
ATCAGAT-3'

Reverse primer:
                                      (SEQ ID NO: 52)
5'-cgcgtagatctgcggccatGGTGCAATACACAGAGGGTGATCTT-3'
```

The amplification reaction was composed of 20 ng of *T. reesei* RutC30 genomic DNA, 200 μM dNTP's, 0.4 μM primers, 1× HERCULASE® Reaction Buffer, and 1.875 units of HERCULASE® Hot Start High-Fidelity DNA Polymerase in a final volume of 50 μl. The amplification reaction was incubated in an EPPENDORF® MASTERCYCLER® programmed for 1 cycle at 95° C. for 2 minutes; 25 cycles each at 95° C. for 30 seconds, 55° C. for 30 seconds, and 72° C. for 1 minute 30 seconds; and 1 cycle at 72° C. for 7 minutes. The PCR products were separated by 1% agarose gel electrophoresis using TAE buffer where a 1.6 kb fragment was excised from the gel and extracted using a MINELUTE® Gel Extraction Kit.

The 1.6 kb PCR product was inserted into Nco I/Sal I-digested pSMai155 (WO 05/074647) using an IN-FUSION® Advantage PCR Cloning Kit according to the manufacturer's protocol. The IN-FUSION® reaction was composed of 1× IN-FUSION® Reaction Buffer, 125 ng of the Nco I/Sal I-digested pSMai155, 100 ng of the 1.6 kb PCR product, and 1 μl of IN-FUSION® Enzyme in a 10 μl reaction volume. The reaction was incubated for 15 minutes at 37° C. and 15 minutes at 50° C. After the incubation period 40 μl of TE were added to the reaction. A 2 μl aliquot was used to transform ONE SHOT® TOP10 competent cells according to the manufacturer's protocol. The cells were heat shocked at 42° C. for 30 seconds and 250 μl of SOC medium were added. The tubes were incubated at 37° C., 200 rpm for 1 hour and 250 μl were plated onto 150 mm diameter 2XYT plus ampicillin plates and incubated at 37° C. overnight. The resulting transformants were screened by restriction digestion analysis with Pci I and positive clones sequenced to ensure the absence of PCR errors. One clone containing the insert with no PCR errors was identified and designated pJfyS142-A. Plasmid pJfyS142-A was used to insert the *T. reesei* cbhII terminator.

The cbhII terminator was amplified from *T. reesei* RutC30 genomic DNA using the gene-specific forward and reverse primers shown below. The region in italics represents vector homology to the site of insertion in an IN-FUSION® reaction.

```
Forward primer:
                            (SEQ ID NO: 53)
5'-atctacgcgtactagttaattaaGGCTTTCGTGACCGGGCTTCAA

ACA-3'

Reverse primer:
                            (SEQ ID NO: 54)
5'-gcggccgttactagtggatccACTCGGAGTTGTTATACGCTAC

TCG-3'
```

The amplification reaction was composed of 150 ng of *T. reesei* RutC30 genomic DNA, 200 μM dNTP's, 0.4 μM primers, 1× HERCULASE® Reaction Buffer, and 1.875 units of HERCULASE® Hot Start High-Fidelity DNA Polymerase in a final volume of 50 μl. The amplification reaction was incubated in an EPPENDORF® MASTERCYCLER® programmed for 1 cycle at 95° C. for 2 minutes; 25 cycles each at 95° C. for 30 seconds, 54° C. for 30 seconds, and 72° C. for 50 seconds; and 1 cycle at 72° C. for 7 minutes. PCR products were separated by 1% agarose gel electrophoresis using TAE buffer where a 0.3 kb fragment was excised from the gel and extracted using a MINELUTE® Gel Extraction Kit.

The 0.3 kb PCR product was inserted into Pac I/Bam HI-digested pJfyS142-A using an IN-FUSION® Advantage PCR Cloning Kit according to the manufacturer's protocol. The IN-FUSION® reaction was composed of 1× IN-FUSION® Reaction Buffer, 150 ng of the PacI/Bam HI-digested pJfyS142-A, 50 ng of the 0.3 kb PCR product, and 1 μl of IN-FUSION® Enzyme in a 10 μl reaction volume. The reaction was incubated for 15 minutes at 37° C. and 15 minutes at 50° C. After the incubation period 40 μl of TE were added to the reaction. A 2 μl aliquot was used to transform ONE SHOT® TOP10 competent cells according to the manufacturer's protocol. The cells were heat shocked at 42° C. for 30 seconds and 250 μl of SOC medium were added. The tubes were incubated at 37° C., 200 rpm for 1 hour and 250 μl were plated onto 150 mm diameter 2XYT plus ampicillin plates and incubated at 37° C. overnight. The transformants were screened by sequence analysis to identify positive clones and to ensure the absence of PCR errors. One clone containing the insert with no PCR errors was identified and designated pJfyS142-B. Plasmid pJfyS142-B was used for insertion of the Herpes simplex tk gene.

The Herpes simplex tk gene was liberated from pJfyS1579-8-6 (WO 2010/039840) by digesting the plasmid with Bgl II and Bam HI. The digestion was submitted to 1% agarose gel electrophoresis using TAE buffer where a 2.3 kb band was excised from the gel and extracted using a MINELUTE® Gel Extraction Kit. The tk cassette was inserted into Bam HI-digested, calf Intestine phosphatase-dephosphorylated pJfyS142-B using a QUICK LIGATION™ Kit according to the manufacturer's protocol. The ligation reaction was composed of 50 ng of the Bam HI-digested, calf Intestine phosphatase-dephosphorylated pJfyS142-B, 50 ng of the 2.3 kb tk gene insert, 1× QUICK LIGATION™ Buffer, and 5 units of QUICK LIGASE™ in a 20 μl ligation volume. The reaction was incubated at room temperature for 5 minutes and 2 μl of the reaction was used to transform ONE SHOT® TOP10 competent cells according to the manufacturer's protocol. The cells were heat shocked at 42° C. for 30 seconds and 250 μl of SOC medium were added. The tubes were incubated at 37° C., 200 rpm for 1 hour and 250 μl were plated onto 150 mm diameter 2XYT plus ampicillin plates and incubated at 37° C. overnight. The resulting transformants were screened by restriction digestion analysis with Xma I and Bam HI to determine the presence and orientation of the insert and a clone containing the insert was identified and designated pJfyS142-C. Plasmid pJfyS142-C was used for insertion of the *T. reesei* 3' cbhII gene flanking sequence.

The 3' cbhII gene flanking sequence was amplified from *T. reesei* RutC30 genomic DNA using the forward and reverse primers shown below. The region in italics represents vector homology to the site of insertion in an IN-FUSION® reaction.

```
Forward primer:
                            (SEQ ID NO: 55)
5'-atccatcacactggcggccgcGCTTCAAACAATGATGTGCGAT

GGT-3'

Reverse primer:
                            (SEQ ID NO: 56)
5'-gatgcatgctcgagcggccgcCTACCTTGGCAGCCCTACGAGA

GAG-3'
```

Figure 2:
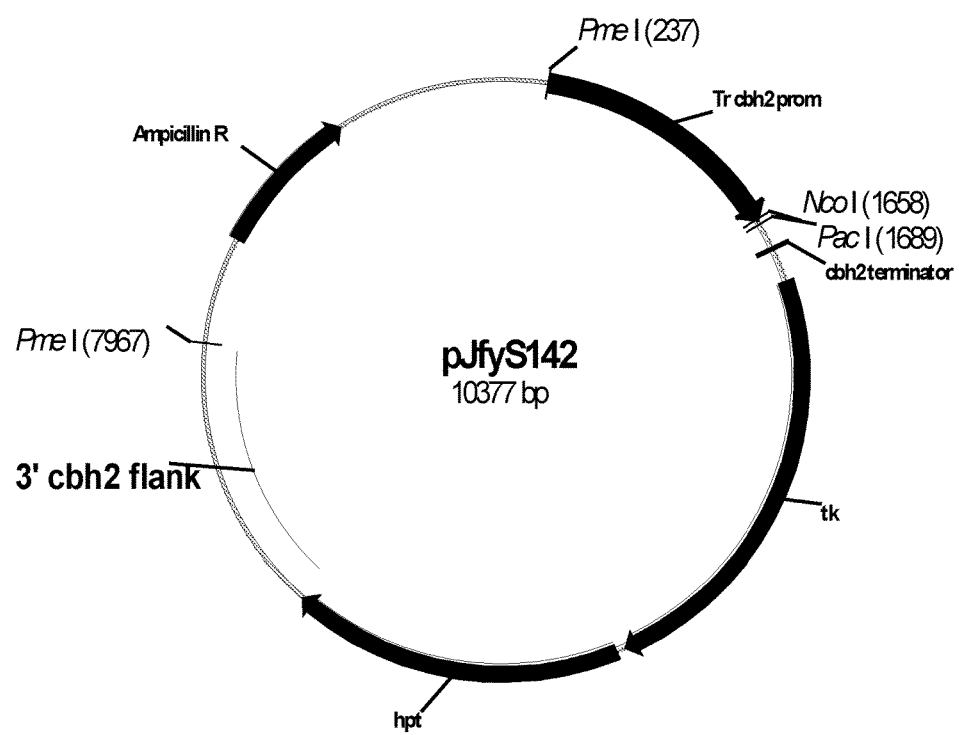
FIG. 2 shows a restriction map of plasmid pJfyS142.

The amplification reaction was composed of 150 ng of *T. reesei* RutC30 genomic DNA, 200 μM dNTP's, 0.4 μM primers, 1× HERCULASE® Reaction Buffer, and 1.875 units of HERCULASE® Hot Start High-Fidelity DNA Polymerase in a final volume of 50 μl. The amplification reaction was incubated in an EPPENDORF® MASTERCYCLER® programmed for 1 cycle at 95° C. for 2 minutes; 30 cycles each at 95° C. for 30 seconds, 56° C. for 30 seconds, and 72° C. for 1 minute 50 seconds; and 1 cycle at 72° C. for 7 minutes. The PCR reaction was subjected to 1% agarose gel electrophoresis using TAE buffer where a 1.5 kb band was excised from the gel and extracted using a MIN-ELUTE® Gel Extraction Kit. The 3' cbhll gene flanking sequence was inserted into Not I-linearized pJfyS142-C using an IN-FUSION® Advantage PCR Cloning Kit according to the manufacturer's protocol. The IN-FUSION® reaction was composed of 1× IN-FUSION® Reaction Buffer, 150 ng of pJfyS142-C, 80 ng of the 1.5 kb PCR product, and 1 µl of IN-FUSION® Enzyme in a 10 µl reaction volume. The reaction was incubated for 15 minutes at 37° C. and 15 minutes at 50° C. After the incubation period 40 µl of TE were added to the reaction. A 2 µl aliquot was used to transform ONE SHOT® TOP10 competent cells according to the manufacturer's protocol. The cells were heat shocked at 42° C. for 30 seconds and 250 µl of SOC medium were added. The tubes were incubated at 37° C., 200 rpm for 1 hour and 250 µl were plated onto 150 mm diameter 2XYT plus ampicillin plates and incubated at 37° C. overnight. The resulting transformants were screened by restriction digestion analysis with Bgl II and positive clones were sequenced to ensure the absence of PCR errors. One clone containing the insert with no PCR errors was identified and designated pJfyS142 (FIG. 2). Plasmid pJfyS142 was used to insert the *A. fumigatus* cbhll coding sequence.

Example 5: Construction of a *Trichoderma reesei* cbhll-*Aspergillus fumigatus* cbhll Replacement Construct pJfyS144

The *Aspergillus fumigatus* cbhll coding sequence (SEQ ID NO: 3 [DNA sequence] and SEQ ID NO: 4 [deduced amino acid sequence]) was amplified from pAILo33 (WO 2011/057140) using the forward and reverse primers shown below. The region in italics represents vector homology to the site of insertion for an IN-FUSION® reaction.

```
Forward primer:
                                          (SEQ ID NO: 57)
5'-ctctgtgtattgcaccATGAAGCACCTTGCATCTTCCATCG-3'

Reverse primer:
                                          (SEQ ID NO: 58)
5'-ccggtcacgaaagccTTAATTAAAAGGACGGGTTAGCGTT-3'
```

The amplification reaction was composed of 20 ng of pAILo33, 200 µM dNTP's, 0.4 µM primers, 1 mM HERCULASE® Reaction Buffer, and 1.875 units of HERCULASE® Hot Start High-Fidelity DNA Polymerase in a final volume of 50 µl. The amplification reaction was incubated in an EPPENDORF® MASTERCYCLER® programmed for 1 cycle at 95° C. for 2 minutes; 30 cycles each at 95° C. for 30 seconds, 55° C. for 30 seconds, and 72° C. for 2 minutes; and 1 cycle at 72° C. for 7 minutes.

Figure 3:
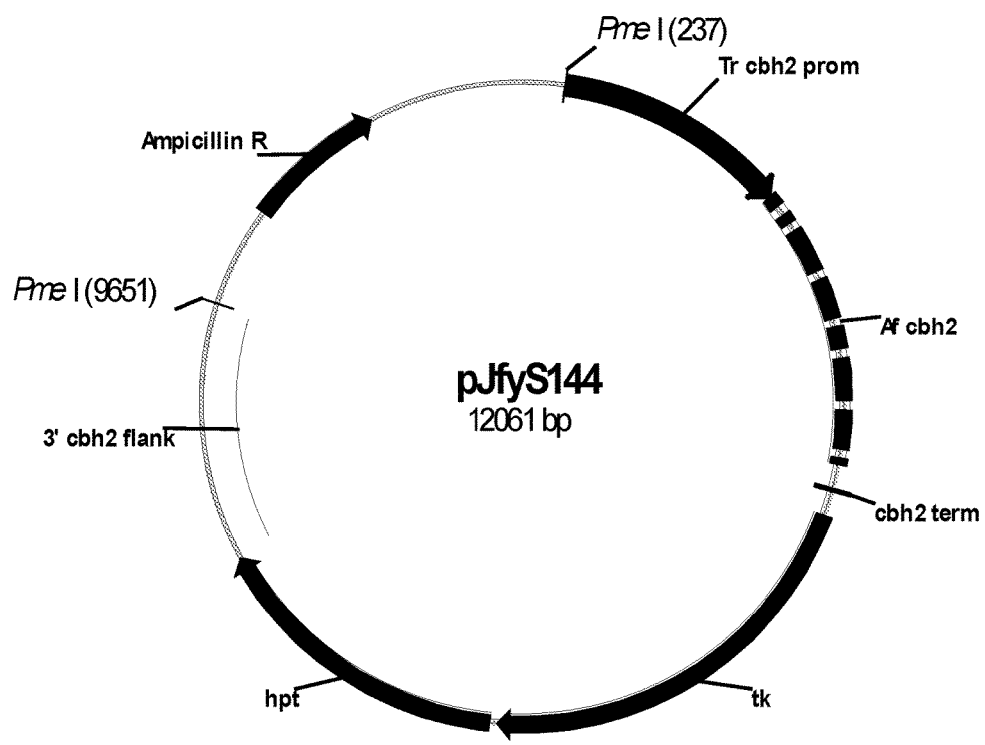
FIG. 3 shows a restriction map of plasmid pJfyS144.

The PCR reaction was subjected to 1% agarose gel electrophoresis using TAE buffer where a 1.7 kb band was excised from the gel and extracted using a MINELUTE® Gel Extraction Kit. The 1.7 kb PCR product was inserted into Nco I/Pac I-digested pJfyS142 (Example 4) using an IN-FUSION® Advantage PCR Cloning Kit according to the manufacturer's protocol. The IN-FUSION® reaction was composed of 1× IN-FUSION® Reaction Buffer, 120 ng of the Nco II Pac I-digested pJfyS142, 70 ng of the 1.7 kb PCR product, and 1 µl of IN-FUSION® Enzyme in a 10 µl reaction volume. The reaction was incubated for 15 minutes at 37° C. and 15 minutes at 50° C. After the incubation period 40 µl of TE were added to the reaction. A 2 µl aliquot was used to transform ONE SHOT® TOP10 competent cells according to the manufacturer's protocol. The cells were heat shocked at 42° C. for 30 seconds and 250 µl of SOC medium were added. The tubes were incubated at 37° C., 200 rpm for 1 hour and 250 µl were plated onto 150 mm diameter 2XYT plus ampicillin plates and incubated at 37° C. overnight. The resulting transformants were sequenced to ensure the absence of PCR errors and determine the presence of the insert. One clone with error-free sequence was identified and designated pJfyS144 (FIG. 3). Plasmid pJfyS144 was used to replace the native cbhll gene with the cbhll coding sequence from *A. fumigatus*.

Example 6: Replacement of the Native *Trichoderma reesei* cbhll Gene with the *Aspergillus fumigatus* cbhll Coding Sequence In order to replace the native *T. reesei* cbhll gene (SEQ ID NO: 25 [DNA sequence] and SEQ ID NO: 26 [deduced amino acid sequence]) with the *Aspergillus fumigatus* cbhll coding sequence (SEQ ID NO: 3 [DNA sequence] and SEQ ID NO: 4 [deduced amino acid sequence]), *Trichoderma reesei* JfyS139-8A (Example 3) was transformed according to the procedure described in Example 2 with 2 µg of Pme I-linearized and gel purified pJfyS144 (Example 5). Seven transformants were obtained and each one was picked and transferred to a PDA plate and incubated for 7 days at 28° C. A fungal spore PCR method described below was used to screen for transformants bearing gene replacement using the forward primer shown below annealing to a region upstream of the 5' cbhll gene flanking sequence beyond the region of integration, and the reverse primer shown below annealing in the *A. fumigatus* cbhll coding sequence.

```
Forward primer:
                                          (SEQ ID NO: 59)
5'-AGCCACATGCCGCATATTGACAAAG-3'

Reverse primer:
                                          (SEQ ID NO: 60)
5'-AGGGATTCAGTGTGCTACAGGCTGC-3'
```

A 1.8 kb PCR product would be generated only upon the occurrence of a precise gene replacement at the cbhll locus. If the cassette had integrated elsewhere in the genome, no amplification would result.

A small amount of spores from each transformant was suspended in 25 µl of TE buffer and heated on high in a microwave oven for 1 minute. Each microwaved spore suspension was used as a template in the PCR reaction. The reaction was composed of 1 µl of the microwaved spore suspension, 1 µl of a 10 mM dNTPs, 12.5 µl of 2× ADVANTAGE® GC-Melt LA Buffer (Clontech, Mountain View, Calif., USA), 25 pmol of forward primer, 25 pmol of reverse primer, 1.25 units of ADVANTAGE® GC Genomic LA Polymerase Mix (Clontech, Mountain View, Calif., USA), and 9.25 µl of water. The reaction was incubated in an EPPENDORF® MASTERCYCLER® 5333 epgradient S programmed for 1 cycle at 95° C. for 10 minutes; 35 cycles each at 95° C. for 30 seconds, 56° C. for 30 seconds, and 72° C. for 1 minute 40 seconds; 1 cycle at 72° C. for 7 minutes; and a 4° C. hold. The PCR reactions were subjected to 1% agarose gel electrophoresis using TAE buffer. The spore PCR indicated that four of the seven transformants contained the replacement cassette at the targeted locus and three of them were submitted to Southern analysis to confirm the replacement cassette was in a single copy.

Genomic DNA was isolated from the three transformants according to the procedure described in Example 1 and each transformant submitted to Southern analysis. For Southern analysis, 2 µg of genomic DNA was digested with 50 units of Dra I in a 50 µl reaction volume and subjected to 1% agarose electrophoresis in TAE buffer. The DNA in the gel was depurinated with one 10 minute wash in 0.25 N HCl, denatured with two 15 minute washes in 0.5 N NaOH-1.5 M NaCl, neutralized with one 30 minute wash in 1 M Tris pH 8-1.5 M NaCl, and incubated in 20×SSC for 5 minutes. The DNA was transferred to a NYTRAN® Supercharge membrane. The DNA was UV crosslinked to the membrane using a STRATALINKER™ UV crosslinker and prehybridized for 1 hour at 42° C. in 20 ml of DIG Easy Hyb.

A probe hybridizing to the 3' cbhII gene flanking sequence was generated using a PCR Dig Probe Synthesis Kit according to the manufacturer's instructions with the forward and reverse primers indicated below. The PCR reaction was composed of 1× HERCULASE® Reaction Buffer, 400 nM each primer, 200 µM DIG-labeled dUTP-containing dNTPs, 150 ng of *T. reesei* RutC30 genomic DNA, and 1.5 units of HERCULASE® Hot Start High-Fidelity DNA Polymerase. The reaction was incubated in an EPPENDORF® MASTERCYCLER® 5333 epgradient S programmed for 1 cycle at 95° C. for 2 minutes; 30 cycles each at 95° C. for 30 seconds, 51° C. for 30 seconds, and 72° C. for 40 seconds; and 1 cycle at 72° C. for 7 minutes.

```
Forward primer:
                                    (SEQ ID NO: 61)
5'-AAAAAACAAACATCCCGTTCATAAC-3'

Reverse primer:
                                    (SEQ ID NO: 62)
5'-AACAAGGTTTACCGGTTTCGAAAAG-3'
```

The probe was purified by 1% agarose gel electrophoresis using TAE buffer where a 0.5 kb band corresponding to the probe was excised from the gel and extracted using a QIAQUICK® Gel Extraction Kit. The probe was boiled for 5 minutes, chilled on ice for 2 minutes, and added to 10 ml of DIG Easy Hyb to produce the hybridization solution. Hybridization was performed at 42° C. for approximately 17 hours. The membrane was then washed under low stringency conditions in 2×SSC plus 0.1% SDS for 5 minutes at room temperature followed by two high stringency washes in 0.5×SSC plus 0.1% SDS for 15 minutes each at 65° C. The probe-target hybrids were detected by chemiluminescent assay (Roche Diagnostics, Indianapolis, Ind., USA) according to the manufacturer's instructions. Southern analysis indicated that the three transformants contained the replacement cassette at the cbhII locus and all three (designated JfyS139/144-5, -6, and -10) were chosen for curing the hpt and tk markers.

A fresh plate of spores for each transformant was generated by transferring a plug of a 7 day old culture grown on a PDA plate at 28° C. to a new PDA plate and incubating for 7 days at 28° C. Spores were collected in 10 ml of 0.01% TWEEN® 20 using a sterile spreader. The concentration of spores was determined using a hemacytometer and $10^5$ and $10^4$ spores were spread onto 150 mm plates containing TrMM-G medium supplemented with 1 µM FdU.

Approximately 500 FdU-resistant spore isolates for each transformant were obtained from the plate containing $10^5$ spores and approximately 100 FdU-resistant spore isolates for each transformant from the plate containing $10^4$ spores. Eight spore isolates were picked for strains JfyS139/144-5 and -6 and four were picked for strain JfyS139/144-10. Each isolate 1 to 8 from primary transformant 5 was designated JfyS139/144-5A to -5H. Isolates 1 to 8 from primary transformant 6 were designated JfyS139/144-6A to 6H. Isolates from primary transformant 10 were designated JfyS139/144-10A to 10D for isolates 1 to 4. Spore PCR was conducted as described above, using the forward and reverse primers shown below, to confirm the hpt and tk markers had been correctly excised.

```
Forward primer:
                                    (SEQ ID NO: 63)
5'-GTTAAGCATACAATTGAACGAGAATGG-3'

Reverse primer:
                                    (SEQ ID NO: 64)
5'-GATGATATAATGGAGCAAATAAGGG-3'
```

The PCR reactions were performed as described above with the following cycling parameters: 1 cycle at 95° C. for 2 minutes; 30 cycles each at 95° C. for 30 seconds, 55° C. for 30 seconds, and 72° C. for 6 minutes seconds; and 1 cycle at 72° C. for 7 minutes.

The primers annealed to the 5' (forward) and 3' (reverse) flanking sequences used for the cbhII gene replacement. Strains from which the hpt/tk cassette had been correctly excised would display a 3.5 kb fragment while those with the markers intact would display an 8 kb fragment. The PCR screen indicated that all of the spore isolates had correctly excised the hpt/tk cassette.

DNA was extracted from the A and B spore isolates from each primary transformant and submitted to Southern analysis as described above. The Southern analysis confirmed that each spore isolate had correctly excised the hpt/tk cassette. Spore isolate *T. reesei* JfyS139/144-10B was chosen to represent the strain containing both the *T. reesei* cbhI and cbhII genes replaced with the respective homologs from *Aspergillus fumigatus*.

Example 7: Generation of *Trichoderma reesei* Ku70 Gene Repair Plasmid pTH239

Four DNA segments were combined using an IN-FUSION® Advantage PCR Cloning Kit to generate a construct to replace the disrupted *Trichoderma reesei* ku70 coding sequence with the native *Trichoderma reesei* ku70 coding sequence (SEQ ID NO: 65 [DNA sequence] and SEQ ID NO: 66 [deduced amino acid sequence]). The ampicillin resistance marker region including the prokaryotic origin of replication was amplified from pJfyS139-B (Example 1) using the sequence-specific forward and reverse primers shown below (SEQ ID NOs: 67 and 68). The *T. reesei* ku70 gene upstream sequence (consisting of 989 bp from upstream of the ku70 coding sequence and the first 1010 bp of the ku70 coding sequence) was amplified from *T. reesei* 981-O-8 genomic DNA using the sequence-specific forward and reverse primers shown below (SEQ ID NOs: 69 and 70). The *T. reesei* ku70 gene downstream sequence (consisting of a 500 bp segment repeated from the 3' end of the 1010 bp segment of the ku70 coding sequence amplified in the upstream PCR product, and a 1067 bp segment containing the remainder of the ku70 coding sequence, and 461 bp from downstream of the ku70 coding sequence) was amplified from *T. reesei* 981-O-8 genomic DNA using the sequence-specific forward and reverse primers shown below (SEQ ID NOs: 71 and 72). *T. reesei* 981-O-8 genomic DNA was prepared according to the procedure described in Example 1.

```
Forward primer:
                                    (SEQ ID NO: 67)
5'-GTGTGCGGCCGCTCGAGCATGCATGTTTAAACAGCTTGGCACTGGCC

GTCGTTTT-3'

Reverse primer:
                                    (SEQ ID NO: 68)
5'-ATCAGCCCCGAGACGGCGCCGCGTTTAAACAATTCGTAATCATGGTC

ATAGCTGT-3'

Forward primer:
                                    (SEQ ID NO: 69)
5'-CATGATTACGAATTGTTTAAACGCGGCGCCGTCTCGGGGCTGATCTT

GTCGAGGA-3'

Reverse primer:
                                    (SEQ ID NO: 70)
5'-GGCGGCCGTTACTAGTGGATCCAGCCCTTGACAGTGATCTTGAGTCC

AGGTGCAA-3'

Forward primer:
                                    (SEQ ID NO: 71)
5'-TGCAGATATCCATCACACTGGCGGCCGCAGTTTCCATGTCCAACGTG

TTGTTTTGCGC-3'

Reverse primer:
                                    (SEQ ID NO: 72)
5'-GCCAGTGCCAAGCTGTTTAAACATGCATGCTCGAGCGGCCGCACACG

CCCTCTCCTCG-3'
```

For amplification of the ampicillin resistance marker and prokaryotic origin of replication region, the reaction was composed of 100 ng of *T. reesei* 981-O-8 genomic DNA, 200 µM dNTPs, 1 µM of each primer (SEQ ID NO: 67 and 70), 1× PHUSION® High-Fidelity Hot Start DNA Polymerase Buffer (New England Biolabs, Inc., Ipswich, Mass., USA), and 1.0 unit of PHUSION® High-Fidelity Hot Start DNA Polymerase (New England Biolabs, Inc., Ipswich, Mass., USA) in a final volume of 50 µl. The amplification reaction was incubated in an EPPENDORF® MASTERCYCLER® 5333 epgradient S programmed for 1 cycle at 98° C. for 30 seconds; 30 cycles each at 98° C. for 10 seconds, 55° C. for 30 seconds, and 72° C. for 1 minute 30 seconds; and 1 cycle at 72° C. for 7 minutes. The PCR product was separated by 1% agarose gel electrophoresis using TAE buffer where a 2.692 kb fragment was excised from the gels and extracted using a MINELUTE® Gel Extraction Kit.

For amplification of the ku70 gene upstream sequence or downstream sequence, the reactions were composed of 100 ng of pJfyS139-B, 200 µM dNTPs, 1 µM of each primer (SEQ ID NOs: 69 and 70 or 71 and 72, respectively), 1× PHUSION® High-Fidelity Hot Start DNA Polymerase Buffer, and 1.0 unit of PHUSION® High-Fidelity Hot Start DNA Polymerase in a final volume of 50 µl. The amplification reactions were incubated in an EPPENDORF® MASTERCYCLER® 5333 epgradient S programmed for 1 cycle at 98° C. for 30 seconds; 30 cycles each at 98° C. for 10 seconds, 55° C. for 30 seconds, and 72° C. for 1 minute 30 seconds; and 1 cycle at 72° C. for 7 minutes. The PCR products were separated by 1% agarose gel electrophoresis using TAE buffer where 1.999 kb and 2.028 kb fragments were separately excised from the gels and extracted using a MINELUTE® Gel Extraction Kit.

The fourth DNA segment was generated from a restriction enzyme digestion of pJfyS139-B with Not I and Bam HI. The reaction was composed of 5 µg of pJfyS139-B, 10 units of Not I, 20 units of Bam HI, and 20 µl of Restriction Enzyme Buffer 2 (New England Biolabs, Inc., Ipswich, Mass., USA) in a total volume of 50 µl. The reaction was incubated for 1 hour at 37° C. and then separated by 1% agarose gel electrophoresis using TAE buffer where a 4.400 kb fragment was excised from the gel and extracted using a MINELUTE® Gel Extraction Kit.

The three PCR products of 2,028 bp, 1,999 bp and 2,692 bp were inserted into Not I and Bam HI-digested pJfyS139-B using an IN-FUSION® Advantage PCR Cloning Kit according to the manufacturer's protocol. The IN-FUSION® reaction was composed of 1× IN-FUSION® Reaction Buffer, 50 ng of the Not I/Bam HI-digested pJfyS139-B, 50 ng of the 1.999 kb ku70 gene upstream PCR product, 50 ng of the 2.028 kb ku70 gene downstream PCR product, 50 ng of the 2.692 kb ampicillin resistance marker and prokaryotic origin of replication PCR product, and 1 µl of IN-FUSION® Enzyme in a 10 µl reaction volume. The reaction was incubated for 15 minutes at 37° C. followed by 15 minutes at 50° C. After the incubation period 40 µl of TE were added to the reaction. A 3 µl aliquot was used to transform *E. coli* XL10 GOLD® competent cells (Stratagene, La Jolla, Calif., USA) according to the manufacturer's protocol. The cells were heat shocked at 42° C. for 30 seconds and then 500 µl of NZY+ medium, pre-heated to 42° C., were added. The tubes were incubated at 37° C. with shaking at 200 rpm for 40 minutes and then plated onto 150 mm diameter 2XYT plus ampicillin plates and incubated at 37° C. overnight. The resulting transformants were screened by restriction digestion analysis with Hind III and Xba I and positive clones sequenced to ensure the absence of PCR errors. One clone containing the insert with no PCR errors was identified and designated pTH239.

Example 8: Repair of the Ku70 Gene in the *A. fumigatus* cbh1 and cbh2 Replacement Strain JfyS139/144-10B The native *Trichoderma reesei* ku70 gene was repaired in strain *T. reesei* JfyS139/144-10B (Example 6) in order to facilitate strain manipulation steps requiring the function of the ku70 gene in non-homologous end-joining. *T. reesei* JfyS129/144-10B was transformed with 23×2 µg of Pme I-linearized pTH239 (Example 7) according to the procedure described in Example 2. Nineteen transformants were obtained and each one was separately transferred to a PDA plate and incubated for 7 days at 28° C.

All nineteen transformants were screened by PCR to confirm homologous integration of the pTH239 Pme I fragment at the disrupted ku70 gene locus. For each of the transformants a sterile inoculation loop was used to collect spores from a 7 day old PDA plate. The spores were transferred to a tube containing 25 µl of 1 mM EDTA-10 mM Tris buffer and microwaved on high for 1 minute. A 1 µl aliquot of the microwaved spore mixture was added directly to the PCR reaction as template DNA. A set of PCR primers shown below were designed to amplify across the disrupted region of the ku70 coding sequence to distinguish between the host genome with the disruption in the ku70 coding sequence (848 bp) and the pTH239 targeted strain of interest (606 bp). The PCR reaction was composed of 1× ADVANTAGE® Genomic LA Polymerase Reaction Buffer (Clontech, Mountain View, Calif., USA), 400 nM of each primer, 200 µM dNTPs, 1 µl of microwaved TE-spore mixture (described above), and 1.0 unit of ADVANTAGE® Genomic LA Polymerase (Clontech, Mountain View, Calif., USA). The amplification reaction was incubated in an EPPENDORF® MASTERCYCLER® 5333 epgradient S programmed for 1 cycle at 95° C. for 10 minutes; 30 cycles each at 95° C. for 30 seconds, 55° C. for 30 seconds, and 72° C. for 60 seconds; and 1 cycle at 72° C. for 7 minutes.

```
Forward primer:
                               (SEQ ID NO: 73)
5'-CAATGACGATCCGCACGCGT-3'

Reverse primer:
                               (SEQ ID NO: 74)
5'-CAATGACGATCCGCACGCGT-3'
```

Only one of the nineteen transformants (#19) was positive for the 606 bp PCR product and negative for the 848 bp PCR product indicative of a strain containing the pTH239 PmeI fragment homologously integrated at the ku70 locus.

Spores from the 7 day old PDA plate of transformant #19 were collected in 10 ml of 0.01% TWEEN® 20 using a sterile spreader. The concentration of spores was determined using a hemocytometer and $10^6$ spores were spread onto 150 mm plates containing TrMM-G medium supplemented with 1 µM 5-fluoro-2'-deoxyuridine (FdU) and cultured for 5 days at 28° C. Twenty-two FdU-resistant spore isolates were obtained and transferred to PDA plates and cultivated at 28° C. for five days.

All twenty-two spore isolates (#19A-V) were screened by PCR for excision of the hpt/tk marker region present between the homologous repeats of the ku70 coding sequence within the repair cassette. For each of the spore isolates a sterile inoculating loop was used to collect spores from a 7 day old PDA plate. The spores were transferred to a tube containing 25 µl of 1 mM EDTA-10 mM Tris buffer and microwaved on high for 1 minute. A 1 µl aliquot of the spore mixture was added directly to the PCR reaction as template genomic DNA. A set of PCR primers shown below were designed to amplify across the hpt/tk region to distinguish between the presence (6 kb) or absence (1.1 kb) of the hpt/tk region. The PCR reaction was composed of 1× ADVANTAGE® Genomic LA Polymerase Reaction Buffer, 400 nM of each primer (below), 200 µM dNTPs, 1 µl of microwaved TE-spore mixture (described above), and 1.0 unit of ADVANTAGE® Genomic LA Polymerase. The amplification reaction was incubated in an EPPENDORF® MASTERCYCLER® 5333 epgradient S programmed for 1 cycle at 95° C. for 10 minutes; 30 cycles each at 95° C. for 30 seconds, 50° C. for 30 seconds, and 72° C. for 6 minutes; and 1 cycle at 72° C. for 7 minutes.

```
Forward primer:
                               (SEQ ID NO: 75)
5'-GACACTCTTTTCTCCCATCT-3'

Reverse primer:
                               (SEQ ID NO: 76)
5'-GAGGAGCAGAAGAAGCTCCG-3'
```

All twenty-two spore isolates were negative for the 6 kb PCR product corresponding to the hpt/tk marker region.

Spores from the 7 day old PDA plates of isolates #19A and #19L were collected in 10 ml of 0.01% TWEEN® 20 using a sterile spreader. The concentration of spores was determined using a hemocytometer and $10^3$, $10^2$, and $10^1$ spores were spread onto 150 mm PDA plates containing 1 M sucrose and cultured for 3 days at 28° C. Ten spore isolates were selected from the PDA plates for both strains #19A and #19L and transferred to fresh PDA plates and placed at 28° C.

Genomic DNA was extracted from 6 spore isolates of both #19L and #19A, according to the procedure described in Example 1 and submitted to Southern analysis.

For Southern analysis, 2 µg of genomic DNA was digested with (1) 5 units and 10 units, respectively, of Asc I and Xho I or (2) 5 units and 25 units, respectively, of Asc I and Apa I in a 50 µl reaction volume and subjected to 1% agarose electrophoresis using TAE buffer. The DNA in the gel was depurinated with one 10 minute wash in 0.25 N HCl, denatured with two 15 minute washes in 0.5 N NaOH-1.5 M NaCl, neutralized with one 30 minute wash in 1 M Tris pH 8-1.5 M NaCl, and incubated in 20×SSC for 5 minutes. The DNA was transferred to a NYTRAN® Supercharge membrane using a TURBOBLOTTER™ System according to the manufacturer's protocol. The DNA was UV crosslinked to the membrane using a STRATALINKER™ UV Crosslinker and prehybridized for 1 hour at 42° C. in 20 ml of DIG Easy Hyb.

A probe hybridizing to the 3' end of the ku70 coding sequence was generated using a PCR Dig Probe Synthesis Kit (Roche Diagnostics Corporation, Indianapolis, Ind., USA) according to the manufacturer's instructions with the forward and reverse primers shown below. In order to generate a pure template for the probe PCR reaction, the 3' end of the ku70 coding sequence was amplified from *T. reesei* 981-O-8 genomic DNA. The PCR reaction was composed of 1× PHUSION® High-Fidelity Hot Start DNA Polymerase Buffer, 1 µM of each primer, 200 µM dNTPs, 165 ng of *T. reesei* 981-O-8 genomic DNA, and 1.0 unit of PHUSION® High-Fidelity Hot Start DNA Polymerase. The amplification reaction was incubated in an EPPENDORF® MASTERCYCLER® 5333 epgradient S programmed for 1 cycle at 98° C. for 30 seconds; 35 cycles each at 98° C. for 10 seconds, 60° C. for 30 seconds, and 72° C. for 15 seconds; and 1 cycle at 72° C. for 10 minutes.

```
Forward primer:
                               (SEQ ID NO: 77)
5'-gcatatataacccactcaagta-3'

Reverse primer:
                               (SEQ ID NO: 78)
5'-attatcttggaccggccgcagg-3'
```

The 0.5 kb probe template was purified by 1% agarose gel electrophoresis using TAE buffer and excised from the gel and extracted using a MINELUTE® Gel Extraction Kit. The purified PCR product was used to generate a DIG-labeled probe as specified by the manufacturer's instructions using the primers and amplification conditions specified above. The 0.5 kb DIG-labeled probe was purified by 1% agarose gel electrophoresis using TAE buffer and excised from the gel and extracted using a MINELUTE® Gel Extraction Kit. The probe was boiled for 5 minutes, chilled on ice for 2 minutes, and added to 10 ml of DIG Easy Hyb to produce the hybridization solution. Hybridization was performed at 42° C. for 15-17 hours. The membrane was then washed under low stringency conditions in 2×SSC plus 0.1% SDS for 5 minutes at room temperature followed by two high stringency washes in 0.5×SSC plus 0.1% SDS for 15 minutes each at 65° C. The probe-target hybrids were detected by chemiluminescent assay (Roche Diagnostics, Indianapolis, Ind., USA) according to the manufacturer's instructions. Southern analysis indicated that all spore isolates contained the repair/replacement cassette at the ku70 locus and were cured of the hpt and tk markers. One strain designated *T. reesei* 981-O-8.5#10B+Ku70#19L3 was chosen for further transformations.

Example 9: Cloning of an *Aspergillus fumigatus* GH61B Polypeptide Gene

A tblastn search (Altschul et al., 1997, *Nucleic Acids Res.* 25: 3389-3402) of the *Aspergillus fumigatus* partial genome sequence (The Institute for Genomic Research, Rockville, Md., USA) was performed using as query several known GH61 polypeptides including the *Thermoascus aurantiacus* GH61A polypeptide (GeneSeqP Accession Number AEC05922). Several genes were identified as putative GH61 Family homologs based upon a high degree of similarity to the query sequences at the amino acid level. One genomic region of approximately 850 bp with greater than 70% sequence identity to the *Thermoascus aurantiacus* GH61A polypeptide sequence at the amino acid level was chosen for further study.

*A. fumigatus* NN051616 was grown and harvested as described in U.S. Pat. No. 7,244,605. Frozen mycelia were ground, by mortar and pestle, to a fine powder and genomic DNA was isolated using a DNEASY® Plant Maxi Kit according to manufacturer's instructions.

Two synthetic oligonucleotide primers shown below were designed to PCR amplify the *A. fumigatus* Family GH61B polypeptide coding sequence from the genomic DNA. An IN-FUSION® Cloning Kit (Clontech, Palo Alto, Calif., USA) was used to clone the fragment directly into the expression vector pAILo2 (WO 2004/099228), without the need for restriction digestion and ligation.

```
Forward primer:
                                        (SEQ ID NO: 79)
5'-ACTGGATTTACCATGACTTTGTCCAAGATCACTTCCA-3'

Reverse primer:
                                        (SEQ ID NO: 80)
5'-TCACCTCTAGTTAATTAAGCGTTGAACAGTGCAGGACCAG-3'
```

Bold letters represent coding sequence. The remaining sequences are homologous to insertion sites of pAILo2.

Fifty picomoles of each of the primers above were used in a PCR reaction composed of 204 ng of *A. fumigatus* genomic DNA, 1×Pfx Amplification Buffer (Invitrogen, Carlsbad, Calif., USA), 1.5 µl of a 10 mM blend of dATP, dTTP, dGTP, and dCTP, 2.5 units of PLATINUM® Pfx DNA Polymerase (Invitrogen Corp., Carlsbad, Calif., USA), and 1 µl of 50 mM MgSO$_4$ in a final volume of 50 µl. The amplification was performed using an EPPENDORF® MASTERCYCLER® 5333 epgradient S programmed for 1 cycle at 94° C. for 3 minutes; and 30 cycles each at 94° C. for 30 seconds, 56° C. for 30 seconds, and 72° C. for 1 minutes. The heat block was then held at 72° C. for 15 minutes followed by a 4° C. soak cycle. The reaction products were isolated by 1.0% agarose gel electrophoresis using TAE buffer where an approximately 850 bp product band was excised from the gel and purified using a MIN-ELUTE® Gel Extraction Kit according to the manufacturer's instructions.

Figure 4:
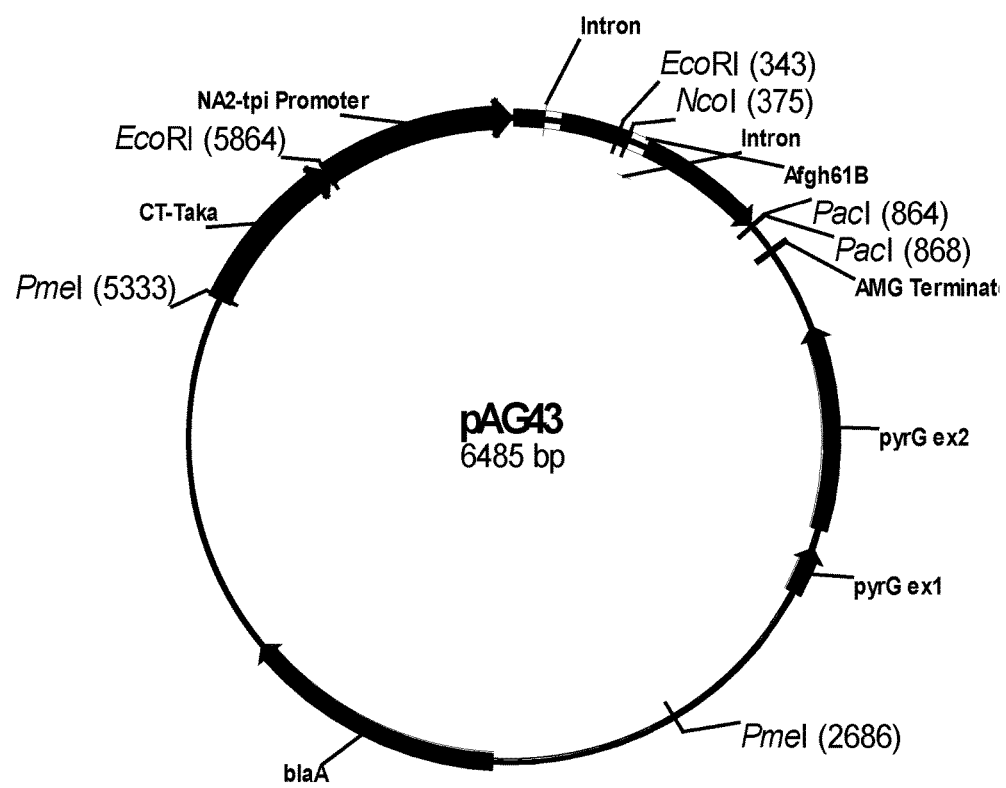
FIG. 4 shows a restriction map of plasmid pAG43.

The 850 bp fragment was then cloned into pAILo2 using an IN-FUSION® Cloning Kit. Plasmid pAILo2 was digested with Nco I and Pac I. The plasmid fragment was purified by gel electrophoresis as above and a QIAQUICK® Gel Purification Kit. The gene fragment and the digested vector were combined together in a reaction described below resulting in the expression plasmid pAG43 (FIG. 4) in which transcription of the *A. fumigatus* GH61B polypeptide coding sequence was under the control of the NA2-tpi promoter. The NA2-tpi promoter is a modified promoter from the *Aspergillus niger* neutral alpha-amylase gene in which the untranslated leader has been replaced by an untranslated leader from the *Aspergillus nidulans* triose phosphate isomerase gene. The recombination reaction (20 µl) was composed of 1× IN-FUSION® Reaction Buffer, 1×BSA (Clontech, Palo Alto, Calif., USA), 1 µl of IN-FUSION® Enzyme (diluted 1:10), 166 ng of pAILo2 digested with Nco I and Pac I, and 110 ng of the *A. fumigatus* GH61B polypeptide purified PCR product. The reaction was incubated at 37° C. for 15 minutes followed by 15 minutes at 50° C. The reaction was diluted with 40 µl of 10 mM Tris-0.1 M EDTA buffer and 2.5 µl of the diluted reaction was used to transform *E. coli* XL10 SOLOPACK® Gold Competent Cells (Stratagene, La Jolla, Calif., USA). An *E. coli* transformant containing pAG43 (GH61B polypeptide coding sequence) was identified by restriction enzyme digestion and plasmid DNA was prepared using a BIOROBOT® 9600 (QIAGEN Inc., Valencia, Calif., USA).

DNA sequencing of the 862 bp PCR fragment was performed with an Applied Biosystems Model 377 XL Automated DNA Sequencer (Applied Biosystems, Carlsbad, Calif., USA) using dye-terminator chemistry (Giesecke et al., 1992, *Journal of Virology Methods* 38: 47-60) and primer walking strategy. The following vector specific primers were used for sequencing:

```
pAllo2 5 Seq:
                                        (SEQ ID NO: 81)
5'-TGTCCCTTGTCGATGCG 3' pAllo2 3 Seq:
                                        (SEQ ID NO: 82)
5'-CACATGACTTGGCTTCC 3'
```

Nucleotide sequence data were scrutinized for quality and all sequences were compared to each other with assistance of PHRED/PHRAP software (University of Washington, Seattle, Wash., USA).

A gene model for the *A. fumigatus* sequence was constructed based on similarity of the encoded protein to the *Thermoascus aurantiacus* GH61A protein (GeneSeqP Accession Number AEC05922). The nucleotide sequence and deduced amino acid sequence of the *A. fumigatus* GH61B polypeptide coding sequence are shown in SEQ ID NO: 7 and SEQ ID NO: 8, respectively. The genomic fragment encodes a polypeptide of 250 amino acids, interrupted by 2 introns of 53 and 56 bp. The % G+C content of the coding sequence and the mature coding sequence are 53.9% and 57%, respectively. Using the SignalP software program (Nielsen et al., 1997, *Protein Engineering* 10: 1-6), a signal peptide of 21 residues was predicted. The predicted mature protein contains 221 amino acids with a predicted molecular mass of 23.39 kDa.

Example 10: Construction of pSMai214 for Expression of the *Aspergillus fumigatus* GH61B Polypeptide The *Aspergillus fumigatus* GH61B polypeptide coding sequence was amplified from plasmid pAG43 (Example 9) using the gene-specific forward and reverse primers shown below. The region in italics represents vector homology to the site of insertion for an IN-FUSION® reaction.

Forward primer:
(SEQ ID NO: 83)
5'-*GGACTGCGCACC*ATGACTTTGTCCAAGATCACTTCCA-3'

Reverse primer:
(SEQ ID NO: 84)
5'-*GCCACGGAGCTT*AATTAATTAAGCGTTGAACAGTGCAG-3'

Fifty picomoles of each of the primers above were used in a PCR reaction composed of 10 ng of pAG43 DNA, 1×Pfx Amplification Buffer, 1.5 µl of a 10 mM blend of dATP, dTTP, dGTP, and dCTP, 2.5 units of PLATINUM® Pfx DNA Polymerase, and 1 µl of 50 mM MgSO₄ in a final volume of 50 µl. The amplification was performed using an EPPENDORF® MASTERCYCLER® 5333 epgradient S programmed for 1 cycle at 98° C. for 3 minutes; and 30 cycles each at 98° C. for 30 seconds, 56° C. for 30 seconds, and 72° C. for 1 minute. The heat block was then held at 72° C. for 15 minutes. The PCR products were separated by 1% agarose gel electrophoresis using TAE buffer where an approximately 0.9 kb fragment was excised from the gel and extracted using a MINELUTE® Gel Extraction Kit according to the manufacturer's protocol.

Plasmid pMJ09 (WO 2005/047499) was digested with Nco I and Pac I, isolated by 1.0% agarose gel electrophoresis in 1 mM disodium EDTA-50 mM Tris base-50 mM boric acid (TBE) buffer, excised from the gel, and extracted using a QIAQUICK® Gel Extraction Kit according to the manufacturer's instructions.

Figure 5:
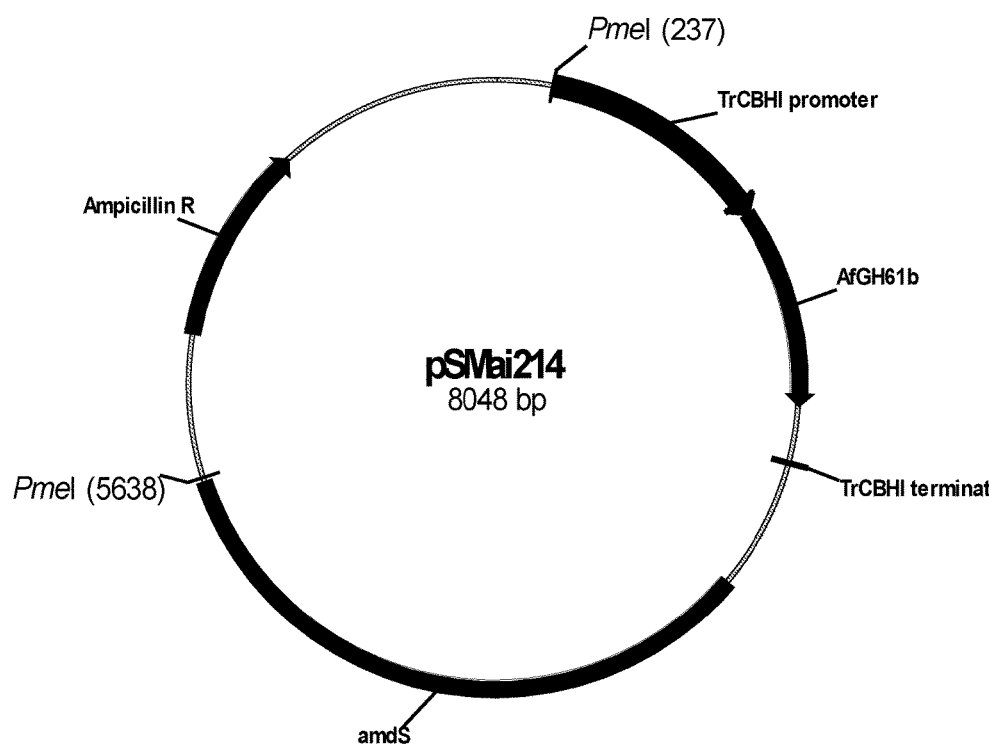
FIG. 5 shows a restriction map of plasmid pSMai214.

The 0.9 kb PCR product was inserted into the gel-purified Nco I/Pac I digested pMJ09 using an IN-FUSION® PCR Cloning Kit (Clontech, Palo Alto, Calif., USA) according to the manufacturer's protocol. The IN-FUSION® reaction was composed of 1× IN-FUSION® Reaction Buffer, 100 ng of the gel-purified Nco I/Pac I digested pMJ09, 37 ng of the 0.9 kb PCR product, 2 µl of 500 µg/ml BSA, and 1 µl of IN-FUSION® Enzyme in a 20 µl reaction volume. The reaction was incubated for 15 minutes at 37° C. and 15 minutes at 50° C. After the incubation period 30 µl of TE buffer were added to the reaction. A 2.5 µl aliquot was used to transform SOLOPACK® Gold Supercompetent Cells according to the manufacturer's protocol. Transformants were screened by sequencing and one clone containing the insert with no PCR errors was identified and designated pSMai214 (FIG. 5). Plasmid pSMai214 can be digested with Pme I to generate an approximately 5.4 kb fragment for *T. reesei* transformation. The 5.4 kb fragment contains the expression cassette composed of the *T. reesei* Cel7A cellobiohydrolase I gene promoter, *A. fumigatus* GH61B polypeptide coding sequence, *T. reesei* Cel7A cellobiohydrolase I gene terminator, and *Aspergillus nidulans* acetamidase (amdS) gene.

Example 11: Construction of a Tandem Construct pDM287 for Expression of Both *Aspergillus fumigatus* CEL3A Beta-Glucosidase and *Aspergillus fumigatus* GH61B Polypeptide An *A. fumigatus* GH61B polypeptide expression cassette was amplified from plasmid pSMai214 using the gene-specific forward and reverse primers shown below. The region in italics represents vector homology to the site of insertion for an IN-FUSION® reaction.

Forward primer:
(SEQ ID NO: 85)
5'-*CGCGGTAGTGGCGCGG*TCGACCGAATGTAGGATTGTT-3'

Reverse primer:
(SEQ ID NO: 86)
5'-*TTACCAATTGGCGCGC*CACTACCGCGTTCGAGAAGA-3'

Fifty picomoles of each of the primers above were used in a PCR reaction composed of 25 ng of pSMai214 DNA, 1× PHUSION™ High-Fidelity Hot Start DNA Polymerase Buffer, 1 µl of a 10 mM blend of dATP, dTTP, dGTP, and dCTP, and 1 unit of PHUSION™ High-Fidelity Hot Start DNA Polymerase in a final volume of 50 µl. The amplification was performed using an EPPENDORF® MASTERCYCLER® 5333 epgradient S programmed for 1 cycle at 98° C. for 30 seconds; 35 cycles each at 98° C. for 10 seconds, 60° C. for 30 seconds, and 72° C. for 1 minute 30 seconds; and 1 cycle at 72° C. for 10 minutes. PCR products were separated by 0.8% agarose gel electrophoresis using TAE buffer where an approximately 2.33 kb fragment was excised from the gel and extracted using a NUCLEOSPIN® Extract II Kit (Macherey-Nagel, Inc., Bethlehem, Pa., USA) according to the manufacturer's protocol.

Figure 6:
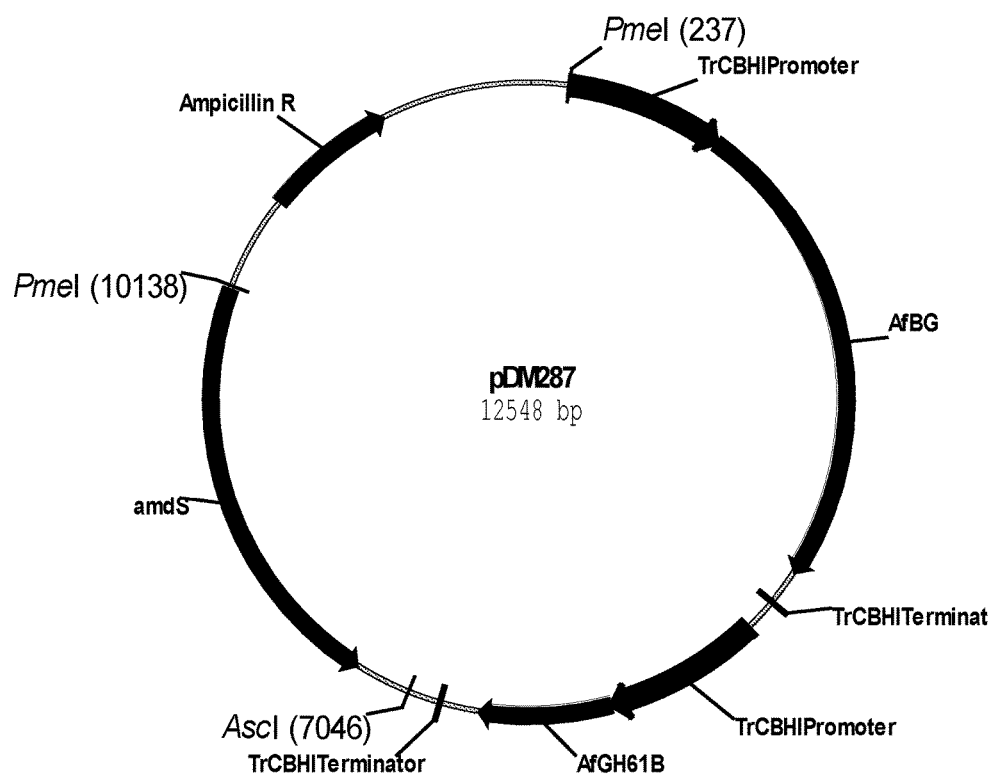
FIG. 6 shows a restriction map of plasmid pDM287.

The approximately 2.3 kb PCR product was inserted into Asc I-digested pEJG107 (WO 2005/047499) using an IN-FUSION® Advantage PCR Cloning Kit according to the manufacturer's protocol. Plasmid pEJG107 comprises an *Aspergillus fumigatus* CEL3A beta-glucosidase encoding sequence (SEQ ID NO: 5 [DNA sequence] and SEQ ID NO: 6 [deduced amino acid sequence]). The IN-FUSION® reaction was composed of 1× IN-FUSION® Reaction Buffer, 125 ng of the Asc I-digested pEJG107, 90 ng of the 2.33 kb PCR product, and 1 µl of IN-FUSION® Enzyme in a 10 µl reaction volume. The reaction was incubated for 15 minutes at 37° C. followed by 15 minutes at 50° C. After the incubation period 40 µl of TE were added to the reaction. A 2 µl aliquot was used to transform ONE SHOT® TOP10 competent cells according to the manufacturer's protocol. The *E. coli* transformation reactions were spread onto 2XYT plus ampicillin plates. The transformants were screened by sequencing and one clone containing the insert with no PCR errors was identified and designated pDM287 (FIG. 6). Plasmid pDM287 can be digested with Pme I to generate an approximately 9.9 kb fragment for *T. reesei* transformation. The 9.9 kb fragment contains two expression cassettes composed of (1) the *T. reesei* Cel7A cellobiohydrolase I gene promoter, *A. fumigatus* CEL3A beta-glucosidase coding sequence, and *T. reesei* Cel7A cellobiohydrolase I gene terminator; and (2) the *T. reesei* Cel7A cellobiohydrolase I gene promoter, *A. fumigatus* GH61B polypeptide coding sequence, and *T. reesei* Cel7A cellobiohydrolase I gene terminator. The 9.9 kb fragment also contains the *Aspergillus nidulans* acetamidase (amdS) gene.

Example 12: Expression of *Aspergillus fumigatus* Beta-Glucosidase and GH61B Polypeptide in Ku70+ *Aspergillus fumigatus* cbh1 and Cbh2 Replacement Strain *T. reesei* 981-O-8.5#10B+Ku70#19L3

In order to express the *A. fumigatus* beta-glucosidase and *A. fumigatus* GH61B polypeptide, protoplasts of *Trichoderma reesei* strain 981-O-8.5#10B+Ku70#19L3 (described in Example 8) were generated as described in Example 2 and transformed with 2 µg of Pme I linearized pDM287. For transformation 100 µl of protoplasts were transferred to a 14 ml polypropylene tube to which 2 µg of Pme I linearized, gel-purified pDM287 was added. Two hundred and fifty µl of PEG buffer were added and the tubes mixed gently by inverting 6 times. The tubes were incubated at 34° C. for 30 minutes after which 3 ml of STC were added. The contents of the tube were split and plated onto 2 separate 150 mm diameter COVE plates and incubated at 28° C. for 11 days. Transformants were picked using a sterile 1 µl inoculation loop and transferred to a fresh 75 mm diameter COVE2+10 mM uridine plate and incubated for 6 days at 28° C.

Transformants were each grown in shake flasks by inoculating 25 ml of CIM medium in a 125 ml polycarbonate non-baffled shake flask with spores collected using a 10 µl inoculation loop. The flasks were incubated at 28° C. with shaking at 200 rpm for 5 days. The shake flasks were harvested by pouring the entire culture into a 50 ml conical bottom tube and centrifuging the samples for 10 minutes at 2500 rpm in a SORVALL® Legend RT+ swing-bucket centrifuge (Thermo Fisher Scientific, Waltham, Mass., USA). Ten ml of each supernatant were transferred to a 15 ml conical bottom tube. Five µl of supernatant were combined with 5 µl of Laemelli sample buffer (Bio-Rad Laboratories, Hercules, Calif., USA) with 5% beta-mercaptoethanol (Sigma Aldrich, St. Louis, Mo., USA) in a 0.2 ml microcentrifuge tube and boiled for 5 minutes at 95° C. in an EPPENDORF® MASTERCYCLER® 5333 epgradient S. Samples were analyzed by SDS-PAGE using a CRITERION® 8-16% Tris-HCl Gel (Bio-Rad Laboratories, Hercules, Calif., USA) according to the manufacturer's instructions using 10 µl of PRECISION PLUS™ All Blue Protein Standards (Bio-Rad Laboratories, Hercules, Calif., USA). Gels were stained and de-stained using BIO-SAFE™ Coomassie (Bio-Rad Laboratories, Hercules, Calif., USA). One strain (*T. reesei* JfyS-DM287-23) was selected based on high expression of the *A. fumigatus* beta-glucosidase and *A. fumigatus* GH61B polypeptide. Ten ml of *T. reesei* JfyS-DM287-23 shake flask broth was sterilized using a sterile 30 ml syringe and a MILLEX® GP 0.22 µm syringe filter (Millipore, Bedford, Mass., USA), transferred to a new 15 ml conical tube, and stored at −20° C. Protein concentration was determined using a Microplate BCA™ Protein Assay Kit (Thermo Fischer Scientific, Waltham, Mass., USA) in which bovine serum albumin was used as a protein standard.

Example 13: Pretreated Corn Stover Hydrolysis Assay

Corn stover was pretreated at the U.S. Department of Energy National Renewable Energy Laboratory (NREL) using 1.4 wt % sulfuric acid at 165° C. and 107 psi for 8 minutes. The water-insoluble solids in the pretreated corn stover (PCS) contained 56.5% cellulose, 4.6% hemicelluloses, and 28.4% lignin. Cellulose and hemicellulose were determined by a two-stage sulfuric acid hydrolysis with subsequent analysis of sugars by high performance liquid chromatography using NREL Standard Analytical Procedure #002. Lignin was determined gravimetrically after hydrolyzing the cellulose and hemicellulose fractions with sulfuric acid using NREL Standard Analytical Procedure #003.

Milled unwashed PCS (dry weight 32.35%) was prepared by milling whole slurry PCS in a Cosmos ICMG 40 wet multi-utility grinder (EssEmm Corporation, Tamil Nadu, India).

The hydrolysis of PCS was conducted using 2.2 ml deep-well plates (Axygen, Union City, Calif., USA) in a total reaction volume of 1.0 ml. The hydrolysis was performed with 50 mg of insoluble PCS solids per ml of 50 mM sodium acetate pH 5.0 buffer containing 1 mM manganese sulfate and various protein loadings of various enzyme compositions (expressed as mg protein per gram of cellulose). Enzyme compositions were prepared and then added simultaneously to all wells in a volume ranging from 50 µl to 200 µl, for a final volume of 1 ml in each reaction. The plates were then sealed using an ALPS-300™ plate heat sealer (Abgene, Epsom, United Kingdom), mixed thoroughly, and incubated at a specific temperature for 72 hours. All experiments reported were performed in triplicate.

Following hydrolysis, samples were filtered using a 0.45 µm MULTISCREEN® 96-well filter plate (Millipore, Bedford, Mass., USA) and filtrates analyzed for sugar content as described below. When not used immediately, filtered aliquots were frozen at −20° C. The sugar concentrations of samples diluted in 0.005 M $H_2SO_4$ were measured using a 4.6×250 mm AMINEX® HPX-87H column (Bio-Rad Laboratories, Inc., Hercules, Calif., USA) by elution with 0.05% w/w benzoic acid-0.005 M $H_2SO_4$ at 65° C. at a flow rate of 0.6 ml per minute, and quantitation by integration of the glucose, cellobiose, and xylose signals from refractive index detection (CHEMSTATION®, AGILENT® 1100 HPLC, Agilent Technologies, Santa Clara, Calif., USA) calibrated by pure sugar samples. The resultant glucose and cellobiose equivalents were used to calculate the percentage of cellulose conversion for each reaction.

Glucose, cellobiose, and xylose were measured individually. Measured sugar concentrations were adjusted for the appropriate dilution factor. In case of unwashed PCS, the net concentrations of enzymatically-produced sugars were determined by adjusting the measured sugar concentrations for corresponding background sugar concentrations in unwashed PCS at zero time points. All HPLC data processing was performed using MICROSOFT EXCEL™ software (Microsoft, Richland, Wash., USA).

The degree of cellulose conversion to glucose was calculated using the following equation: % conversion=(glucose concentration/glucose concentration in a limit digest)×100. In order to calculate % conversion, a 100% conversion point was set based on a cellulase control (100 mg of *Trichoderma reesei* cellulase per gram cellulose), and all values were divided by this number and then multiplied by 100. Triplicate data points were averaged and standard deviation was calculated.

Example 14: Preparation of *Aspergillus oryzae* Beta-Glucosidase

*Aspergillus oryzae* beta-glucosidase (SEQ ID NO: 87 [DNA sequence] and SEQ ID NO: 88 [deduced amino acid sequence]) was prepared recombinantly according to WO 02/095014 using *Aspergillus oryzae* as a host.

The filtered broth of *Aspergillus oryzae* beta-glucosidase was concentrated and buffer exchanged using a tangential flow concentrator (Pall Filtron, Northborough, Mass., USA) equipped with a 10 kDa polyethersulfone membrane (Pall Filtron, Northborough, Mass., USA) with 20 mM Tris-HCl pH 8.0. The buffer exchanged sample was loaded onto a MonoQ® column (GE Healthcare, Piscataway, N.J., USA) equilibrated with 20 mM Tris-HCl pH 8.0, and the bound protein was eluted with a linear gradient from 0 to 1000 mM sodium chloride. Protein fractions were pooled and concentrated using 10 kDa MW-CO Amicon Ultra centrifuge concentrator (Millipore, Bedford, Mass., USA) into 20 mM Tris-HCl pH 8.0. Protein concentration was determined using a Microplate BCA™ Protein Assay Kit with bovine serum albumin as a protein standard.

Example 15: Preparation of *Aspergillus fumigatus* Enzyme Composition

Preparation of *Aspergillus fumigatus* Cel7A cellobiohydrolase I. The *Aspergillus fumigatus* Cel7A cellobiohydrolase I (SEQ ID NO: 1 [DNA sequence] and SEQ ID NO: 2 [deduced amino acid sequence]) was prepared recombinantly in *Aspergillus oryzae* as described in WO 2011/057140. The *Aspergillus fumigatus* Cel7A cellobiohydrolase I was purified according to WO 2011/057140.

Preparation of *Aspergillus fumigatus* cellobiohydrolase II. The *Aspergillus fumigatus* GH6A cellobiohydrolase II (SEQ ID NO: 3 [DNA sequence] and SEQ ID NO: 4 [deduced amino acid sequence]) was prepared recombinantly in *Aspergillus oryzae* as described in WO 2011/057140. The filtered broth of *Aspergillus fumigatus* GH6A cellobiohydrolase II was buffer exchanged into 20 mM Tris pH 8.0 using a 400 ml SEPHADEX™ G-25 column (GE Healthcare, United Kingdom) according to the manufacturer's instructions. Fractions were collected, pooled, and adjusted to 1.2 M ammonium sulphate-20 mM Tris pH 8.0. The equilibrated protein was loaded onto a PHENYL SEPHAROSE™ 6 Fast Flow column (high sub) (GE Healthcare, Piscataway, N.J., USA) equilibrated in 20 mM Tris pH 8.0 with 1.2 M ammonium sulphate, and bound proteins were eluted with 20 mM Tris pH 8.0 with no ammonium sulphate. The fractions were pooled.

Preparation of *Aspergillus fumigatus* strain GH5 endoglucanase II. The *Aspergillus fumigatus* GH5 endoglucanase II (SEQ ID NO: 11 [DNA sequence] and SEQ ID NO: 12 [deduced amino acid sequence]) was prepared recombinantly in *Aspergillus oryzae* as described in WO 2011/057140. The *Aspergillus fumigatus* GH5 endoglucanase II was purified according to WO 2011/057140.

Preparation of *Aspergillus fumigatus* GH61B polypeptide having cellulolytic enhancing activity. The *Aspergillus fumigatus* GH61B polypeptide having cellulolytic enhancing activity (SEQ ID NO: 7 [DNA sequence] and SEQ ID NO: 8 [deduced amino acid sequence]) was prepared recombinantly in *Aspergillus oryzae* as described in WO 2011/057140. The *Aspergillus fumigatus* GH61B polypeptide having cellulolytic enhancing activity was purified according to WO 2011/057140.

Preparation of *Aspergillus fumigatus* GH10 xylanase. The *Aspergillus fumigatus* GH10 xylanase (xyn3) (SEQ ID NO: 17 [DNA sequence] and SEQ ID NO: 18 [deduced amino acid sequence]) was prepared recombinantly according to WO 2006/078256 using *Aspergillus oryzae* BECh2 (WO 2000/39322) as a host. The filtered broth of *Aspergillus fumigatus* NN055679 GH10 xylanase (xyn3) was desalted and buffer-exchanged into 50 mM sodium acetate pH 5.0 using a HIPREP® 26/10 Desalting Column according to the manufacturer's instructions.

Preparation of *Aspergillus fumigatus* Cel3A beta-glucosidase. *Aspergillus fumigatus* Cel3A beta-glucosidase (SEQ ID NO: 5 [DNA sequence] and SEQ ID NO: 6 [deduced amino acid sequence]) was recombinantly prepared according to WO 2005/047499 using *Aspergillus oryzae* as a host. The filtered broth of *Aspergillus fumigatus* Cel3A beta-glucosidase was concentrated and buffer exchanged using a tangential flow concentrator equipped with a 10 kDa polyethersulfone membrane with 20 mM Tris-HCl pH 8.5. The sample was loaded onto a Q SEPHAROSE® High Performance column (GE Healthcare, Piscataway, N.J., USA) equilibrated in 20 mM Tris pH 8.5, and bound proteins were eluted with a linear gradient from 0-600 mM sodium chloride. The fractions were concentrated and loaded onto a SUPERDEX® 75 HR 26/60 column equilibrated with 20 mM Tris-150 mM sodium chloride pH 8.5. Alternatively, the filtered broth was adjusted to pH 8.0 with 20% sodium acetate, which made the solution turbid. To remove the turbidity, the solution was centrifuged at 20,000×g for 20 minutes, and the supernatant was filtered though a 0.2 µm filtration unit (Nalgene, Rochester, N.Y., USA). The filtrate was diluted with deionized water to reach the same conductivity as 50 mM Tris/HCl, pH 8.0. The adjusted enzyme solution was applied to a Q SEPHAROSE® Fast Flow column (GE Healthcare, Piscataway, N.J., USA) equilibrated in 50 mM Tris-HCl, pH 8.0 and eluted with a linear gradient from 0 to 500 mM sodium chloride. Fractions were pooled and treated with 1% (w/v) activated charcoal to remove color from the beta-glucosidase pool. The charcoal was removed by filtration of the suspension through a 0.2 µm filtration unit (Nalgene, Rochester, N.Y., USA). The filtrate was adjusted to pH 5.0 with 20% acetic acid and diluted 10 times with deionized water. The adjusted filtrate was applied to SP SEPHAROSE® Fast Flow column (GE Healthcare, Piscataway, N.J., USA) equilibrated in 10 mM succinic acid pH 5.0 and eluted with a linear gradient from 0 to 500 mM sodium chloride. Fractions were analyzed by SDS-PAGE. Fractions, where only one band was seen on a Coomassie stained SDS-PAGE gel, were pooled as the purified product and used for further experiments.

Preparation of *Aspergillus fumigatus* strain GH3 beta-xylosidase. The *Aspergillus fumigatus* GH3 beta-xylosidase (SEQ ID NO: 19 [DNA sequence] and SEQ ID NO: 20 [deduced amino acid sequence]) was prepared recombinantly in *Aspergillus oryzae* as described in WO 2011/057140. The *Aspergillus fumigatus* GH3 beta-xylosidase was purified according to WO 2011/057140.

The protein concentration for each of the monocomponents described above was determined using a Microplate BCA™ Protein Assay Kit in which bovine serum albumin was used as a protein standard. An *Aspergillus fumigatus* enzyme composition was composed of each monocomponent, prepared as described above, as follows: 37% *Aspergillus fumigatus* Cel7A cellobiohydrolase I, 25% *Aspergillus fumigatus* Cel6A cellobiohydrolase II, 10% *Aspergillus fumigatus* Cel5A endoglucanase II, 15% *Aspergillus fumigatus* GH61B polypeptide having cellulolytic enhancing activity, 5% *Aspergillus fumigatus* GH10 xylanase (xyn3), 5% *Aspergillus fumigatus* beta-glucosidase, and 3% *Aspergillus fumigatus* beta-xylosidase. The *Aspergillus fumigatus* enzyme composition is designated herein as "*Aspergillus fumigatus* enzyme composition (monocomponent mixture)".

Example 16: Expression of *Aspergillus fumigatus* Wild-Type Composition

*Aspergillus fumigatus* strain NN051616 (EXT2007-00107) was inoculated onto a PDA plate and incubated for 4 days at 45° C. in the darkness. Several mycelia-PDA plugs were inoculated into 500 ml shake flasks containing 100 ml of NNCYP07-PCS medium. The flasks were incubated for 5 days at 45° C. with shaking at 160 rpm. The culture broth was filtered using a 0.45 µm DURAPORE® Membrane (Millipore, Bedford, Mass., USA).

A 3 ml volume of the filtrate was desalted and buffer exchanged into 50 mM sodium acetate pH 5.0 using an ECONO-PAC® 10-DG desalting column (Bio-Rad Laboratories, Inc., Hercules, Calif., USA) according to the manufacturer's instructions. Protein concentration was determined by SDS-PAGE densitometry using a CRITERION® 8-16% Tris-HCl Gel, staining with GELCODE™ Blue Stain Reagent (Pierce, Rockford, Ill., USA), and software analysis by ImageJ (National Institutes of Health, Bethesda, Md., USA).

The *Aspergillus fumigatus* enzyme composition is designated herein as "*Aspergillus fumigatus* wild-type enzyme composition".

Example 17: PCS Hydrolysis Assay Comparing the Enzyme Composition of the *T. reesei* Strain Expressing *Aspergillus fumigatus* Enzymes with a *Trichoderma reesei*-Based Cellulase Composition and an *Aspergillus fumigatus* Enzyme Composition The enzyme composition of *T. reesei* JfyS-DM287-23 expressing *Aspergillus fumigatus* cellobiohydrolase I, *A. fumigatus* cellobiohydrolase II, *A. fumigatus* beta-glucosidase, and *A. fumigatus* GH61B polypeptide was evaluated relative to a *Trichoderma reesei*-based cellulase composition (CELLUCLAST™ 1.5L FG; Novozymes A/S, Bagsværd, Denmark replaced with 5% *Aspergillus oryzae* beta-glucosidase), and the *Aspergillus fumigatus* enzyme composition (monocomponent mixture) (Example 15) using milled unwashed PCS at 50° C. The results were compared with the results for the *Trichoderma reesei*-based cellulase composition and the *Aspergillus fumigatus* enzyme composition (monocomponent mixture). All compositions were used at 2.0, 4.0, and 6.0 mg protein per g cellulose.

The assay was performed as described in Example 13. The 1 ml reactions with 5% milled unwashed PCS were conducted for 72 hours in 50 mM sodium acetate pH 5.0 buffer containing 1 mM manganese sulfate. All reactions were performed in triplicate and involved single mixing at the beginning of hydrolysis.

Figure 7:
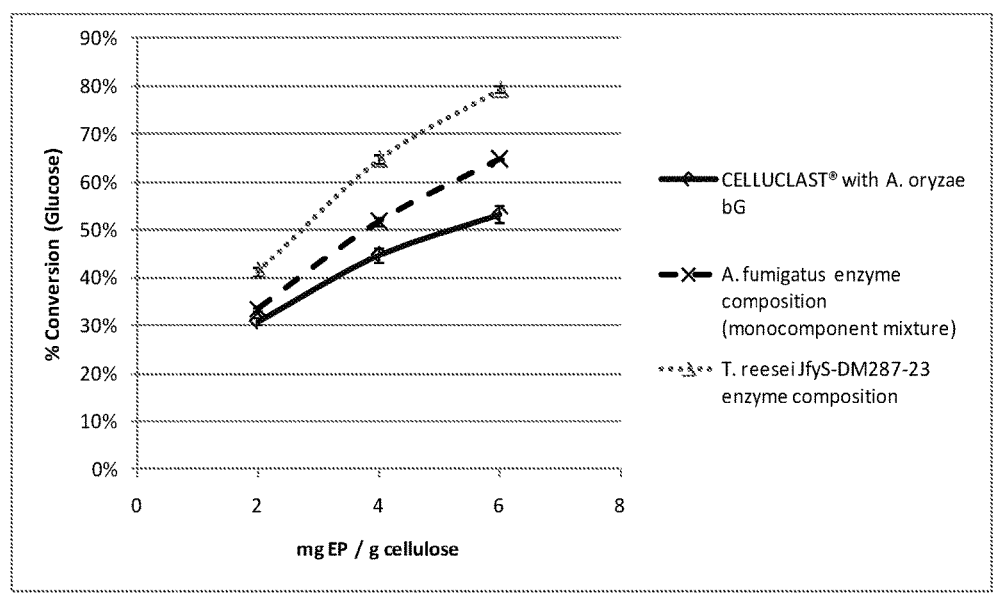
FIG. 7 shows a comparison of an enzyme composition of a *Trichoderma reesei* strain expressing an *Aspergillus fumigatus* cellobiohydrolase I, *A. fumigatus* cellobiohydrolase II, *A. fumigatus* beta-glucosidase, and *A. fumigatus* GH61B polypeptide with a *Trichoderma reesei*-based cellulase composition or an *Aspergillus fumigatus* enzyme composition in the hydrolysis of pretreated corn stover.

The results shown in FIG. 7 demonstrated that the enzyme composition of *T. reesei* JfyS-DM-23 expressing *A. fumigatus* cellobiohydrolase I, *A. fumigatus* cellobiohydrolase II, *A. fumigatus* beta-glucosidase, and *A. fumigatus* GH61B polypeptide and the *Aspergillus fumigatus* enzyme composition (monocomponent mixture) produced significantly higher hydrolysis than the *Trichoderma reesei*-based cellulase composition at all three loadings. In addition, the enzyme composition of *T. reesei* JfyS-DM-23 expressing *A. fumigatus* cellobiohydrolase I, *A. fumigatus* cellobiohydrolase II, *A. fumigatus* beta-glucosidase, and *A. fumigatus* GH61B polypeptide produced higher hydrolysis than the *Aspergillus fumigatus* enzyme composition (monocomponent mixture) at all enzyme loadings.

Example 18: PCS Hydrolysis Assay Comparing an *Aspergillus fumigatus* Wild-Type Enzyme Composition with a *Trichoderma reesei*-Based Cellulase Composition The *Aspergillus fumigatus* wild-type enzyme composition (Example 16) was compared to the *Trichoderma reesei*-based cellulase composition (CELLUCLAST™ 1.5L FG; Novozymes A/S, Bagsværd, Denmark replaced with 5% *Aspergillus oryzae* beta-glucosidase) using milled unwashed PCS at 50° C. In addition, the *Aspergillus fumigatus* wild-type enzyme composition was replaced with 5% *Aspergillus fumigatus* beta-glucosidase. The *Aspergillus fumigatus* wild-type enzyme composition and *Trichoderma reesei*-based cellulase composition were used at 2.0, 4.0, and 6.0 mg protein per g cellulose, and the *Aspergillus fumigatus* wild-type enzyme composition replaced with 5% *Aspergillus fumigatus* beta-glucosidase was used at 2.0 and 4.0 mg protein per g cellulose.

The assay was performed as described in Example 13. The 1 ml reactions with 5% milled unwashed PCS were conducted for 72 hours in 50 mM sodium acetate pH 5.0 buffer containing 1 mM manganese sulfate. All reactions were performed in triplicate and involved single mixing at the beginning of hydrolysis.

Figure 8:
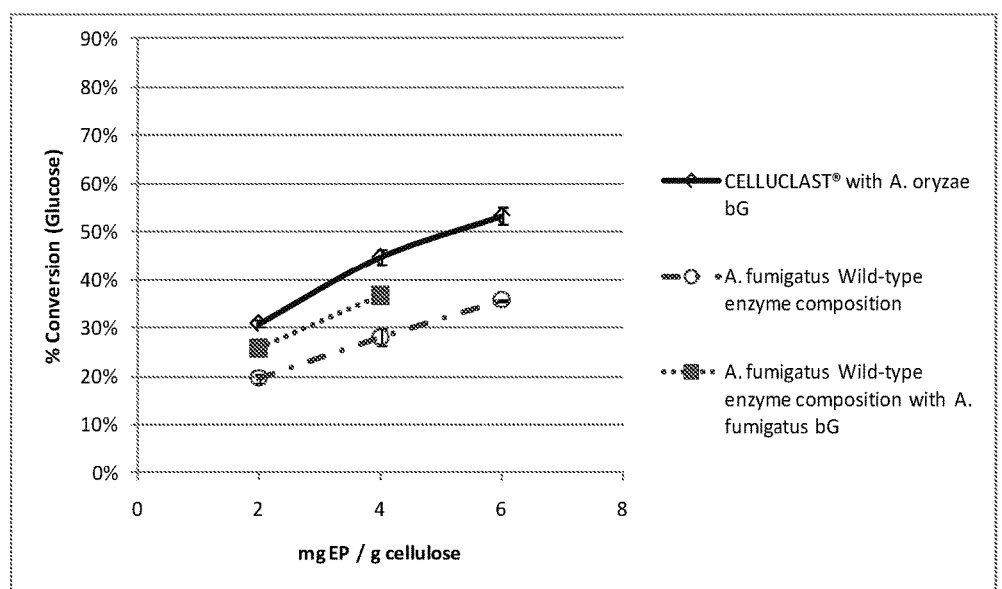
FIG. 8 shows a comparison of an *Aspergillus fumigatus* wild-type enzyme composition with a *Trichoderma reesei*-based cellulase composition in the hydrolysis of pretreated corn stover.

The results shown in FIG. 8 demonstrated that the *Trichoderma reesei*-based cellulase composition had significantly higher hydrolysis than the *Aspergillus fumigatus* wild-type composition and the *Aspergillus fumigatus* wild-type composition replaced with 5% *Aspergillus fumigatus* beta-glucosidase. The replacement of the *Aspergillus fumigatus* wild-type composition with *Aspergillus fumigatus* beta-glucosidase significantly increased cellulose hydrolysis above that of the *Aspergillus fumigatus* wild-type composition alone but both mixtures produced significantly less hydrolysis than the *Trichoderma reesei*-based cellulase composition.

The present invention is further described by the following numbered paragraphs:

[1] A recombinant *Trichoderma* host cell, comprising polynucleotides encoding: (i) an *Aspergillus fumigatus* cellobiohydrolase I; (ii) an *Aspergillus fumigatus* cellobiohydrolase II; (iii) an *Aspergillus fumigatus* beta-glucosidase; and (iv) an *Aspergillus fumigatus* GH61 polypeptide having cellulolytic enhancing activity; or homologs thereof.

[2] The recombinant *Trichoderma* host cell of paragraph 1, wherein the *Aspergillus fumigatus* cellobiohydrolase I or homolog thereof is selected from the group consisting of: (i) a cellobiohydrolase I comprising or consisting of the mature polypeptide of SEQ ID NO: 2; (ii) a cellobiohydrolase I comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 2; (iii) a cellobiohydrolase I encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 1; and (iv) a cellobiohydrolase I encoded by a polynucleotide that hybridizes under at least high stringency conditions, e.g., at least very high stringency conditions, with the mature polypeptide coding sequence of SEQ ID NO: 1 or the full-length complement thereof.

[3] The recombinant *Trichoderma* host cell of paragraph 1 or 2, wherein the *Aspergillus fumigatus* cellobiohydrolase II or homolog thereof is selected from the group consisting of: (i) a cellobiohydrolase II comprising or consisting of the mature polypeptide of SEQ ID NO: 4; (ii) a cellobiohydrolase II comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 4; (iii) a cellobiohydrolase II encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 3; and (iv) a cellobiohydrolase II encoded by a polynucleotide that hybridizes under at least high stringency conditions, e.g., at least very high stringency conditions, with the mature polypeptide coding sequence of SEQ ID NO: 3 or the full-length complement thereof.

[4] The recombinant *Trichoderma* host cell of any of paragraphs 1-3, wherein the *Aspergillus fumigatus* beta-glucosidase or homolog thereof is selected from the group consisting of: (i) a beta-glucosidase comprising or consisting of the mature polypeptide of SEQ ID NO: 6; (ii) a beta-glucosidase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 6; (iii) a beta-glucosidase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 5; and (iv) a beta-glucosidase encoded by a polynucleotide that hybridizes under at least high stringency conditions, e.g., at least very high stringency conditions, with the mature polypeptide coding sequence of SEQ ID NO: 5 or the full-length complement thereof.

[5] The recombinant *Trichoderma* host cell of any of paragraphs 1-4, wherein the *Aspergillus fumigatus* GH61 polypeptide having cellulolytic enhancing activity or homolog thereof is selected from the group consisting of: (i) a GH61 polypeptide having cellulolytic enhancing activity comprising or consisting of the mature polypeptide of SEQ ID NO: 8; (ii) a GH61 polypeptide having cellulolytic enhancing activity comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, sequence identity to the mature polypeptide of SEQ ID NO: 8; (iii) a GH61 polypeptide having cellulolytic enhancing activity encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 7; and (iv) a GH61 polypeptide having cellulolytic enhancing activity encoded by a polynucleotide that hybridizes under at least high stringency conditions, e.g., at least very high stringency conditions, with the mature polypeptide coding sequence of SEQ ID NO: 7 or the full-length complement thereof.

[6] The recombinant *Trichoderma* host cell of any of paragraphs 1-5, which further comprises one or more polynucleotides encoding one or more enzymes selected from the group consisting of: (i) an *Aspergillus fumigatus* endoglucanase I; (ii) an *Aspergillus fumigatus* endoglucanase II; (iii) an *Aspergillus fumigatus* xylanase; (iv) an *Aspergillus fumigatus* beta-xylosidase; and (v) an *Aspergillus fumigatus* swollenin.

[7] The recombinant *Trichoderma* host cell of paragraph 6, wherein the *Aspergillus fumigatus* endoglucanase I or homolog thereof is selected from the group consisting of: (i) an endoglucanase I comprising or consisting of the mature polypeptide of SEQ ID NO: 10; (ii) an endoglucanase I comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 10; (iii) an endoglucanase I encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 9; and (iv) an endoglucanase I encoded by a polynucleotide that hybridizes under at least high stringency conditions, e.g., at least very high stringency conditions, with the mature polypeptide coding sequence of SEQ ID NO: 9 or the full-length complement thereof.

[8] The recombinant *Trichoderma* host cell of paragraph 6 or 7, wherein the *Aspergillus fumigatus* endoglucanase II or homolog thereof is selected from the group consisting of: (i) an *Aspergillus fumigatus* endoglucanase II comprising or consisting of the mature polypeptide of SEQ ID NO: 12; (ii) an endoglucanase II comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 12; (iii) an endoglucanase II encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 11; and (iv) an endoglucanase II encoded by a polynucleotide that hybridizes under at least high stringency conditions, e.g., at least very high stringency conditions, with the mature polypeptide coding sequence of SEQ ID NO: 11 or the full-length complement thereof.

[9] The recombinant *Trichoderma* host cell of any of paragraphs 6-8, wherein the *Aspergillus fumigatus* xylanase or homolog thereof is selected from the group consisting of: (i) an *Aspergillus fumigatus* xylanase comprising or consisting of the mature polypeptide of SEQ ID NO: 14, SEQ ID NO: 16, or SEQ ID NO: 18; (ii) a xylanase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 14, SEQ ID NO: 16, or SEQ ID NO: 18; (iii) a xylanase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 13, SEQ ID NO: 15, or SEQ ID NO: 17; and (iv) a xylanase encoded by a polynucleotide that hybridizes under at least high stringency conditions, e.g., at least very high stringency conditions, with the mature polypeptide coding sequence of SEQ ID NO: 13, SEQ ID NO: 15, or SEQ ID NO: 17; or the full-length complement thereof.

[10] The recombinant *Trichoderma* host cell of any of paragraphs 6-9, wherein the *Aspergillus fumigatus* beta-xylosidase or homolog thereof is selected from the group consisting of: (i) a beta-xylosidase comprising or consisting of the mature polypeptide of SEQ ID NO: 20; (ii) a beta-xylosidase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 20; (iii) a beta-xylosidase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 19; and (iv) a beta-xylosidase encoded by a polynucleotide that hybridizes under at least high stringency conditions, e.g., at least very high stringency conditions, with the mature polypeptide coding sequence of SEQ ID NO: 19 or the full-length complement thereof.

[11] The recombinant *Trichoderma* host cell of any of paragraphs 6-10, wherein the *Aspergillus fumigatus* swollenin or homolog thereof is selected from the group consisting of: (i) a swollenin comprising or consisting of the mature polypeptide of SEQ ID NO: 22; (ii) a swollenin comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 22; (iii) a swollenin encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 21; and (iv) a swollenin encoded by a polynucleotide that hybridizes under at least high stringency conditions, e.g., at least very high stringency conditions, with the mature polypeptide coding sequence of SEQ ID NO: 21 or the full-length complement thereof.

[12] The recombinant *Trichoderma* host cell of any of paragraphs 1-11, which is selected from the group consisting of *Trichoderma harzianum*, *Trichoderma koningii*, *Trichoderma longibrachiatum*, *Trichoderma reesei*, and *Trichoderma viride*.

[13] The recombinant *Trichoderma* host cell of any of paragraphs 1-11, which is *Trichoderma reesei*.

[14] The recombinant *Trichoderma* host cell of any of paragraphs 1-13, wherein one or more of the cellulase genes, one or more of hemicellulase genes, or a combination thereof, endogenous to the *Trichoderma* host cell have been inactivated.

[15] The recombinant *Trichoderma* host cell of paragraph 14, wherein a *Trichoderma* cellobiohydrolase I gene or a homolog thereof has been inactivated.

[16] The recombinant *Trichoderma* host cell of paragraph 15, wherein the *Trichoderma* cellobiohydrolase I gene encodes the mature polypeptide of SEQ ID NO: 24 or a homolog thereof.

[17] The recombinant *Trichoderma* host cell of paragraph 16, wherein the *Trichoderma* cellobiohydrolase I gene homolog is selected from the group consisting of: (i) a cellobiohydrolase I comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 24; (ii) a cellobiohydrolase I encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 23; and (iii) a cellobiohydrolase I encoded by a polynucleotide that hybridizes under at least high stringency conditions, e.g., at least very high stringency conditions, with the mature polypeptide coding sequence of SEQ ID NO: 23 or the full-length complement thereof.

[18] The recombinant *Trichoderma* host cell of any of paragraphs 14-17, wherein a *Trichoderma* cellobiohydrolase II gene or a homolog thereof has been inactivated.

[19] The recombinant *Trichoderma* host cell of paragraph 18, wherein the *Trichoderma* cellobiohydrolase II gene encodes the mature polypeptide of SEQ ID NO: 26 or a homolog thereof.

[20] The recombinant *Trichoderma* host cell of paragraph 19, wherein the *Trichoderma* cellobiohydrolase II gene homolog is selected from the group consisting of: (i) a cellobiohydrolase II comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 26; (ii) a cellobiohydrolase II encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 25; and (iii) a cellobiohydrolase II encoded by a polynucleotide that hybridizes under at least high stringency conditions, e.g., at least very high stringency conditions, with the mature polypeptide coding sequence of SEQ ID NO: 25 or the full-length complement thereof.

[21] The recombinant *Trichoderma* host cell of any of paragraphs 14-20, wherein a *Trichoderma* beta-glucosidase gene or a homolog thereof has been inactivated.

[22] The recombinant *Trichoderma* host cell of paragraph 21, wherein the *Trichoderma* beta-glucosidase gene encodes the mature polypeptide of SEQ ID NO: 28 or a homolog thereof.

[23] The recombinant *Trichoderma* host cell of paragraph 22, wherein the *Trichoderma* beta-glucosidase gene homolog is selected from the group consisting of: (i) a beta-glucosidase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 28; (ii) a beta-glucosidase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 27; and (iii) a beta-glucosidase encoded by a polynucleotide that hybridizes under at least high stringency conditions, e.g., at least very high stringency conditions, with the mature polypeptide coding sequence of SEQ ID NO: 27 or the full-length complement thereof.

[24] The recombinant *Trichoderma* host cell of any of paragraphs 14-23, wherein a *Trichoderma* endoglucanase I gene or a homolog thereof has been inactivated.

[25] The recombinant *Trichoderma* host cell of paragraph 24, wherein the *Trichoderma* endoglucanase I gene encodes the mature polypeptide of SEQ ID NO: 30 or a homolog thereof.

[26] The recombinant *Trichoderma* host cell of paragraph 25, wherein the *Trichoderma* endoglucanase I gene homolog is selected from the group consisting of: (i) an endoglucanase I comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 30; (ii) an endoglucanase I encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 29; and (iii) an endoglucanase I encoded by a polynucleotide that hybridizes under at least high stringency conditions, e.g., at least very high stringency conditions, with the mature polypeptide coding sequence of SEQ ID NO: 29 or the full-length complement thereof.

[27] The recombinant *Trichoderma* host cell of any of paragraphs 14-26, wherein a *Trichoderma* endoglucanase II gene or a homolog thereof has been inactivated.

[28] The recombinant *Trichoderma* host cell of paragraph 27, wherein the *Trichoderma* endoglucanase II gene encodes the mature polypeptide of SEQ ID NO: 32 or a homolog thereof.

[29] The recombinant *Trichoderma* host cell of paragraph 28, wherein the *Trichoderma* endoglucanase II gene homolog is selected from the group consisting of: (i) an endoglucanase II comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 32; (ii) an endoglucanase II encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 31; and (iii) an endoglucanase II encoded by a polynucleotide that hybridizes under at least high stringency conditions, e.g., at least very high stringency conditions, with the mature polypeptide coding sequence of SEQ ID NO: 31 or the full-length complement thereof.

[30] The recombinant *Trichoderma* host cell of any of paragraphs 14-29, wherein a *Trichoderma* xylanase I gene or a homolog thereof has been inactivated.

[31] The recombinant *Trichoderma* host cell of paragraph 30, wherein the *Trichoderma* xylanase I gene encodes the mature polypeptide of SEQ ID NO: 34 or a homolog thereof.

[32] The recombinant *Trichoderma* host cell of paragraph 31, wherein the *Trichoderma* beta xylanase I gene homolog is selected from the group consisting of: (i) a xylanase I comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 34; (ii) a xylanase I encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 33; and (iii) a xylanase I encoded by a polynucleotide that hybridizes under at least high stringency conditions, e.g., at least very high stringency conditions, with the mature polypeptide coding sequence of SEQ ID NO: 33 or the full-length complement thereof.

[33] The recombinant *Trichoderma* host cell of any of paragraphs 14-32, wherein a *Trichoderma* xylanase II gene or a homolog thereof has been inactivated.

[34] The recombinant *Trichoderma* host cell of paragraph 33, wherein the *Trichoderma* xylanase II gene encodes the mature polypeptide of SEQ ID NO: 36 or a homolog thereof.

[35] The recombinant *Trichoderma* host cell of paragraph 34, wherein the *Trichoderma* xylanase II gene homolog is selected from the group consisting of: (i) a xylanase II comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 36; (ii) a xylanase II encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 35; and (iii) a xylanase II encoded by a polynucleotide that hybridizes under at least high stringency conditions, e.g., at least very high stringency conditions, with the mature polypeptide coding sequence of SEQ ID NO: 35 or the full-length complement thereof.

[36] The recombinant *Trichoderma* host cell of any of paragraphs 14-35, wherein a *Trichoderma* xylanase III gene or a homolog thereof has been inactivated.

[37] The recombinant *Trichoderma* host cell of paragraph 36, wherein the *Trichoderma* xylanase III gene encodes the mature polypeptide of SEQ ID NO: 38 or a homolog thereof.

[38] The recombinant *Trichoderma* host cell of paragraph 37, wherein the *Trichoderma* xylanase III gene homolog is selected from the group consisting of: (i) a xylanase III comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 38; (ii) a xylanase III encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 37; and (iii) a xylanase III encoded by a polynucleotide that hybridizes under at least high stringency conditions, e.g., at least very high stringency conditions, with the mature polypeptide coding sequence of SEQ ID NO: 37 or the full-length complement thereof.

[39] The recombinant *Trichoderma* host cell of any of paragraphs 14-38, wherein a *Trichoderma* beta-xylosidase gene or a homolog thereof has been inactivated.

[40] The recombinant *Trichoderma* host cell of paragraph 39, wherein the *Trichoderma* beta-xylosidase gene encodes the mature polypeptide of SEQ ID NO: 40 or a homolog thereof.

[41] The recombinant *Trichoderma* host cell of paragraph 40, wherein the *Trichoderma* beta-xylosidase gene homolog is selected from the group consisting of: (i) a beta-xylosidase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 40; (ii) a beta-xylosidase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 39; and (iii) a beta-xylosidase encoded by a polynucleotide that hybridizes under at least high stringency conditions, e.g., at least very high stringency conditions, with the mature polypeptide coding sequence of SEQ ID NO: 39 or the full-length complement thereof.

[42] The recombinant *Trichoderma* host cell of any of paragraphs 14-41, wherein a *Trichoderma* swollenin gene or a homolog thereof has been inactivated.

[43] The recombinant *Trichoderma* host cell of paragraph 42, wherein the *Trichoderma* swollenin gene encodes the mature polypeptide of SEQ ID NO: 42 or a homolog thereof.

[44] The recombinant *Trichoderma* host cell of paragraph 43, wherein the *Trichoderma* swollenin gene homolog is selected from the group consisting of: (i) a swollenin comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 42; (ii) a swollenin encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 41; and (iii) a swollenin encoded by a polynucleotide that hybridizes under at least high stringency conditions, e.g., at least very high stringency conditions, with the mature polypeptide coding sequence of SEQ ID NO: 41 or the full-length complement thereof.

[45] A method of producing an enzyme composition, comprising: cultivating the host cell of any of paragraphs 1-44 under conditions conducive for production of the enzyme composition.

[46] The method of paragraph 45, further comprising recovering the enzyme composition.

[47] An enzyme composition comprising a recovered fermentation broth of the recombinant *Trichoderma* host cell of any of paragraphs 1-44.

[48] The enzyme composition of paragraph 47, which has one or more components of the fermentation broth removed.

[49] The enzyme composition of paragraph 47, which has no components of the fermentation broth removed.

[50] A process for degrading a cellulosic material, comprising: treating the cellulosic material with the enzyme composition of any of paragraphs 47-49.

[51] The process of paragraph 50, wherein the cellulosic material is pretreated.

[52] The process of paragraph 50 or 51, further comprising recovering the degraded cellulosic material.

[53] The process of paragraph 52, wherein the degraded cellulosic material is a sugar.

[54] The process of paragraph 53, wherein the sugar is selected from the group consisting of glucose, xylose, mannose, galactose, and arabinose.

[55] A process for producing a fermentation product, comprising: (a) saccharifying a cellulosic material with the enzyme composition of any of paragraphs 46-48; (b) fermenting the saccharified cellulosic material with one or more fermenting microorganisms to produce the fermentation product; and (c) recovering the fermentation product from the fermentation.

[56] The process of paragraph 55, wherein the cellulosic material is pretreated.

[57] The process of paragraph 55 or 56, wherein steps (a) and (b) are performed simultaneously in a simultaneous saccharification and fermentation.

[58] The process of any of paragraphs 55-57, wherein the fermentation product is an alcohol, an alkane, a cycloalkane, an alkene, an amino acid, a gas, isoprene, a ketone, an organic acid, or polyketide.

[59] A process of fermenting a cellulosic material, comprising: fermenting the cellulosic material with one or more fermenting microorganisms, wherein the cellulosic material is saccharified with the enzyme composition of any of paragraphs 47-49.

[60] The process of paragraph 59, wherein the fermenting of the cellulosic material produces a fermentation product.

[61] The process of paragraph 60, further comprising recovering the fermentation product from the fermentation.

[62] The process of paragraph 60 or 61, wherein the fermentation product is an alcohol, an alkane, a cycloalkane, an alkene, an amino acid, a gas, isoprene, a ketone, an organic acid, or polyketide.

[63] The process of any of paragraphs 59-62, wherein the cellulosic material is pretreated before saccharification.

[64] The enzyme composition of paragraphs 47-49, further comprising a *Trichoderma* endoglucanase I, a *Trichoderma* endoglucanase II, or a *Trichoderma* endoglucanase I and a a *Trichoderma* endoglucanase II.

[65] The enzyme composition of paragraph 64, wherein the *Trichoderma* endoglucanase I is a *Trichoderma reesei* endoglucanase I.

[66] The enzyme composition of paragraph 64, wherein the *Trichoderma* endoglucanase II is a *Trichoderma reesei* endoglucanase II.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. An enzyme composition comprising a recovered fermentation broth of a recombinant *Trichoderma* host cell, wherein the recombinant *Trichoderma* host cell comprises polynucleotides encoding: (i) an *Aspergillus fumigatus* cellobiohydrolase I; (ii) an *Aspergillus fumigatus* cellobiohydrolase II; (iii) an *Aspergillus fumigatus* beta-glucosidase; (iv) an *Aspergillus fumigatus* GH61 polypeptide having cellulolytic enhancing activity; (v) an *Aspergillus fumigatus* xylanase; and (vi) an *Aspergillus fumigatus* beta-xylosidase; or homologs thereof;

wherein the *Aspergillus fumigatus* cellobiohydrolase I or homolog thereof is selected from the group consisting of:
(i) a cellobiohydrolase I comprising the mature polypeptide of SEQ ID NO: 2;
(ii) a cellobiohydrolase I comprising an amino acid sequence having at least 95% sequence identity to the mature polypeptide of SEQ ID NO: 2;
(iii) a cellobiohydrolase I encoded by a polynucleotide comprising a nucleotide sequence having at least 95% sequence identity to the mature polypeptide coding sequence of SEQ ID NO: 1; and
(iv) a cellobiohydrolase I encoded by a polynucleotide that hybridizes under very high stringency conditions with the mature polypeptide coding sequence of SEQ ID NO: 1 or the full-length complement thereof;

wherein the *Aspergillus fumigatus* cellobiohydrolase II or homolog thereof is selected from the group consisting of:
(i) a cellobiohydrolase II comprising the mature polypeptide of SEQ ID NO: 4;
(ii) a cellobiohydrolase II comprising an amino acid sequence having at least 95% sequence identity to the mature polypeptide of SEQ ID NO: 4;
(iii) a cellobiohydrolase II encoded by a polynucleotide comprising a nucleotide sequence having at least 95% sequence identity to the mature polypeptide coding sequence of SEQ ID NO: 3; and
(iv) a cellobiohydrolase II encoded by a polynucleotide that hybridizes under very high stringency conditions with the mature polypeptide coding sequence of SEQ ID NO: 3 or the full-length complement thereof;

wherein the *Aspergillus fumigatus* beta-glucosidase or homolog thereof is selected from the group consisting of:
(i) a beta-glucosidase comprising the mature polypeptide of SEQ ID NO: 6;

(ii) a beta-glucosidase comprising an amino acid sequence having at least 95% sequence identity to the mature polypeptide of SEQ ID NO: 6;
(iii) a beta-glucosidase encoded by a polynucleotide comprising a nucleotide sequence having at least 95% sequence identity to the mature polypeptide coding sequence of SEQ ID NO: 5; and
(iv) a beta-glucosidase encoded by a polynucleotide that hybridizes under very high stringency conditions with the mature polypeptide coding sequence of SEQ ID NO: 5 or the full-length complement thereof;
wherein the *Aspergillus fumigatus* GH61 polypeptide having cellulolytic enhancing activity or homolog thereof is selected from the group consisting of:
(i) a GH61 polypeptide having cellulolytic enhancing activity comprising the mature polypeptide of SEQ ID NO: 8;
(ii) a GH61 polypeptide having cellulolytic enhancing activity comprising an amino acid sequence having at least 95% sequence identity to the mature polypeptide of SEQ ID NO: 8;
(iii) a GH61 polypeptide having cellulolytic enhancing activity encoded by a polynucleotide comprising a nucleotide sequence having at least 95% sequence identity to the mature polypeptide coding sequence of SEQ ID NO: 7; and
(iv) a GH61 polypeptide having cellulolytic enhancing activity encoded by a polynucleotide that hybridizes under very high stringency conditions with the mature polypeptide coding sequence of SEQ ID NO: 7 or the full-length complement thereof;
wherein the *Aspergillus fumigatus* xylanase or homolog thereof is selected from the group consisting of:
(i) an *Aspergillus fumigatus* xylanase comprising the mature polypeptide of SEQ ID NO: 14, SEQ ID NO: 16, or SEQ ID NO: 18;
(ii) a xylanase comprising an amino acid sequence having at least 95% sequence identity to the mature polypeptide of SEQ ID NO: 14, SEQ ID NO: 16, or SEQ ID NO: 18;
(iii) a xylanase encoded by a polynucleotide comprising a nucleotide sequence having at least 95% sequence identity to the mature polypeptide coding sequence of SEQ ID NO: 13, SEQ ID NO: 15, or SEQ ID NO: 17; and
(iv) a xylanase encoded by a polynucleotide that hybridizes under very high stringency conditions with the mature polypeptide coding sequence of SEQ ID NO: 13, SEQ ID NO: 15, or SEQ ID NO: 17; or the full-length complement thereof;
wherein the *Aspergillus fumigatus* beta-xylosidase or homolog thereof is selected from the group consisting of:
(i) a beta-xylosidase comprising the mature polypeptide of SEQ ID NO: 20;
(ii) a beta-xylosidase comprising an amino acid sequence having at least 95% sequence identity to the mature polypeptide of SEQ ID NO: 20;
(iii) a beta-xylosidase encoded by a polynucleotide comprising a nucleotide sequence having at least 95% sequence identity to the mature polypeptide coding sequence of SEQ ID NO: 19; and
(iv) a beta-xylosidase encoded by a polynucleotide that hybridizes under very high stringency conditions with the mature polypeptide coding sequence of SEQ ID NO: 19 or the full-length complement thereof; and wherein very high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 70° C.

2. The enzyme composition of claim 1, wherein the recombinant *Trichoderma* host cell further comprises one or more polynucleotides encoding one or more enzymes selected from the group consisting of: (i) an *Aspergillus fumigatus* endoglucanase I; (ii) an *Aspergillus fumigatus* endoglucanase II; and (iii) an *Aspergillus fumigatus* swollenin;
wherein the *Aspergillus fumigatus* endoglucanase I or homolog thereof is selected from the group consisting of:
(i) an endoglucanase I comprising the mature polypeptide of SEQ ID NO: 10;
(ii) an endoglucanase I comprising an amino acid sequence having at least 95% sequence identity to the mature polypeptide of SEQ ID NO: 10;
(iii) an endoglucanase I encoded by a polynucleotide comprising a nucleotide sequence having at least 95% sequence identity to the mature polypeptide coding sequence of SEQ ID NO: 9; and
(iv) an endoglucanase I encoded by a polynucleotide that hybridizes under very high stringency conditions with the mature polypeptide coding sequence of SEQ ID NO: 9 or the full-length complement thereof;
wherein the *Aspergillus fumigatus* endoglucanase II or homolog thereof is selected from the group consisting of:
(i) an *Aspergillus fumigatus* endoglucanase II comprising the mature polypeptide of SEQ ID NO: 12;
(ii) an endoglucanase II comprising an amino acid sequence having at least 95% sequence identity to the mature polypeptide of SEQ ID NO: 12;
(iii) an endoglucanase II encoded by a polynucleotide comprising a nucleotide sequence having at least 95% sequence identity to the mature polypeptide coding sequence of SEQ ID NO: 11; and
(iv) an endoglucanase II encoded by a polynucleotide that hybridizes under very high stringency conditions with the mature polypeptide coding sequence of SEQ ID NO: 11 or the full-length complement thereof;
(i) wherein the *Aspergillus fumigatus* swollenin or homolog thereof is selected from the group consisting of:
(i) a swollenin comprising the mature polypeptide of SEQ ID NO: 22;
(ii) a swollenin comprising an amino acid sequence having at least 95% sequence identity to the mature polypeptide of SEQ ID NO: 22;
(iii) a swollenin encoded by a polynucleotide comprising a nucleotide sequence having at least 95% sequence identity to the mature polypeptide coding sequence of SEQ ID NO: 21; and
(iv) a swollenin encoded by a polynucleotide that hybridizes under very high stringency conditions with the mature polypeptide coding sequence of SEQ ID NO: 21 or the full-length complement thereof; and
wherein very high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 70° C.

3. The enzyme composition of claim 1, wherein the recombinant *Trichoderma* host cell is selected from the group consisting of *Trichoderma harzianum, Trichoderma koningii, Trichoderma longibrachiatum, Trichoderma reesei*, and *Trichoderma viride*.

4. The enzyme composition of claim 1, wherein the recombinant *Trichoderma* host cell is *Trichoderma reesei*.

5. A process for degrading a cellulosic material, comprising: treating the cellulosic material with the enzyme composition of claim 1, and optionally recovering the degraded cellulosic material.

6. The process of claim 5, wherein the cellulosic material is pretreated.

7. The process of claim 5, wherein the degraded cellulosic material is a sugar.

8. The process of claim 7, wherein the sugar is selected from the group consisting of glucose, xylose, mannose, galactose, and arabinose.

9. A process for producing a fermentation product, comprising:
   (a) saccharifying a cellulosic material with the enzyme composition of claim 1;
   (b) fermenting the saccharified cellulosic material with one or more fermenting microorganisms to produce the fermentation product; and
   (c) recovering the fermentation product from the fermentation.

10. The process of claim 9, wherein the cellulosic material is pretreated.

11. The process of claim 9, wherein steps (a) and (b) are performed simultaneously in a simultaneous saccharification and fermentation.

12. The process of claim 9, wherein the fermentation product is an alcohol, an alkane, a cycloalkane, an alkene, an amino acid, a gas, isoprene, a ketone, an organic acid, or polyketide.

13. A process of fermenting a cellulosic material, comprising: fermenting the cellulosic material with one or more fermenting microorganisms, wherein the cellulosic material is saccharified with the enzyme composition of claim 1.

14. The process of claim 13, wherein the cellulosic material is pretreated before saccharification.

15. The process of claim 13, wherein the fermenting of the cellulosic material produces a fermentation product.

16. The process of claim 15, further comprising recovering the fermentation product from the fermentation.

17. The process of claim 16, wherein the fermentation product is an alcohol, an alkane, a cycloalkane, an alkene, an amino acid, a gas, isoprene, a ketone, an organic acid, or polyketide.

* * * * *

SEQUENCE LISTING

```
<160> NUMBER OF SEQ ID NOS: 86

<210> SEQ ID NO 1
<211> LENGTH: 1599
<212> TYPE: DNA
<213> ORGANISM: Aspergillus fumigatus

<400> SEQUENCE: 1
atgctggcct ccaccttctc ctaccgcatg tacaagaccg cgctcatcct ggccgccctt      60
ctgggctctg gccaggctca gcaggtcggt acttcccagg cggaagtgca tccgtccatg     120
acctggcaga gctgcacggc tggcggcagc tgcaccacca acaacggcaa ggtggtcatc     180
gacgcgaact ggcgttgggt gcacaaagtc ggcgactaca ccaactgcta caccggcaac     240
acctgggaca cgactatctg ccctgacgat gcgacctgcg catccaactg cgcccttgag     300
ggtgccaact acgaatccac ctatggtgtg accgccagcg gcaattccct ccgcctcaac     360
ttcgtcacca ccagccagca gaagaacatt ggctcgcgtc tgtacatgat gaaggacgac     420
tcgacctacg agatgtttaa gctgctgaac caggagttca ccttcgatgt cgatgtctcc     480
aacctcccct gcggtctcaa cggtgctctg tactttgtcg ccatggacgc cgacggtggc     540
atgtccaagt acccaaccaa caaggccggt gccaagtacg gtactggata ctgtgactcg     600
cagtgccctc gcgacctcaa gttcatcaac ggtcaggcca acgtcgaagg gtggcagccc     660
tcctccaacg atgccaatgc gggtaccggc aaccacgggt cctgctgcgc ggagatggat     720
atctgggagg ccaacagcat ctccacggcc ttcacccccc atccgtgcga cacgcccggc     780
caggtgatgt gcaccggtga tgcctgcggt ggcacctaca gctccgaccg ctacggcggc     840
```

```
acctgcgacc ccgacggatg tgatttcaac tccttccgcc agggcaacaa gaccttctac    900
ggccctggca tgaccgtcga caccaagagc aagtttaccg tcgtcaccca gttcatcacc    960
gacgacggca cctccagcgg caccctcaag gagatcaagc gcttctacgt gcagaacggc   1020
aaggtgatcc ccaactcgga gtcgacctgg accggcgtca gcggcaactc catcaccacc   1080
gagtactgca ccgcccagaa gagcctgttc caggaccaga acgtcttcga aaagcacggc   1140
ggcctcgagg gcatgggtgc tgccctcgcc cagggtatgg ttctcgtcat gtccctgtgg   1200
gatgatcact cggccaacat gctctggctc gacagcaact acccgaccac tgcctcttcc   1260
accactcccg gcgtcgcccg tggtacctgc gacatctcct ccggcgtccc tgcggatgtc   1320
gaggcgaacc accccgacgc ctacgtcgtc tactccaaca tcaaggtcgg ccccatcggc   1380
tcgaccttca cagcggtgg ctcgaacccg gtggcggaa ccaccacgac aactaccacc   1440
cagcctacta ccaccacgac cacggctgga aaccctggcg gcaccggagt cgcacagcac   1500
tatggccagt gtggtggaat cggatggacc ggacccacaa cctgtgccag cccttatacc   1560
tgccagaagc tgaatgatta ttactctcag tgcctgtag                          1599
```

<210> SEQ ID NO 2
<211> LENGTH: 532
<212> TYPE: PRT
<213> ORGANISM: Aspergillus fumigatus

<400> SEQUENCE: 2

```
Met Leu Ala Ser Thr Phe Ser Tyr Arg Met Tyr Lys Thr Ala Leu Ile
1               5                   10                  15

Leu Ala Ala Leu Leu Gly Ser Gly Gln Ala Gln Val Gly Thr Ser
            20                  25                  30

Gln Ala Glu Val His Pro Ser Met Thr Trp Gln Ser Cys Thr Ala Gly
        35                  40                  45

Gly Ser Cys Thr Thr Asn Asn Gly Lys Val Val Ile Asp Ala Asn Trp
    50                  55                  60

Arg Trp Val His Lys Val Gly Asp Tyr Thr Asn Cys Tyr Thr Gly Asn
65                  70                  75                  80

Thr Trp Asp Thr Thr Ile Cys Pro Asp Asp Ala Thr Cys Ala Ser Asn
                85                  90                  95

Cys Ala Leu Glu Gly Ala Asn Tyr Glu Ser Thr Tyr Gly Val Thr Ala
            100                 105                 110

Ser Gly Asn Ser Leu Arg Leu Asn Phe Val Thr Ser Gln Gln Lys
        115                 120                 125

Asn Ile Gly Ser Arg Leu Tyr Met Met Lys Asp Asp Ser Thr Tyr Glu
    130                 135                 140

Met Phe Lys Leu Leu Asn Gln Glu Phe Thr Phe Asp Val Asp Val Ser
145                 150                 155                 160

Asn Leu Pro Cys Gly Leu Asn Gly Ala Leu Tyr Phe Val Ala Met Asp
                165                 170                 175

Ala Asp Gly Gly Met Ser Lys Tyr Pro Thr Asn Lys Ala Gly Ala Lys
            180                 185                 190

Tyr Gly Thr Gly Tyr Cys Asp Ser Gln Cys Pro Arg Asp Leu Lys Phe
        195                 200                 205

Ile Asn Gly Gln Ala Asn Val Glu Gly Trp Gln Pro Ser Ser Asn Asp
    210                 215                 220

Ala Asn Ala Gly Thr Gly Asn His Gly Ser Cys Cys Ala Glu Met Asp
225                 230                 235                 240
```

Ile Trp Glu Ala Asn Ser Ile Ser Thr Ala Phe Thr Pro His Pro Cys
            245                 250                 255

Asp Thr Pro Gly Gln Val Met Cys Thr Gly Asp Ala Cys Gly Gly Thr
        260                 265                 270

Tyr Ser Ser Asp Arg Tyr Gly Gly Thr Cys Asp Pro Asp Gly Cys Asp
        275                 280                 285

Phe Asn Ser Phe Arg Gln Gly Asn Lys Thr Phe Tyr Gly Pro Gly Met
        290                 295                 300

Thr Val Asp Thr Lys Ser Lys Phe Thr Val Val Thr Gln Phe Ile Thr
305                 310                 315                 320

Asp Asp Gly Thr Ser Ser Gly Thr Leu Lys Glu Ile Lys Arg Phe Tyr
                325                 330                 335

Val Gln Asn Gly Lys Val Ile Pro Asn Ser Glu Ser Thr Trp Thr Gly
            340                 345                 350

Val Ser Gly Asn Ser Ile Thr Thr Glu Tyr Cys Thr Ala Gln Lys Ser
        355                 360                 365

Leu Phe Gln Asp Gln Asn Val Phe Glu Lys His Gly Gly Leu Glu Gly
        370                 375                 380

Met Gly Ala Ala Leu Ala Gln Gly Met Val Leu Val Met Ser Leu Trp
385                 390                 395                 400

Asp Asp His Ser Ala Asn Met Leu Trp Leu Asp Ser Asn Tyr Pro Thr
                405                 410                 415

Thr Ala Ser Ser Thr Thr Pro Gly Val Ala Arg Gly Thr Cys Asp Ile
            420                 425                 430

Ser Ser Gly Val Pro Ala Asp Val Glu Ala Asn His Pro Asp Ala Tyr
        435                 440                 445

Val Val Tyr Ser Asn Ile Lys Val Gly Pro Ile Gly Ser Thr Phe Asn
450                 455                 460

Ser Gly Gly Ser Asn Pro Gly Gly Thr Thr Thr Thr Thr Thr Thr Thr
465                 470                 475                 480

Gln Pro Thr Thr Thr Thr Thr Ala Gly Asn Pro Gly Gly Thr Gly
                485                 490                 495

Val Ala Gln His Tyr Gly Gln Cys Gly Gly Ile Gly Trp Thr Gly Pro
            500                 505                 510

Thr Thr Cys Ala Ser Pro Tyr Thr Cys Gln Lys Leu Asn Asp Tyr Tyr
        515                 520                 525

Ser Gln Cys Leu
    530

<210> SEQ ID NO 3
<211> LENGTH: 1713
<212> TYPE: DNA
<213> ORGANISM: Aspergillus fumigatus

<400> SEQUENCE: 3
atgaagcacc ttgcatcttc catcgcattg actctactgt tgcctgccgt gcaggcccag     60
cagaccgtat ggggccaatg tatgttctgg ctgtcactgg aataagactg tatcaactgc    120
tgatatgctt ctaggtggcg gccaaggctg gtctggcccg acgagctgtg ttgccggcgc    180
agcctgtagc acactgaatc cctgtatgtt agatatcgtc ctgagtggag acttatactg    240
acttccttag actacgctca gtgtatcccg ggagccaccg cgacgtccac caccctcacg    300
acgacgacgg cggcgacgac gacatcccag accaccacca aacctaccac gactggtcca    360
actacatccg cacccaccgt gaccgcatcc ggtaacccct tcagcggcta ccagctgtat    420

```
gccaacccct actactcctc cgaggtccat actctggcca tgccttctct gcccagctcg    480
ctgcagccca aggctagtgc tgttgctgaa gtgccctcat ttgtttggct gtaagtggcc    540
ttatcccaat actgagacca actctctgac agtcgtagcg acgttgccgc caaggtgccc    600
actatgggaa cctacctggc cgacattcag gccaagaaca aggccggcgc caaccctcct    660
atcgctggta tcttcgtggt ctacgacttg ccggaccgtg actgcgccgc tctggccagt    720
aatggcgagt actcaattgc caacaacggt gtggccaact acaaggcgta cattgacgcc    780
atccgtgctc agctggtgaa gtactctgac gttcacacca tcctcgtcat cggtaggccg    840
tacacctccg ttgcgcgccg cctttctctg acatcttgca gaacccgaca gcttggccaa    900
cctggtgacc aacctcaacg tcgccaaatg cgccaatgcg cagagcgcct acctggagtg    960
tgtcgactat gctctgaagc agctcaacct gcccaacgtc gccatgtacc tcgacgcagg   1020
tatgcctcac ttcccgcatt ctgtatccct tccagacact aactcatcag gccatgcggg   1080
ctggctcgga tggcccgcca acttgggccc cgccgcaaca ctcttcgcca aagtctacac   1140
cgacgcgggt tcccccgcgg ctgttcgtgg cctggccacc aacgtcgcca actacaacgc   1200
ctggtcgctc agtacctgcc cctcctacac ccagggagac cccaactgcg acgagaagaa   1260
gtacatcaac gccatggcgc tcttctcaa ggaagccggc ttcgatgccc acttcatcat   1320
ggatacctgt aagtgcttat tccaatcgcc gatgtgtgcc gactaatcaa tgtttcagcc   1380
cggaatggcg tccagcccac gaagcaaaac gcctggggtg actggtgcaa cgtcatcggc   1440
accggcttcg gtgttcgccc ctcgactaac accggcgatc cgctccagga tgcctttgtg   1500
tggatcaagc ccgtggagaa gagtgatggc acgtccaact cgacttcccc ccggtatgac   1560
gcgcactgcg gatatagtga tgctctgcag cctgctcctg aggctggtac ttggttccag   1620
gtatgtcatc cattagccag atgagggata agtgactgac ggacctaggc ctactttgag   1680
cagcttctga ccaacgctaa cccgtccttt taa                                1713

<210> SEQ ID NO 4
<211> LENGTH: 454
<212> TYPE: PRT
<213> ORGANISM: Aspergillus fumigatus

<400> SEQUENCE: 4

Met Lys His Leu Ala Ser Ser Ile Ala Leu Thr Leu Leu Pro Ala
1               5                   10                  15

Val Gln Ala Gln Gln Thr Val Trp Gly Gln Cys Gly Gly Gln Gly Trp
            20                  25                  30

Ser Gly Pro Thr Ser Cys Val Ala Gly Ala Ala Cys Ser Thr Leu Asn
        35                  40                  45

Pro Tyr Tyr Ala Gln Cys Ile Pro Gly Ala Thr Ala Thr Ser Thr Thr
    50                  55                  60

Leu Thr Thr Thr Thr Ala Ala Thr Thr Thr Ser Gln Thr Thr Thr Lys
65                  70                  75                  80

Pro Thr Thr Thr Gly Pro Thr Thr Ser Ala Pro Thr Val Thr Ala Ser
                85                  90                  95

Gly Asn Pro Phe Ser Gly Tyr Gln Leu Tyr Ala Asn Pro Tyr Tyr Ser
            100                 105                 110

Ser Glu Val His Thr Leu Ala Met Pro Ser Leu Pro Ser Ser Leu Gln
        115                 120                 125

Pro Lys Ala Ser Ala Val Ala Glu Val Pro Ser Phe Val Trp Leu Asp
    130                 135                 140
```

Val Ala Ala Lys Val Pro Thr Met Gly Thr Tyr Leu Ala Asp Ile Gln
145                 150                 155                 160

Ala Lys Asn Lys Ala Gly Ala Asn Pro Pro Ile Ala Gly Ile Phe Val
            165                 170                 175

Val Tyr Asp Leu Pro Asp Arg Asp Cys Ala Ala Leu Ala Ser Asn Gly
        180                 185                 190

Glu Tyr Ser Ile Ala Asn Asn Gly Val Ala Asn Tyr Lys Ala Tyr Ile
    195                 200                 205

Asp Ala Ile Arg Ala Gln Leu Val Lys Tyr Ser Asp Val His Thr Ile
210                 215                 220

Leu Val Ile Glu Pro Asp Ser Leu Ala Asn Leu Val Thr Asn Leu Asn
225                 230                 235                 240

Val Ala Lys Cys Ala Asn Ala Gln Ser Ala Tyr Leu Glu Cys Val Asp
            245                 250                 255

Tyr Ala Leu Lys Gln Leu Asn Leu Pro Asn Val Ala Met Tyr Leu Asp
        260                 265                 270

Ala Gly His Ala Gly Trp Leu Gly Trp Pro Ala Asn Leu Gly Pro Ala
    275                 280                 285

Ala Thr Leu Phe Ala Lys Val Tyr Thr Asp Ala Gly Ser Pro Ala Ala
290                 295                 300

Val Arg Gly Leu Ala Thr Asn Val Ala Asn Tyr Asn Ala Trp Ser Leu
305                 310                 315                 320

Ser Thr Cys Pro Ser Tyr Thr Gln Gly Asp Pro Asn Cys Asp Glu Lys
            325                 330                 335

Lys Tyr Ile Asn Ala Met Ala Pro Leu Leu Lys Glu Ala Gly Phe Asp
        340                 345                 350

Ala His Phe Ile Met Asp Thr Ser Arg Asn Gly Val Gln Pro Thr Lys
    355                 360                 365

Gln Asn Ala Trp Gly Asp Trp Cys Asn Val Ile Gly Thr Gly Phe Gly
370                 375                 380

Val Arg Pro Ser Thr Asn Thr Gly Asp Pro Leu Gln Asp Ala Phe Val
385                 390                 395                 400

Trp Ile Lys Pro Gly Gly Glu Ser Asp Gly Thr Ser Asn Ser Thr Ser
            405                 410                 415

Pro Arg Tyr Asp Ala His Cys Gly Tyr Ser Asp Ala Leu Gln Pro Ala
        420                 425                 430

Pro Glu Ala Gly Thr Trp Phe Gln Ala Tyr Phe Glu Gln Leu Leu Thr
    435                 440                 445

Asn Ala Asn Pro Ser Phe
450

<210> SEQ ID NO 5
<211> LENGTH: 3060
<212> TYPE: DNA
<213> ORGANISM: Aspergillus fumigatus

<400> SEQUENCE: 5
atgagattcg gttggctcga ggtggccgct ctgacggccg cttctgtagc caatgcccag    60
gtttgtgatg ctttcccgtc attgtttcgg atatagttga caatagtcat ggaaataatc   120
aggaattggc tttctctcca ccattctacc cttcgccttg ggctgatggc cagggagagt   180
gggcagatgc ccatcgacgc gccgtcgaga tcgtttctca gatgacactg gcggagaagg   240
ttaaccttac aacgggtact gggtgggttg cgactttttt gttgacagtg agctttcttc   300
actgaccatc tacacagatg ggaaatggac cgatgcgtcg gtcaaaccgg cagcgttccc   360

```
aggtaagctt gcaattctgc aacaacgtgc aagtgtagtt gctaaaacgc ggtggtgcag    420
acttggtatc aactggggtc tttgtggcca ggattcccct ttgggtatcc gtttctgtga    480
gctatacccg cggagtcttt cagtccttgt attatgtgct gatgattgtc tctgtatagc    540
tgacctcaac tccgccttcc ctgctggtac taatgtcgcc gcgacatggg acaagacact    600
cgcctacctt cgtggcaagg ccatgggtga ggaattcaac gacaagggcg tggacatttt    660
gctggggcct gctgctggtc ctctcggcaa atacccggac ggcggcagaa tctgggaagg    720
cttctctcct gatccggttc tcactggtgt acttttcgcc gaaactatca agggtatcca    780
agacgcgggt gtgattgcta ctgccaagca ttacattctg aatgaacagg agcatttccg    840
acaggttggc gaggcccagg atatggttca acatcacg gagacgatca gctccaacgt    900
ggatgacaag accatgcacg agttgtacct tggtgagta gttgacactg caaatgagga    960
ccttgattga tttgactgac ctggaatgca ggcccttttgc agatgctgtg cgcggtaaga   1020
ttttccgtag acttgacctc gcgacgaaga aatcgctgac gaaccatcgt agctggcgtt   1080
ggcgctgtca tgtgttccta caatcaaatc aacaacagct acggttgtca aaacagtcaa   1140
actctcaaca agctcctcaa ggctgagctg gcttccaag gcttcgtcat gagtgactgg   1200
agcgctcacc acagcggtgt cggcgctgcc ctcgctgggt tggatatgtc gatgcctgga   1260
gacatttcct tcgacgacgg actctccttc tggggcacga acctaactgt cagtgttctt   1320
aacggcaccg ttccagcctg gcgtgtcgat gacatggctg ttcgtatcat gaccgcgtac   1380
tacaaggttg gtcgtgaccg tcttcgtatt cccctaact tcagctcctg gacccgggat   1440
gagtacggct gggagcattc tgctgtctcc gagggagcct ggaccaaggt gaacgacttc   1500
gtcaatgtgc agcgcagtca ctctcagatc atccgtgaga ttggtgccgc tagtacagtg   1560
ctcttgaaga acacgggtgc tcttcctttg accggcaagg aggttaaagt gggtgttctc   1620
ggtgaagacg ctggttccaa cccgtggggt gctaacggct gccccgaccg cggctgtgat   1680
aacggcactc ttgctatggc ctgggggtagt ggtactgcca acttcccttta ccttgtcacc   1740 cccgagcagg ctatccagcg agaggtcatc agcaacggcg gcaatgtctt tgctgtgact   1800
gataacgggg ctctcagcca gatggcagat gttgcatctc aatccaggtg agtgcgggct   1860
cttagaaaaa gaacgttctc tgaatgaagt ttttaacca ttgcgaacag cgtgtctttg   1920
gtgtttgtca acgccgactc tggagagggt ttcatcagtg tcgacggcaa cgagggtgac   1980
cgcaaaaatc tcactctgtg gaagaacggc gaggccgtca ttgacactgt tgtcagccac   2040
tgcaacaaca cgattgtggt tattcacagt gttgggcccg tcttgatcga ccggtggtat   2100 gataaccccca acgtcactgc catcatctgg gccggcttgc ccggtcagga gagtggcaac   2160
tccctggtcg acgtgctcta tggccgcgtc aaccccagcg ccaagacccc gttcacctgg   2220
ggcaagactc gggagtctta cggggctccc ttgctcaccg agcctaacaa tggcaatggt   2280
gctccccagg atgatttcaa cgagggcgtc ttcattgact accgtcactt tgacaagcgc   2340
aatgagaccc ccatttatga gtttggccat ggcttgagct acaccaccatt tggttactct   2400 caccttcggg ttcaggccct caatagttcg agttcggcat atgtcccgac tagcggagag   2460
accaagcctg cgccaaccta tggtgagatc ggtagtgccg ccgactacct gtatcccgag   2520
ggtctcaaaa gaattaccaa gtttatttac ccttggctca actcgaccga cctcgaggat   2580
tcttctgacg acccgaacta cggctgggag gactcggagt acattcccga aggcgctagg   2640
gatgggtctc ctcaaccccct cctgaaggct ggcggcgctc ctggtggtaa ccctacccctt   2700
```

```
tatcaggatc ttgttagggt gtcggccacc ataaccaaca ctggtaacgt cgccggttat    2760
gaagtccctc aattggtgag tgacccgcat gttccttgcg ttgcaatttg gctaactcgc    2820
ttctagtatg tttcactggg cggaccgaac gagcctcggg tcgttctgcg caagttcgac    2880
cgaatcttcc tggctcctgg ggagcaaaag gtttggacca cgactcttaa ccgtcgtgat    2940
ctcgccaatt gggatgtgga ggctcaggac tgggtcatca caaagtaccc caagaaagtg    3000
cacgtcggca gctcctcgcg taagctgcct ctgagagcgc ctctgccccg tgtctactag    3060
```

```
<210> SEQ ID NO 6
<211> LENGTH: 863
<212> TYPE: PRT
<213> ORGANISM: Aspergillus fumigatus

<400> SEQUENCE: 6
```

| | | | | | | | | | | | | | | | |
|---|---|---|---|---|---|---|---|---|---|---|---|---|---|---|---|
| Met | Arg | Phe | Gly | Trp | Leu | Glu | Val | Ala | Ala | Leu | Thr | Ala | Ala | Ser | Val |
| 1 | | | | 5 | | | | | 10 | | | | | 15 | |
| Ala | Asn | Ala | Gln | Glu | Leu | Ala | Phe | Ser | Pro | Pro | Phe | Tyr | Pro | Ser | Pro |
| | | | 20 | | | | | 25 | | | | | 30 | | |
| Trp | Ala | Asp | Gly | Gln | Gly | Glu | Trp | Ala | Asp | Ala | His | Arg | Arg | Ala | Val |
| | | | 35 | | | | | 40 | | | | | 45 | | |
| Glu | Ile | Val | Ser | Gln | Met | Thr | Leu | Ala | Glu | Lys | Val | Asn | Leu | Thr | Thr |
| 50 | | | | | 55 | | | | | 60 | | | | | |
| Gly | Thr | Gly | Trp | Glu | Met | Asp | Arg | Cys | Val | Gly | Gln | Thr | Gly | Ser | Val |
| 65 | | | | | 70 | | | | | 75 | | | | | 80 |
| Pro | Arg | Leu | Gly | Ile | Asn | Trp | Gly | Leu | Cys | Gly | Gln | Asp | Ser | Pro | Leu |
| | | | | 85 | | | | | 90 | | | | | 95 | |
| Gly | Ile | Arg | Phe | Ser | Asp | Leu | Asn | Ser | Ala | Phe | Pro | Ala | Gly | Thr | Asn |
| | | | | 100 | | | | | 105 | | | | | 110 | |
| Val | Ala | Ala | Thr | Trp | Asp | Lys | Thr | Leu | Ala | Tyr | Leu | Arg | Gly | Lys | Ala |
| | | | 115 | | | | | 120 | | | | | 125 | | |
| Met | Gly | Glu | Glu | Phe | Asn | Asp | Lys | Gly | Val | Asp | Ile | Leu | Leu | Gly | Pro |
| | 130 | | | | | 135 | | | | | 140 | | | | |
| Ala | Ala | Gly | Pro | Leu | Gly | Lys | Tyr | Pro | Asp | Gly | Gly | Arg | Ile | Trp | Glu |
| 145 | | | | | 150 | | | | | 155 | | | | | 160 |
| Gly | Phe | Ser | Pro | Asp | Pro | Val | Leu | Thr | Gly | Val | Leu | Phe | Ala | Glu | Thr |
| | | | | 165 | | | | | 170 | | | | | 175 | |
| Ile | Lys | Gly | Ile | Gln | Asp | Ala | Gly | Val | Ile | Ala | Thr | Ala | Lys | His | Tyr |
| | | | | 180 | | | | | 185 | | | | | 190 | |
| Ile | Leu | Asn | Glu | Gln | Glu | His | Phe | Arg | Gln | Val | Gly | Glu | Ala | Gln | Gly |
| | | | 195 | | | | | 200 | | | | | 205 | | |
| Tyr | Gly | Tyr | Asn | Ile | Thr | Glu | Thr | Ile | Ser | Ser | Asn | Val | Asp | Asp | Lys |
| | 210 | | | | | 215 | | | | | 220 | | | | |
| Thr | Met | His | Glu | Leu | Tyr | Leu | Trp | Pro | Phe | Ala | Asp | Ala | Val | Arg | Ala |
| 225 | | | | | 230 | | | | | 235 | | | | | 240 |
| Gly | Val | Gly | Ala | Val | Met | Cys | Ser | Tyr | Asn | Gln | Ile | Asn | Asn | Ser | Tyr |
| | | | | 245 | | | | | 250 | | | | | 255 | |
| Gly | Cys | Gln | Asn | Ser | Gln | Thr | Leu | Asn | Lys | Leu | Leu | Lys | Ala | Glu | Leu |
| | | | | 260 | | | | | 265 | | | | | 270 | |
| Gly | Phe | Gln | Gly | Phe | Val | Met | Ser | Asp | Trp | Ser | Ala | His | His | Ser | Gly |
| | | | 275 | | | | | 280 | | | | | 285 | | |
| Val | Gly | Ala | Ala | Leu | Ala | Gly | Leu | Asp | Met | Ser | Met | Pro | Gly | Asp | Ile |
| | 290 | | | | | 295 | | | | | 300 | | | | |
| Ser | Phe | Asp | Asp | Gly | Leu | Ser | Phe | Trp | Gly | Thr | Asn | Leu | Thr | Val | Ser |
| 305 | | | | | 310 | | | | | 315 | | | | | 320 |

```
Val Leu Asn Gly Thr Val Pro Ala Trp Arg Val Asp Met Ala Val
            325                 330                 335

Arg Ile Met Thr Ala Tyr Tyr Lys Val Gly Arg Asp Arg Leu Arg Ile
            340                 345                 350

Pro Pro Asn Phe Ser Ser Trp Thr Arg Asp Glu Tyr Gly Trp Glu His
            355                 360                 365

Ser Ala Val Ser Glu Gly Ala Trp Thr Lys Val Asn Asp Phe Val Asn
        370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
            405                 410                 415

Val Lys Val Gly Val Leu Gly Glu Asp Ala Gly Ser Asn Pro Trp Gly
            420                 425                 430

Ala Asn Gly Cys Pro Asp Arg Gly Cys Asp Asn Gly Thr Leu Ala Met
        435                 440                 445

Ala Trp Gly Ser Gly Thr Ala Asn Phe Pro Tyr Leu Val Thr Pro Glu
        450                 455                 460

Gln Ala Ile Gln Arg Glu Val Ile Ser Asn Gly Gly Asn Val Phe Ala
465                 470                 475                 480

Val Thr Asp Asn Gly Ala Leu Ser Gln Met Ala Asp Val Ala Ser Gln
            485                 490                 495

Ser Ser Val Ser Leu Val Phe Val Asn Ala Asp Ser Gly Glu Gly Phe
        500                 505                 510

Ile Ser Val Asp Gly Asn Glu Gly Asp Arg Lys Asn Leu Thr Leu Trp
        515                 520                 525

Lys Asn Gly Glu Ala Val Ile Asp Thr Val Val Ser His Cys Asn Asn
530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
            565                 570                 575

Gln Glu Ser Gly Asn Ser Leu Val Asp Val Leu Tyr Gly Arg Val Asn
        580                 585                 590

Pro Ser Ala Lys Thr Pro Phe Thr Trp Gly Lys Thr Arg Glu Ser Tyr
        595                 600                 605

Gly Ala Pro Leu Leu Thr Glu Pro Asn Asn Gly Asn Gly Ala Pro Gln
    610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
            645                 650                 655

Thr Phe Gly Tyr Ser His Leu Arg Val Gln Ala Leu Asn Ser Ser Ser
            660                 665                 670

Ser Ala Tyr Val Pro Thr Ser Gly Glu Thr Lys Pro Ala Pro Thr Tyr
        675                 680                 685

Gly Glu Ile Gly Ser Ala Ala Asp Tyr Leu Tyr Pro Glu Gly Leu Lys
    690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
            725                 730                 735
```

```
Pro Glu Gly Ala Arg Asp Gly Ser Pro Gln Pro Leu Leu Lys Ala Gly
            740                 745                 750

Gly Ala Pro Gly Gly Asn Pro Thr Leu Tyr Gln Asp Leu Val Arg Val
        755                 760                 765

Ser Ala Thr Ile Thr Asn Thr Gly Asn Val Ala Gly Tyr Glu Val Pro
    770                 775                 780

Gln Leu Tyr Val Ser Leu Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
        835                 840                 845

Ser Ser Arg Lys Leu Pro Leu Arg Ala Pro Leu Pro Arg Val Tyr
    850                 855                 860
```

<210> SEQ ID NO 7
<211> LENGTH: 862
<212> TYPE: DNA
<213> ORGANISM: Aspergillus fumigatus

<400> SEQUENCE: 7

```
atgactttgt ccaagatcac ttccattgct ggccttctgg cctcagcgtc tctcgtggct    60
ggccacggct ttgtttctgg cattgttgct gatgggaaat agtatgtgct tgaaccacac   120
aaatgacagc tgcaacagct aacttctatt ccagttacgg agggtacctt gttaaccaat   180
accctacat gagcaaccct cccgacacca ttgcctggtc caccaccgcc accgacctcg   240
gctttgtgga cggcaccggc taccagtctc cggatattat ctgccacaga gacgcaaaga   300
atggcaagtt gaccgcaacc gttgcagccg ttcacagat cgaattccag tggacgacgt   360
ggccagagtc tcaccatgga ccggtacgac gccgaagaga agagaacata ttgtgaccag   420
ataggctaac atagcatagt tgattactta cctcgctcca tgcaacggcg actgtgccac   480
cgtggacaag accaccctga gtttgtcaa gatcgccgct caaggcttga tcgacggctc   540
caacccacct ggtgtttggg ctgatgatga atgatcgcc aacaacaaca cggccacagt   600
gaccattcct gcctcctatg ccccccggaaa ctacgtcctt cgccacgaga tcatcgccct   660
tcactctgcg ggtaacctga acggcgcgca gaactacccc cagtgtttca acatccaaat   720
caccggtggc ggcagtgctc agggatctgg caccgctggc acgtccctgt acaagaatac   780
tgatcctggc atcaagtttg acatctactc ggatctgagc ggtggatacc ctattcctgg   840
tcctgcactg ttcaacgctt aa                                            862
```

<210> SEQ ID NO 8
<211> LENGTH: 250
<212> TYPE: PRT
<213> ORGANISM: Aspergillus fumigatus

<400> SEQUENCE: 8

```
Met Thr Leu Ser Lys Ile Thr Ser Ile Ala Gly Leu Leu Ala Ser Ala
1               5                   10                  15

Ser Leu Val Ala Gly His Gly Phe Val Ser Gly Ile Val Ala Asp Gly
            20                  25                  30

Lys Tyr Tyr Gly Gly Tyr Leu Val Asn Gln Tyr Pro Tyr Met Ser Asn
        35                  40                  45
```

Pro Pro Asp Thr Ile Ala Trp Ser Thr Thr Ala Thr Asp Leu Gly Phe
    50                  55                  60

Val Asp Gly Thr Gly Tyr Gln Ser Pro Asp Ile Ile Cys His Arg Asp
65                  70                  75                  80

Ala Lys Asn Gly Lys Leu Thr Ala Thr Val Ala Ala Gly Ser Gln Ile
                85                  90                  95

Glu Phe Gln Trp Thr Thr Trp Pro Glu Ser His His Gly Pro Leu Ile
            100                 105                 110

Thr Tyr Leu Ala Pro Cys Asn Gly Asp Cys Ala Thr Val Asp Lys Thr
        115                 120                 125

Thr Leu Lys Phe Val Lys Ile Ala Ala Gln Gly Leu Ile Asp Gly Ser
    130                 135                 140

Asn Pro Pro Gly Val Trp Ala Asp Asp Glu Met Ile Ala Asn Asn Asn
145                 150                 155                 160

Thr Ala Thr Val Thr Ile Pro Ala Ser Tyr Ala Pro Gly Asn Tyr Val
                165                 170                 175

Leu Arg His Glu Ile Ile Ala Leu His Ser Ala Gly Asn Leu Asn Gly
            180                 185                 190

Ala Gln Asn Tyr Pro Gln Cys Phe Asn Ile Gln Ile Thr Gly Gly Gly
        195                 200                 205

Ser Ala Gln Gly Ser Gly Thr Ala Gly Thr Ser Leu Tyr Lys Asn Thr
    210                 215                 220

Asp Pro Gly Ile Lys Phe Asp Ile Tyr Ser Asp Leu Ser Gly Gly Tyr
225                 230                 235                 240

Pro Ile Pro Gly Pro Ala Leu Phe Asn Ala
                245                 250

<210> SEQ ID NO 9
<211> LENGTH: 1254
<212> TYPE: DNA
<213> ORGANISM: Aspergillus fumigatus

<400> SEQUENCE: 9
actggattta ccatggctca aacactggca gccgcctcgc tggttctcgt ccccttgtg      60 actgcgcagc agatcgggtc catcgctgag aaccacccgg agctcaaaac atacaggtgc    120
ggttctcagg ctggctgcgt tgcacaaagc acctcagtgg ttcttgacat caacgcacac    180
tggatacacc aaatgggagc ccaaacgtca tgcaccacga gtagtggcct cgacccgtct    240
ctctgccccg acaaggtgac ctgcagccag aactgcgtag tggaaggcat caccgactac    300
agtagcttcg gcgtgcagaa ctcaggcgac gccataaccc tccgccaata ccaagtacaa    360
aacggccaga tcaagacact gaggccgcgc gtgtacctcc tcgccgagga tggcatcaac    420
tacagcaagc tgcagctcct caaccaagag ttcaccttcg acgttgacgc ctccaagctc    480
ccctgcggca tgaacggcgc cctctacctc tccgaaatgg acgcctcagg cggccgcagc    540
gccctcaacc ccgctggtgc aacctacggc acaggctact gcgacgcgca gtgcttcaac    600
cccggtccct ggatcaacgg cgaggccaac accctcggcg caggtgcctg ctgccaggag    660
atggacctct gggaggccaa ctcgcgctcc acaattttct ccccgcaccc gtgcaccaca    720
gccgcctgta cgcgtgcac cggcgccgaa tgctactcca tctgcgacgg gtatggctgc    780
acctacaacc cctacgagct cggcgcaaag gattactatg gctacggtct caccgttgac    840
accgccaagc gtaaccgt cgtcatgcag ttcgtgacgg ccgataacac cgcgacagga    900
actctggccg agatccgcag gctgtacgtg caggagggta tggtgatcgg caattcggcc    960

-continued

```
gtcgccatga cggaggcttt ctgctcgtcg tcgaggacgt tcgaggcgct gggtgggttg    1020
cagcgtatgg gcgaggctct ggggaggggc atggtgcctg tgttcagtat ctgggatgat    1080
ccgagcctgt ggatgcattg gcttgatagt gacggtgccg ggccgtgcgg tagcactgag    1140
ggagatcctg ctttcatcca ggctaactat cccaatacgg cggtgacttt ttcgaaggtc    1200
aggtgggggg atattgacag tacctactct gtttagttaa ttaactagag gtga          1254
```

<210> SEQ ID NO 10
<211> LENGTH: 407
<212> TYPE: PRT
<213> ORGANISM: Aspergillus fumigatus

<400> SEQUENCE: 10

```
Met Ala Gln Thr Leu Ala Ala Ser Leu Val Leu Val Pro Leu Val
1               5                   10                  15

Thr Ala Gln Gln Ile Gly Ser Ile Ala Glu Asn His Pro Glu Leu Lys
            20                  25                  30

Thr Tyr Arg Cys Gly Ser Gln Ala Gly Cys Val Ala Gln Ser Thr Ser
        35                  40                  45

Val Val Leu Asp Ile Asn Ala His Trp Ile His Gln Met Gly Ala Gln
50                  55                  60

Thr Ser Cys Thr Thr Ser Ser Gly Leu Asp Pro Ser Leu Cys Pro Asp
65                  70                  75                  80

Lys Val Thr Cys Ser Gln Asn Cys Val Val Glu Gly Ile Thr Asp Tyr
                85                  90                  95

Ser Ser Phe Gly Val Gln Asn Ser Gly Asp Ala Ile Thr Leu Arg Gln
            100                 105                 110

Tyr Gln Val Gln Asn Gly Gln Ile Lys Thr Leu Arg Pro Arg Val Tyr
        115                 120                 125

Leu Leu Ala Glu Asp Gly Ile Asn Tyr Ser Lys Leu Gln Leu Leu Asn
130                 135                 140

Gln Glu Phe Thr Phe Asp Val Asp Ala Ser Lys Leu Pro Cys Gly Met
145                 150                 155                 160

Asn Gly Ala Leu Tyr Leu Ser Glu Met Asp Ala Ser Gly Gly Arg Ser
                165                 170                 175

Ala Leu Asn Pro Ala Gly Ala Thr Tyr Gly Thr Gly Tyr Cys Asp Ala
            180                 185                 190

Gln Cys Phe Asn Pro Gly Pro Trp Ile Asn Gly Glu Ala Asn Thr Leu
        195                 200                 205

Gly Ala Gly Ala Cys Cys Gln Glu Met Asp Leu Trp Glu Ala Asn Ser
210                 215                 220

Arg Ser Thr Ile Phe Ser Pro His Pro Cys Thr Thr Ala Gly Leu Tyr
225                 230                 235                 240

Ala Cys Thr Gly Ala Glu Cys Tyr Ser Ile Cys Asp Gly Tyr Gly Cys
                245                 250                 255

Thr Tyr Asn Pro Tyr Glu Leu Gly Ala Lys Asp Tyr Tyr Gly Tyr Gly
            260                 265                 270

Leu Thr Val Asp Thr Ala Lys Pro Ile Thr Val Val Met Gln Phe Val
        275                 280                 285

Thr Ala Asp Asn Thr Ala Thr Gly Thr Leu Ala Glu Ile Arg Arg Leu
290                 295                 300

Tyr Val Gln Glu Gly Met Val Ile Gly Asn Ser Ala Val Ala Met Thr
305                 310                 315                 320

Glu Ala Phe Cys Ser Ser Ser Arg Thr Phe Glu Ala Leu Gly Gly Leu
```

```
                        325                 330                 335
Gln Arg Met Gly Glu Ala Leu Gly Arg Gly Met Val Pro Val Phe Ser
            340                 345                 350

Ile Trp Asp Asp Pro Ser Leu Trp Met His Trp Leu Asp Ser Asp Gly
        355                 360                 365

Ala Gly Pro Cys Gly Ser Thr Glu Gly Asp Pro Ala Phe Ile Gln Ala
    370                 375                 380

Asn Tyr Pro Asn Thr Ala Val Thr Phe Ser Lys Val Arg Trp Gly Asp
385                 390                 395                 400

Ile Asp Ser Thr Tyr Ser Val
                405

<210> SEQ ID NO 11
<211> LENGTH: 1263
<212> TYPE: DNA
<213> ORGANISM: Aspergillus fumigatus

<400> SEQUENCE: 11
actggattta ccatgaaatt cggtagcatt gtgctcattg ctgctgcggc aggcttcgcg      60
gtggctgctc ctgcaaagag agcttcggta tttcaatgtt ggttccctgt ggtaaagttg     120
gattaaaagg acactaacat actgcagggt tcggaagcaa tgagtctgga gcagagtttg     180
gcgaaaatac cattcctggc tcttatgtat gttgtgcatc tgagagaagt atactgctgc     240
tgacaacatc aaggggaaag aattcatctt cccggaccct tctacaatca gcacattgat     300
cgggaagggc atgaacatct tccggattca attcctcatg gagagactgg tgccaagctc     360
tatgacaggc tcctataacg aggagtacct tgccaatctg acatcggtgg gtttgagcag     420
cagcatgttg gactgtatga ggctgactcg accaggttgt ggacgctgtc accaaggcag     480
gatcttatgc tattttggac ccacacaact ttggcagata gtgagtaatg cccggcatac     540
tgtggacttg ttctaacgcc actcagcaat ggtcagatta tctccagcac cgacgacttc     600
aagaccttct ggcagaatct ggctggaaag ttcaagtcca caatctcgt catctttgat      660 actagtatgg ctaactcatt tggttctgat gagcttcact gaccccggat gttagacaat      720
gagtatcacg acatggacca gacactggta ctgaacctca accaggccgc tatcaacggt     780
atccgcgctg caggagccac ctcgcaatac atctttgtgg agggcaactc ctggaccggc     840
gcctggacct gggccgacgt caatgacaac ctgaaggctc tgaccgaccc ccaggataag     900
atcgtctacg agatgcacca gtatctcgac tcggatggat ccggcaccgc ggagagctgc     960
gtgtctacca cgattggtaa ggagcgggtt tcggccgcaa caaagtggct caaggataac    1020
ggcaaggttg gcatcattgg tgagttcgct ggtggcgtca atgatcagtg ccggaccgct    1080
atttcaggaa tgctggagta cttggctcag aacacagacg tgtggaaggg agctctctgg    1140
tgggcggctg gccccggtg gggaaactat atgttcaaca tggagcctcc gagcggtgca    1200
gcttatgtgg gcatgttgga catcttggag ccctacctgg ttgattaat taactagagg    1260 tga                                                                 1263

<210> SEQ ID NO 12
<211> LENGTH: 329
<212> TYPE: PRT
<213> ORGANISM: Aspergillus fumigatus

<400> SEQUENCE: 12

Met Lys Phe Gly Ser Ile Val Leu Ile Ala Ala Ala Gly Phe Ala
1               5                   10                  15
```

Val Ala Ala Pro Ala Lys Arg Ala Ser Val Phe Gln Trp Phe Gly Ser
            20                  25                  30

Asn Glu Ser Gly Ala Glu Phe Gly Glu Asn Thr Ile Pro Gly Ser Tyr
        35                  40                  45

Gly Lys Glu Phe Ile Phe Pro Asp Pro Ser Thr Ile Ser Thr Leu Ile
 50                  55                  60

Gly Lys Gly Met Asn Ile Phe Arg Ile Gln Phe Leu Met Glu Arg Leu
 65                  70                  75                  80

Val Pro Ser Ser Met Thr Gly Ser Tyr Asn Glu Glu Tyr Leu Ala Asn
                85                  90                  95

Leu Thr Ser Val Val Asp Ala Val Thr Lys Ala Gly Ser Tyr Ala Ile
            100                 105                 110

Leu Asp Pro His Asn Phe Gly Arg Tyr Asn Gly Gln Ile Ile Ser Ser
        115                 120                 125

Thr Asp Asp Phe Lys Thr Phe Trp Gln Asn Leu Ala Gly Lys Phe Lys
130                 135                 140

Ser Asn Asn Leu Val Ile Phe Asp Thr Asn Asn Glu Tyr His Asp Met
145                 150                 155                 160

Asp Gln Thr Leu Val Leu Asn Leu Asn Gln Ala Ile Asn Gly Ile
                165                 170                 175

Arg Ala Ala Gly Ala Thr Ser Gln Tyr Ile Phe Val Glu Gly Asn Ser
            180                 185                 190

Trp Thr Gly Ala Trp Thr Trp Ala Asp Val Asn Asp Asn Leu Lys Ala
        195                 200                 205

Leu Thr Asp Pro Gln Asp Lys Ile Val Tyr Glu Met His Gln Tyr Leu
210                 215                 220

Asp Ser Asp Gly Ser Gly Thr Ala Glu Ser Cys Val Ser Thr Thr Ile
225                 230                 235                 240

Gly Lys Glu Arg Val Ser Ala Ala Thr Lys Trp Leu Lys Asp Asn Gly
                245                 250                 255

Lys Val Gly Ile Ile Gly Glu Phe Ala Gly Gly Val Asn Asp Gln Cys
            260                 265                 270

Arg Thr Ala Ile Ser Gly Met Leu Glu Tyr Leu Ala Gln Asn Thr Asp
        275                 280                 285

Val Trp Lys Gly Ala Leu Trp Trp Ala Ala Gly Pro Trp Trp Gly Asn
290                 295                 300

Tyr Met Phe Asn Met Glu Pro Pro Ser Gly Ala Ala Tyr Val Gly Met
305                 310                 315                 320

Leu Asp Ile Leu Glu Pro Tyr Leu Gly
                325

<210> SEQ ID NO 13
<211> LENGTH: 1145
<212> TYPE: DNA
<213> ORGANISM: Aspergillus fumigatus

<400> SEQUENCE: 13
atgcgtttct cccttgccgc caccgctctt ctcgctggcc tggccacggc agcgccttcg    60
agcaacaaga caacgtcaa tcttgataag cttgctcggc gtaatggcat gctttggttc   120
ggcactgcag ccgatatccc tggtacctca gaaacaaccg acaagcctta tctgagcatc   180
ctgcgcaagc agttcggcga atgacaccc gcaaacgcat tgaaggtgag ccagagtgat   240
agtacacctc atctcgtgtc ggcgctgacc agacgatgtt attcacatag ttcatgtata   300

```
ccgagcccga gcagaatgtc ttcaacttca ctcaagggga ctacttcatg gacttggccg      360
atcactatgg tcacgccgtg cgctgccata acctcgtctg gccagccaa gtgtccgact       420 gggtcacctc caggaactgg accgccacag aactcaaaga agtgatgaag aaccacatat      480
tcaagaccgt ccacattttt ggcaagcgct gctacgcgtg ggacgtcgtc aatgaagcta      540
ttaatgggga cggaccttt tcctccagtg tgtggtacga cacaattggc gaggaatact       600
tctaccttgc attccagtat gcccaggaag ccctggcgca gattcacgcc aaccaggtca      660
agctttacta taacgactat ggcattgaga accccggccc caaggcagat gctgttctga      720
agctagtcgc cgagttgcgg aagcggggca ttcgcattga cggagtcggt ctcgagtccc      780
acttcatcgt cggcgagact ccttcgctgg ctgaccagct cgccaccaag aaggcttata      840
tcgaggccgg acttgaggtc gccatcaccg aacttgacgt ccgctttctct caggccccgt     900 tctacaccgc cgaggcccaa aagcagcagg ctgccgacta ctatgctagc gtcgccagtt     960
gcaagcatgc cggaccgcgc tgtgttggtg ttgtagtctg ggatttcgat gacgcctact     1020
cgtggattcc gggtaccttc gagggacagg gtggcgcctg tctatataat gagacactcg    1080
aggtgaagcc ggccttctat gctgctgccg aggcgttgga gaacaagccc tgcactgtat    1140
gctag                                                                 1145
```

<210> SEQ ID NO 14
<211> LENGTH: 364
<212> TYPE: PRT
<213> ORGANISM: Aspergillus fumigatus

<400> SEQUENCE: 14

Met Arg Phe Ser Leu Ala Ala Thr Ala Leu Leu Ala Gly Leu Ala Thr
1               5                   10                  15

Ala Ala Pro Ser Ser Asn Lys Asn Asn Val Asn Leu Asp Lys Leu Ala
            20                  25                  30

Arg Arg Asn Gly Met Leu Trp Phe Gly Thr Ala Ala Asp Ile Pro Gly
        35                  40                  45

Thr Ser Glu Thr Thr Asp Lys Pro Tyr Leu Ser Ile Leu Arg Lys Gln
    50                  55                  60

Phe Gly Glu Met Thr Pro Ala Asn Ala Leu Lys Val Ser Gln Ser Asp
65                  70                  75                  80

Phe Met Tyr Thr Glu Pro Glu Gln Asn Val Phe Asn Phe Thr Gln Gly
                85                  90                  95

Asp Tyr Phe Met Asp Leu Ala Asp His Tyr Gly His Ala Val Arg Cys
            100                 105                 110

His Asn Leu Val Trp Ala Ser Gln Val Ser Asp Trp Val Thr Ser Arg
        115                 120                 125

Asn Trp Thr Ala Thr Glu Leu Lys Glu Val Met Lys Asn His Ile Phe
    130                 135                 140

Lys Thr Val Gln His Phe Gly Lys Arg Cys Tyr Ala Trp Asp Val Val
145                 150                 155                 160

Asn Glu Ala Ile Asn Gly Asp Gly Thr Phe Ser Ser Ser Val Trp Tyr
                165                 170                 175

Asp Thr Ile Gly Glu Glu Tyr Phe Tyr Leu Ala Phe Gln Tyr Ala Gln
            180                 185                 190

Glu Ala Leu Ala Gln Ile His Ala Asn Gln Val Lys Leu Tyr Tyr Asn
        195                 200                 205

Asp Tyr Gly Ile Glu Asn Pro Gly Pro Lys Ala Asp Ala Val Leu Lys
    210                 215                 220

```
Leu Val Ala Glu Leu Arg Lys Arg Gly Ile Arg Ile Asp Gly Val Gly
225                 230                 235                 240

Leu Glu Ser His Phe Ile Val Gly Glu Thr Pro Ser Leu Ala Asp Gln
            245                 250                 255

Leu Ala Thr Lys Lys Ala Tyr Ile Glu Ala Gly Leu Glu Val Ala Ile
        260                 265                 270

Thr Glu Leu Asp Val Arg Phe Ser Gln Ala Pro Phe Tyr Thr Ala Glu
    275                 280                 285

Ala Gln Lys Gln Gln Ala Ala Asp Tyr Tyr Ala Ser Val Ala Ser Cys
290                 295                 300

Lys His Ala Gly Pro Arg Cys Val Gly Val Val Trp Asp Phe Asp
305                 310                 315                 320

Asp Ala Tyr Ser Trp Ile Pro Gly Thr Phe Glu Gly Gln Gly Gly Ala
                325                 330                 335

Cys Leu Tyr Asn Glu Thr Leu Glu Val Lys Pro Ala Phe Tyr Ala Ala
            340                 345                 350

Ala Glu Ala Leu Glu Asn Lys Pro Cys Thr Val Cys
        355                 360

<210> SEQ ID NO 15
<211> LENGTH: 1400
<212> TYPE: DNA
<213> ORGANISM: Aspergillus fumigatus

<400> SEQUENCE: 15
atggtcgtcc tcagcaagct cgtcagcagc attctctttg tctccctggt ttcggcgggc      60
gtgatcgacg aacgccaggc agccggcatc aaccaggcgt ttacctccca tggcaagaag     120
tactttggca ccgccagtga ccaagctctg ctccagaagt cgcagaatga ggccattgtg     180
cgcaaagact ttggccagct gacgccggag aatagcatga agtgggatgc gactgagcgt     240
aggtctctcg ccactgtggg ctgacgttaa cttgttgaca tgactgtctg tgtagcatcg     300
caaggaagat tcaacttcgc tggtgctgat tcctggtat gcaatctgct catctcggtc     360
gagctcctgc tgaaggacaa taaataggtc aactatgcaa aacagaatgg caagaaggtc     420
cgcggacaca ccttaggtat tcatgcgccc tcacggcatt tcgaggatac agccaagctg     480
acagtgtagt ctggcactcc caactcccgt cctgggtgtc ggctatcagc gacaaaaaca     540
ccctgacctc ggtgctgaag aaccacatca ccaccgtcat gacccggtac aagggccaga     600
tctacgcctg gtattttgc cctctatccc acacaatgcc agcccagct aatagctgca     660 aaggacgtcg tcaacgagat cttcaacgag gacggctccc tccgcgacag cgtcttctcc     720
cgcgtgctgg cgaggacttt gtgcggatt gccttcgaga cggcgcgctc tgtggatccc     780
tcggcgaagc tgtacatcaa cgattacaag taagcttgtg gttttgtcga gagatgtact     840
ccgtcctgga tctgaccatc acagtctcga ctcggctagc tatggcaaaa cccaggggat     900
ggtgagatat gtcaagaagt ggctggctgc gggcattcct atcgatggaa tcggtgagca     960
caggtcgcgg agctgtgtgt gatgattgta cgctgactct tcctgaaggc actcaaaccc    1020
accttggtgc gggtgcttcg tccagcgtca aggataagt ctccttggtt ttcttgccta    1080
cgtaacgctg accccccgtg tacagcattg actgctcttg cgtcttccgg cgtctctgag    1140
gtcgccatta ccgagctgga tatcgcgggt gcgagctccc aggactacgt caatgtatgt    1200
ctcctgattg ccagtggcag ggtcatcgat actaatagaa acaggtcgtc aaggcatgcc    1260
tggatgtccc caagtgtgtg ggaatcaccg tctgggggt gtcggacagg gactcgtggc    1320
```
gctccggctc gtctccgctg ctgttcgaca gcaactacca gcccaaggcg gcgtataatg    1380
ccatcattgc tgctctctga                                                1400

<210> SEQ ID NO 16
<211> LENGTH: 323
<212> TYPE: PRT
<213> ORGANISM: Aspergillus fumigatus

<400> SEQUENCE: 16

Met Val Val Leu Ser Lys Leu Val Ser Ser Ile Leu Phe Val Ser Leu
1               5                   10                  15

Val Ser Ala Gly Val Ile Asp Glu Arg Gln Ala Ala Gly Ile Asn Gln
            20                  25                  30

Ala Phe Thr Ser His Gly Lys Lys Tyr Phe Gly Thr Ala Ser Asp Gln
        35                  40                  45

Ala Leu Leu Gln Lys Ser Gln Asn Glu Ala Ile Val Arg Lys Asp Phe
    50                  55                  60

Gly Gln Leu Thr Pro Glu Asn Ser Met Lys Trp Asp Ala Thr Glu Ala
65                  70                  75                  80

Ser Gln Gly Arg Phe Asn Phe Ala Gly Ala Asp Phe Leu Val Asn Tyr
                85                  90                  95

Ala Lys Gln Asn Gly Lys Lys Val Arg Gly His Thr Leu Trp His Ser
            100                 105                 110

Gln Leu Pro Ser Trp Val Ser Ala Ile Ser Asp Lys Asn Thr Leu Thr
        115                 120                 125

Ser Val Leu Lys Asn His Ile Thr Thr Val Met Thr Arg Tyr Lys Gly
    130                 135                 140

Gln Ile Tyr Ala Trp Asp Val Val Asn Glu Ile Phe Asn Glu Asp Gly
145                 150                 155                 160

Ser Leu Arg Asp Ser Val Phe Ser Arg Val Leu Gly Glu Asp Phe Val
                165                 170                 175

Arg Ile Ala Phe Glu Thr Ala Arg Ser Val Asp Pro Ser Ala Lys Leu
            180                 185                 190

Tyr Ile Asn Asp Tyr Lys Leu Asp Ser Ala Ser Tyr Gly Lys Thr Gln
        195                 200                 205

Gly Met Val Arg Tyr Val Lys Lys Trp Leu Ala Gly Ile Pro Ile
    210                 215                 220

Asp Gly Ile Gly Gln Thr His Leu Gly Ala Gly Ala Ser Ser Ser Val
225                 230                 235                 240

Lys Gly Ala Leu Thr Ala Leu Ala Ser Ser Gly Val Ser Glu Val Ala
                245                 250                 255

Ile Thr Glu Leu Asp Ile Ala Gly Ala Ser Ser Gln Asp Tyr Val Asn
            260                 265                 270

Val Val Lys Ala Cys Leu Asp Val Pro Lys Cys Val Gly Ile Thr Val
        275                 280                 285

Trp Gly Val Ser Asp Arg Asp Ser Trp Arg Ser Gly Ser Ser Pro Leu
    290                 295                 300

Leu Phe Asp Ser Asn Tyr Gln Pro Lys Ala Ala Tyr Asn Ala Ile Ile
305                 310                 315                 320

Ala Ala Leu

<210> SEQ ID NO 17
<211> LENGTH: 1415
<212> TYPE: DNA

<213> ORGANISM: Aspergillus fumigatus

<400> SEQUENCE: 17

```
atggtccatc tatcttcatt ggcagcagcc ctggctgctc tgcctctgta tgtttaccca    60
ctcacgagag gaggaacagc tttgacattg ctatagtgta tatggagctg gcctgaacac   120
agcagccaaa gccaaaggac taaagtactt tggttccgcc acggacaatc cagagctcac   180
ggactctgcg tatgtcgcgc aactgagcaa caccgatgat tttggtcaaa tcacacccgg   240
aaactccatg aaggtttgct tacgtctgcc tccctggagc attgcctcaa aagctaattg   300
gttgttttgt ttggatagtg ggatgccacc gagccttctc agaattcttt ttcgttcgca   360
aatggagacg ccgtggtcaa tctggcgaac aagaatggcc agctgatgcg atgccatact   420
ctggtctggc acagtcagct accgaactgg ggtatgtaaa cgtcttgtct attctcaaat   480
actctctaac agttgacagt ctctagcggg tcatggacca atgcgaccct tttggcggcc   540
atgaagaatc atatcaccaa tgtggttact cactacaagg ggaagtgcta cgcctgggat   600
gttgtcaatg aaggtttgtt gctccatcta tcctcaatag ttcttttgaa actgacaagc   660
ctgtcaatct agccctgaac gaggacggta ctttccgtaa ctctgtcttc taccagatca   720
tcggcccagc atacattcct attgcgttcg ccacggctgc tgccgcagat cccgacgtga   780
aactctacta caacgactac aacattgaat actcaggcgc aaagcgact gctgcgcaga   840
atatcgtcaa gatgatcaag gcctacgcgc gaagatcga cggcgtcggc ctccaggcac   900
actttatcgt cggcagcact ccgagtcaat cggatctgac gaccgtcttg aagggctaca   960
ctgctctcgg cgttgaggtg gcctataccg aacttgacat ccgcatgcag ctgccctcga  1020
ccgccgcaaa gctggcccag cagtccactg acttccaagg cgtggccgca gcatgcgtta  1080
gcaccactgg ctgcgtgggt gtcactatct gggactggac cgacaagtac tcctgggtcc  1140
ccagcgtgtt ccaaggctac ggcgccccat gccttggga tgagaactat gtgaagaagc  1200
cagcgtacga tggcctgatg gcgggtcttg gagcaagcgg ctccggcacc acaacgacca  1260
ctactactac ttctactacg acaggaggta cggaccctac tggagtcgct cagaaatggg  1320
gacagtgtgg cggtattggc tggaccgggc caacaacttg tgtcagtggt accacttgcc  1380
aaaagctgaa tgactggtac tcacagtgcc tgtaa                             1415
```

<210> SEQ ID NO 18
<211> LENGTH: 397
<212> TYPE: PRT
<213> ORGANISM: Aspergillus fumigatus

<400> SEQUENCE: 18

```
Met Val His Leu Ser Ser Leu Ala Ala Ala Leu Ala Ala Leu Pro Leu
1               5                   10                  15

Val Tyr Gly Ala Gly Leu Asn Thr Ala Ala Lys Ala Lys Gly Leu Lys
            20                  25                  30

Tyr Phe Gly Ser Ala Thr Asp Asn Pro Glu Leu Thr Asp Ser Ala Tyr
        35                  40                  45

Val Ala Gln Leu Ser Asn Thr Asp Asp Phe Gly Gln Ile Thr Pro Gly
    50                  55                  60

Asn Ser Met Lys Trp Asp Ala Thr Glu Pro Gln Asn Ser Phe Ser
65                  70                  75                  80

Phe Ala Asn Gly Asp Ala Val Val Asn Leu Ala Asn Lys Asn Gly Gln
                85                  90                  95

Leu Met Arg Cys His Thr Leu Val Trp His Ser Gln Leu Pro Asn Trp
```

```
                100                 105                 110
Val Ser Ser Gly Ser Trp Thr Asn Ala Thr Leu Leu Ala Ala Met Lys
            115                 120                 125

Asn His Ile Thr Asn Val Val Thr His Tyr Lys Gly Lys Cys Tyr Ala
        130                 135                 140

Trp Asp Val Val Asn Glu Ala Leu Asn Glu Asp Gly Thr Phe Arg Asn
145                 150                 155                 160

Ser Val Phe Tyr Gln Ile Ile Gly Pro Ala Tyr Ile Pro Ile Ala Phe
                165                 170                 175

Ala Thr Ala Ala Ala Asp Pro Asp Val Lys Leu Tyr Tyr Asn Asp
            180                 185                 190

Tyr Asn Ile Glu Tyr Ser Gly Ala Lys Ala Thr Ala Ala Gln Asn Ile
        195                 200                 205

Val Lys Met Ile Lys Ala Tyr Gly Ala Lys Ile Asp Gly Val Gly Leu
    210                 215                 220

Gln Ala His Phe Ile Val Gly Ser Thr Pro Ser Gln Ser Asp Leu Thr
225                 230                 235                 240

Thr Val Leu Lys Gly Tyr Thr Ala Leu Gly Val Glu Val Ala Tyr Thr
                245                 250                 255

Glu Leu Asp Ile Arg Met Gln Leu Pro Ser Thr Ala Ala Lys Leu Ala
            260                 265                 270

Gln Gln Ser Thr Asp Phe Gln Gly Val Ala Ala Cys Val Ser Thr
        275                 280                 285

Thr Gly Cys Val Gly Val Thr Ile Trp Asp Trp Thr Asp Lys Tyr Ser
    290                 295                 300

Trp Val Pro Ser Val Phe Gln Gly Tyr Gly Ala Pro Leu Pro Trp Asp
305                 310                 315                 320

Glu Asn Tyr Val Lys Lys Pro Ala Tyr Asp Gly Leu Met Ala Gly Leu
                325                 330                 335

Gly Ala Ser Gly Ser Gly Thr Thr Thr Thr Thr Thr Thr Thr Ser Thr
            340                 345                 350

Thr Thr Gly Gly Thr Asp Pro Thr Gly Val Ala Gln Lys Trp Gly Gln
        355                 360                 365

Cys Gly Gly Ile Gly Trp Thr Gly Pro Thr Thr Cys Val Ser Gly Thr
    370                 375                 380

Thr Cys Gln Lys Leu Asn Asp Trp Tyr Ser Gln Cys Leu
385                 390                 395

<210> SEQ ID NO 19
<211> LENGTH: 2376
<212> TYPE: DNA
<213> ORGANISM: Aspergillus fumigatus

<400> SEQUENCE: 19
atggcggttg ccaaatctat tgctgccgtg ctggtagcac tgttgcctgg tgcgcttgct      60
caggcgaata caagctatgt tgattacaat gtggaggcga atccggatct caccccctcag   120 tcggtcgcta cgattgacct gtcctttccc gactgcgaga tggaccgct cagcaagact     180 ctcgtttgcg acacgtcggc tcggccgcat gaccgagctg ctgccctggt tccatgttc     240 accttcgagg agctggtgaa caacacaggc aacactagcc ctggtgttcc aagacttggt    300
ctccctccgt accaagtatg gagcgaggct ctccatggac ttgaccgcgc caacttcaca    360
aacgagggag agtacagctg gccaccctcg ttccccatgc ctatcctgac aatgtcggcc    420
ttgaaccgaa ccctgatcaa ccagatcgcg accatcatcg caactcaagg acgagctttc    480
```

```
aataacgttg ggcggtatgg gctggacgtg tacgccccga atataaatgc attcagatcg      540
gctatgtggg gaagaggtca agagaccccc ggagaagacg cttactgcct ggcatcggcg      600
tatgcgtacg agtatatcac tggcatccag ggtggtgttg atccggaaca cctcaagttg      660
gtggccactg ccaaacacta tgcgggctac gatcttgaga actgggacgg tcactcccgt      720
ttgggcaacg atatgaacat tacacagcag gaactttccg aatactacac ccctcagttc      780
cttgttgcag ccagagacgc caaagtgcac agtgtcatgt gctcctacaa cgcggtaaat      840
ggggtgccca gctgcgcaaa ctcgttcttc ctccagaccc tcctccgtga cacattcggc      900
ttcgtcgagg atggttatgt atccagcgac tgcgactcgg cgtacaatgt ctggaacccg      960
cacgagtttg cggccaacat cacgggggcc gctgcagact ctatccgggc ggggacggac     1020
attgattgcg gcactactta tcaatactat ttcggcgaag cctttgacga gcaagaggtc     1080
acccgtgcag aaatcgaaag aggtgtgatc cgcctgtaca gcaacttggt gcgtctcggc     1140
tatttcgatg gcaatggaag cgtgtatcgg gacctgacgt ggaatgatgt cgtgaccacg     1200
gatgcctgga atatctcata cgaagccgct gtagaaggca ttgtcctact gaagaacgat     1260
ggaaccttgc ctctcgccaa gtcggtccgc agtgttgcat tgattgggcc ctggatgaat     1320
gtgacgactc agcttcaggg caactacttt ggaccggcgc cttatctgat tagtccgttg     1380
aatgccttcc agaattctga cttcgacgtg aactacgctt tcggcacgaa catttcatcc     1440
cactccacag atgggttttc cgaggcgttg tctgctgcga gaaatccga cgtcatcata     1500
ttcgcgggcg ggattgacaa cacttttgga gcagaagcca tggatcgcat gaatatcaca     1560
tggcccggca atcagctaca gctcatcgac cagttgagcc aactcggcaa accgctgatc     1620
gtcctccaga tgggcggcgg ccaagtcgac tcctcctcgc tcaagtccaa caagaatgtc     1680
aactccctga tctggggtgg ataccccgga caatccggcg ggcaggctct cctagacatc     1740
atcaccggca agcgcgcccc cgccggccga ctcgtggtca cgcagtaccc ggccgaatac     1800
gcaacccagt tccccgccac cgacatgagc ctgcggcctc acggcaataa tcccggccag     1860
acctacatgt ggtacaccgg caccccccgtc tacgagtttg ccacgggct cttctacacg     1920
accttccacg cctccctccc tggcaccggc aaggacaaga cctccttcaa catccaagac     1980
ctcctcacgc agccgcatcc gggcttcgca acgtcgagc aaatgccttt gctcaacttc     2040
accgtgacga tcaccaatac cggcaaggtc gcttccgact acactgctat gctcttcgcg     2100
aacaccaccg cgggacctgc tccatacccg aacaagtggc tcgtcggctt cgaccggctg     2160
gcgagcctgg aaccgcacag gtcgcagact atgaccatcc ccgtgactat cgacagcgtg     2220
gctcgtacgg atgaggccgg caatcggggtt ctctacccgg gaaagtacga gttggccctg     2280
aacaatgagc ggtcggttgt ccttcagttt gtgctgacag gccgagaggc tgtgattttc     2340
aagtggcctg tagagcagca gcagatttcg tctgcg                                2376
```

<210> SEQ ID NO 20
<211> LENGTH: 792
<212> TYPE: PRT
<213> ORGANISM: Aspergillus fumigatus

<400> SEQUENCE: 20

Met Ala Val Ala Lys Ser Ile Ala Ala Val Leu Val Ala Leu Leu Pro
1               5                   10                  15

Gly Ala Leu Ala Gln Ala Asn Thr Ser Tyr Val Asp Tyr Asn Val Glu
            20                  25                  30

Ala Asn Pro Asp Leu Thr Pro Gln Ser Val Ala Thr Ile Asp Leu Ser
             35                  40                  45

Phe Pro Asp Cys Glu Asn Gly Pro Leu Ser Lys Thr Leu Val Cys Asp
 50                  55                  60

Thr Ser Ala Arg Pro His Asp Arg Ala Ala Leu Val Ser Met Phe
 65                  70                  75                  80

Thr Phe Glu Glu Leu Val Asn Asn Thr Gly Asn Thr Ser Pro Gly Val
                 85                  90                  95

Pro Arg Leu Gly Leu Pro Pro Tyr Gln Val Trp Ser Glu Ala Leu His
             100                 105                 110

Gly Leu Asp Arg Ala Asn Phe Thr Asn Glu Gly Glu Tyr Ser Trp Ala
             115                 120                 125

Thr Ser Phe Pro Met Pro Ile Leu Thr Met Ser Ala Leu Asn Arg Thr
             130                 135                 140

Leu Ile Asn Gln Ile Ala Thr Ile Ile Ala Thr Gln Gly Arg Ala Phe
145                 150                 155                 160

Asn Asn Val Gly Arg Tyr Gly Leu Asp Val Tyr Ala Pro Asn Ile Asn
                 165                 170                 175

Ala Phe Arg Ser Ala Met Trp Gly Arg Gly Gln Glu Thr Pro Gly Glu
             180                 185                 190

Asp Ala Tyr Cys Leu Ala Ser Ala Tyr Ala Tyr Glu Tyr Ile Thr Gly
             195                 200                 205

Ile Gln Gly Gly Val Asp Pro Glu His Leu Lys Leu Val Ala Thr Ala
             210                 215                 220

Lys His Tyr Ala Gly Tyr Asp Leu Glu Asn Trp Asp Gly His Ser Arg
225                 230                 235                 240

Leu Gly Asn Asp Met Asn Ile Thr Gln Gln Glu Leu Ser Glu Tyr Tyr
                 245                 250                 255

Thr Pro Gln Phe Leu Val Ala Ala Arg Asp Ala Lys Val His Ser Val
             260                 265                 270

Met Cys Ser Tyr Asn Ala Val Asn Gly Val Pro Ser Cys Ala Asn Ser
             275                 280                 285

Phe Phe Leu Gln Thr Leu Leu Arg Asp Thr Phe Gly Phe Val Glu Asp
             290                 295                 300

Gly Tyr Val Ser Ser Asp Cys Asp Ser Ala Tyr Asn Val Trp Asn Pro
305                 310                 315                 320

His Glu Phe Ala Ala Asn Ile Thr Gly Ala Ala Asp Ser Ile Arg
                 325                 330                 335

Ala Gly Thr Asp Ile Asp Cys Gly Thr Thr Tyr Gln Tyr Tyr Phe Gly
             340                 345                 350

Glu Ala Phe Asp Glu Gln Glu Val Thr Arg Ala Glu Ile Glu Arg Gly
             355                 360                 365

Val Ile Arg Leu Tyr Ser Asn Leu Val Arg Leu Gly Tyr Phe Asp Gly
             370                 375                 380

Asn Gly Ser Val Tyr Arg Asp Leu Thr Trp Asn Asp Val Thr Thr
385                 390                 395                 400

Asp Ala Trp Asn Ile Ser Tyr Glu Ala Val Glu Gly Ile Val Leu
                 405                 410                 415

Leu Lys Asn Asp Gly Thr Leu Pro Leu Ala Lys Ser Val Arg Ser Val
             420                 425                 430

Ala Leu Ile Gly Pro Trp Met Asn Val Thr Thr Gln Leu Gln Gly Asn
             435                 440                 445

Tyr Phe Gly Pro Ala Pro Tyr Leu Ile Ser Pro Leu Asn Ala Phe Gln

```
                    450                 455                 460
Asn Ser Asp Phe Asp Val Asn Tyr Ala Phe Gly Thr Asn Ile Ser Ser
465                 470                 475                 480

His Ser Thr Asp Gly Phe Ser Glu Ala Leu Ser Ala Lys Lys Ser
                485                 490                 495

Asp Val Ile Ile Phe Ala Gly Gly Ile Asp Asn Thr Leu Glu Ala Glu
                500                 505                 510

Ala Met Asp Arg Met Asn Ile Thr Trp Pro Gly Asn Gln Leu Gln Leu
                515                 520                 525

Ile Asp Gln Leu Ser Gln Leu Gly Lys Pro Leu Ile Val Leu Gln Met
                530                 535                 540

Gly Gly Gly Gln Val Asp Ser Ser Ser Leu Lys Ser Asn Lys Asn Val
545                 550                 555                 560

Asn Ser Leu Ile Trp Gly Gly Tyr Pro Gly Gln Ser Gly Gly Gln Ala
                565                 570                 575

Leu Leu Asp Ile Ile Thr Gly Lys Arg Ala Pro Ala Gly Arg Leu Val
                580                 585                 590

Val Thr Gln Tyr Pro Ala Glu Tyr Ala Thr Gln Phe Pro Ala Thr Asp
                595                 600                 605

Met Ser Leu Arg Pro His Gly Asn Asn Pro Gly Gln Thr Tyr Met Trp
                610                 615                 620

Tyr Thr Gly Thr Pro Val Tyr Glu Phe Gly His Gly Leu Phe Tyr Thr
625                 630                 635                 640

Thr Phe His Ala Ser Leu Pro Gly Thr Gly Lys Asp Lys Thr Ser Phe
                645                 650                 655

Asn Ile Gln Asp Leu Leu Thr Gln Pro His Pro Gly Phe Ala Asn Val
                660                 665                 670

Glu Gln Met Pro Leu Leu Asn Phe Thr Val Thr Ile Thr Asn Thr Gly
                675                 680                 685

Lys Val Ala Ser Asp Tyr Thr Ala Met Leu Phe Ala Asn Thr Thr Ala
690                 695                 700

Gly Pro Ala Pro Tyr Pro Asn Lys Trp Leu Val Gly Phe Asp Arg Leu
705                 710                 715                 720

Ala Ser Leu Glu Pro His Arg Ser Gln Thr Met Thr Ile Pro Val Thr
                725                 730                 735

Ile Asp Ser Val Ala Arg Thr Asp Glu Ala Gly Asn Arg Val Leu Tyr
                740                 745                 750

Pro Gly Lys Tyr Glu Leu Ala Leu Asn Asn Glu Arg Ser Val Val Leu
                755                 760                 765

Gln Phe Val Leu Thr Gly Arg Glu Ala Val Ile Phe Lys Trp Pro Val
                770                 775                 780

Glu Gln Gln Gln Ile Ser Ser Ala
785                 790
```

<210> SEQ ID NO 21
<211> LENGTH: 1660
<212> TYPE: DNA
<213> ORGANISM: Aspergillus fumigatus

<400> SEQUENCE: 21

```
atgactcttc tatttggtat atttcttgcc cggcttgcgg tggctgccgc ccagagcagc        60
tgcgtctcgg cttggtgagt cttcctcatg ctagagcctg cattttgcta agagtcaggg       120
gtcaatgtgg cggtatttct tataccgggt ctacctgctg tcagagtggg aatacctgcg       180
```

```
ccgagattaa ctcgtactac taccagtgca taccagcaac agctgtgagt gttatcccccc    240
cccccccccg agtggtttgt actggtcata acgcagagta gacttcaact accacagtga    300
catctccctc tagctctggt tcgtcttctg ccaacacgtc aggttataca acgacgactg    360
tcttgcccag tcccacagca acacagaacc cttatcctcc ggccaatgcc agctcatgtg    420
gatcgtgggc tctcgttgat aacgtttgct gcccatacta ctgtctctcg gataatgaat    480
ccgagtcctg cacgagcagc tgtaccggcg gctgcggcag tcctgattcc tccatgtgca    540
agtccgggac gatgtgtatg tgtgcacctt cgaagcgtga gcacggctga tacaaccaca    600
gggggagagc aacacaccgt aacttccaac gaggactggc attacagcgt gagcaattct    660
catcctgcct cggattcata ctgacgactg cagcgctcaa cacactttgg tctgaccagc    720
ggtggcgcct gcgggttcgg tctgtacggc ctctgcacca agaacagtgt caccgcgagc    780
tggacagacc caatgctggg ctctacctgc gacgccttct gcaccgcgta ccgctcctc     840
tgcaaagacc ccgctaacgt cactctccgc gggaactttg ctgccccgaa cggagactac    900
tacactcagg taagcacaca cacaggttct ccaagcgaca actcctaagt caatagttct    960
ggccttccct ggctgcatcc ggcaatcccg acaactacct ctcttgcggg gagtgtttcg   1020
aggtcatccg caccaagccc gacgggacag actacgccgt cggcgagagc ggatataccg   1080
accccatagt cctcgaggta gtagacagct gtccctgcaa tgccaattca aaatggtgct   1140
gtaagcgcac ccccccccc cccttcccc ttttttcccc gccttccaac ggacaaaatc     1200
tcacaagacc aggcggcagc ggcgcagacc actgcggcga aatcgacttc aagtacggct   1260
gtcctctgcc ggaaggatcc catcacatgg acctctccga tattgccatg gccgactcc    1320
agggaaacgg cagtctcgcc gacggtgtga ttcccatccg ctaccggcgt gtcccctgtc   1380
ccaagccggg gaacatctac atctggcttc atgatggggc gggaccgtat tatttttgcgc  1440
tgagcgcggt caataccaac gggcccggct ccgtaatcag tatcgaagtc caggctggtg   1500
gctccgggcc atgggttgcc ctcgagcacg atccgaacta ccagtagc cggccgcagg     1560
agcggtatgg ctcttgggtc ctcccgcagg gcaagggacc cattactgtg cctgtttcga   1620
tgaggctgac ggcgcccaat ggttaattaa ctagaggtga                         1660
```

<210> SEQ ID NO 22
<211> LENGTH: 470
<212> TYPE: PRT
<213> ORGANISM: Aspergillus fumigatus

<400> SEQUENCE: 22

```
Met Thr Leu Leu Phe Gly Ile Phe Leu Ala Arg Leu Ala Val Ala Ala
1               5                   10                  15

Ala Gln Ser Ser Cys Val Ser Ala Trp Gly Gln Cys Gly Gly Ile Ser
            20                  25                  30

Tyr Thr Gly Ser Thr Cys Cys Gln Ser Gly Asn Thr Cys Ala Glu Ile
        35                  40                  45

Asn Ser Tyr Tyr Tyr Gln Cys Ile Pro Ala Thr Ala Val Ser Thr Ser
    50                  55                  60

Thr Thr Thr Val Thr Ser Pro Ser Ser Gly Ser Ser Ser Ala Asn
65                  70                  75                  80

Thr Ser Gly Tyr Thr Thr Thr Val Leu Pro Ser Pro Thr Ala Thr
                85                  90                  95

Gln Asn Pro Tyr Pro Pro Ala Asn Ala Ser Ser Cys Gly Ser Trp Ala
            100                 105                 110
```

Leu Val Asp Asn Val Cys Cys Pro Tyr Tyr Cys Leu Ser Asp Asn Glu
            115                 120                 125

Ser Glu Ser Cys Thr Ser Cys Thr Gly Gly Cys Gly Ser Pro Asp
    130                 135                 140

Ser Ser Met Cys Lys Ser Gly Thr Met Trp Gly Glu Gln His Thr Val
145                 150                 155                 160

Thr Ser Asn Glu Asp Trp His Tyr Ser Arg Ser Thr His Phe Gly Leu
                165                 170                 175

Thr Ser Gly Gly Ala Cys Gly Phe Leu Tyr Gly Leu Cys Thr Lys
            180                 185                 190

Asn Ser Val Thr Ala Ser Trp Thr Asp Pro Met Leu Gly Ser Thr Cys
                195                 200                 205

Asp Ala Phe Cys Thr Ala Tyr Pro Leu Leu Cys Lys Asp Pro Ala Asn
            210                 215                 220

Val Thr Leu Arg Gly Asn Phe Ala Ala Pro Asn Gly Asp Tyr Tyr Thr
225                 230                 235                 240

Gln Phe Trp Pro Ser Leu Ala Ala Ser Gly Asn Pro Asp Asn Tyr Leu
                245                 250                 255

Ser Cys Gly Glu Cys Phe Glu Val Ile Arg Thr Lys Pro Asp Gly Thr
            260                 265                 270

Asp Tyr Ala Val Gly Glu Ser Gly Tyr Thr Asp Pro Ile Val Leu Glu
        275                 280                 285

Val Val Asp Ser Cys Pro Cys Asn Ala Asn Ser Lys Trp Cys Cys Lys
    290                 295                 300

Arg Thr Pro Pro Pro Leu Pro Leu Phe Ser Pro Ser Asn Gly
305                 310                 315                 320

Gln Asn Leu Thr Arg Pro Gly Gly Ser Gly Ala Asp His Cys Gly Glu
                325                 330                 335

Ile Asp Phe Lys Tyr Gly Cys Pro Leu Pro Glu Gly Ser His His Met
            340                 345                 350

Asp Leu Ser Asp Ile Ala Met Gly Arg Leu Gln Gly Asn Gly Ser Leu
            355                 360                 365

Ala Asp Gly Val Ile Pro Ile Arg Tyr Arg Arg Val Pro Cys Pro Lys
370                 375                 380

Pro Gly Asn Ile Tyr Ile Trp Leu His Asp Gly Ala Gly Pro Tyr Tyr
385                 390                 395                 400

Phe Ala Leu Ser Ala Val Asn Thr Asn Gly Pro Gly Ser Val Ile Ser
                405                 410                 415

Ile Glu Val Gln Ala Gly Gly Ser Gly Pro Trp Val Ala Leu Glu His
            420                 425                 430

Asp Pro Asn Tyr Thr Ser Ser Arg Pro Gln Glu Arg Tyr Gly Ser Trp
            435                 440                 445

Val Leu Pro Gln Gly Lys Gly Pro Ile Thr Val Pro Val Ser Met Arg
    450                 455                 460

Leu Thr Ala Pro Asn Gly
465                 470

<210> SEQ ID NO 23
<211> LENGTH: 1545
<212> TYPE: DNA
<213> ORGANISM: Trichoderma reesei

<400> SEQUENCE: 23
atgtatcgga agttggccgt catctcggcc ttcttggcca cagctcgtgc tcagtcggcc        60

```
tgcactctcc aatcggagac tcacccgcct ctgacatggc agaaatgctc gtctggtggc    120
acgtgcactc aacagacagg ctccgtggtc atcgacgcca actggcgctg gactcacgct    180
acgaacagca gcacgaactg ctacgatggc aacacttgga gctcgaccct atgtcctgac    240
aacgagacct cgcgcaagaa ctgctgtctg acggtgccg  cctacgcgtc cacgtacgga    300
gttaccacga gcggtaacag cctctccatt ggctttgtca cccagtctgc gcagaagaac    360
gttggcgctc gcctttacct tatggcgagc gacacgacct accaggaatt caccctgctt    420
ggcaacgagt tctctttcga tgttgatgtt tcgcagctgc cgtgcggctt gaacggagct    480
ctctacttcg tgtccatgga cgcggatggt ggcgtgagca agtatcccac caacaccgct    540
ggcgccaagt acggcacggg gtactgtgac agccagtgtc ccgcgatct  gaagttcatc    600 aatggccagg ccaacgttga gggctgggag ccgtcatcca acaacgcgaa acgggcatt    660 ggaggacacg gaagctgctg ctctgagatg gatatctggg aggccaactc catctccgag    720
gctcttaccc cccaccctg  cacgactgtc ggccaggaga tctgcgaggg tgatgggtgc    780
ggcggaactt actccgataa cagatatggc ggcacttgcg atcccgatgg ctgcgactgg    840
aacccatacc gcctgggcaa caccagcttc tacggccctg gctcaagctt taccctcgat    900
accaccaaga aattgaccgt tgtcacccag ttcgagacgt cgggtgccat caaccgatac    960
tatgtccaga atggcgtcac tttccagcag cccaacgccg agcttggtag ttactctggc    1020
aacgagctca cgatgatta  ctgcacagct gaggaggcag aattcggcgg atcctctttc    1080
tcagacaagg gcggcctgac tcagttcaag aaggctacct ctggcggcat ggttctggtc    1140
atgagtctgt gggatgatta ctacgccaac atgctgtggc tggactccac ctacccgaca    1200
aacgagacct cctccacacc cggtgccgtg cgcggaagct gctccaccag ctccggtgtc    1260
cctgctcagg tcgaatctca gtctcccaac gccaaggtca ccttctccaa catcaagttc    1320
ggacccattg gcagcaccgg caaccctagc ggcggcaacc ctcccggcgg aaacccgcct    1380
ggcaccacca ccacccgccg cccagccact accactggaa gctctcccgg acctacccag    1440
tctcactacg gccagtgcgg cggtattggc tacagcggcc ccacggtctg cgccagcggc    1500
acaacttgcc aggtcctgaa cccttactac tctcagtgcc tgtaa                   1545
```

<210> SEQ ID NO 24
<211> LENGTH: 514
<212> TYPE: PRT
<213> ORGANISM: Trichoderma reesei

<400> SEQUENCE: 24

Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
            115                 120                 125

Ala Ser Asp Thr Thr Tyr Gln Glu Phe Thr Leu Leu Gly Asn Glu Phe
130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
            195                 200                 205

Trp Glu Pro Ser Ser Asn Asn Ala Asn Thr Gly Ile Gly Gly His Gly
            210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
            245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
            275                 280                 285

Ser Phe Tyr Gly Pro Gly Ser Ser Phe Thr Leu Asp Thr Thr Lys Lys
            290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
            325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
            355                 360                 365

Phe Lys Lys Ala Thr Ser Gly Gly Met Val Leu Val Met Ser Leu Trp
            370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
            405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
            435                 440                 445

Pro Ser Gly Gly Asn Pro Pro Gly Gly Asn Pro Pro Gly Thr Thr Thr
450                 455                 460

Thr Arg Arg Pro Ala Thr Thr Thr Gly Ser Ser Pro Gly Pro Thr Gln
465                 470                 475                 480

Ser His Tyr Gly Gln Cys Gly Gly Ile Gly Tyr Ser Gly Pro Thr Val
            485                 490                 495

Cys Ala Ser Gly Thr Thr Cys Gln Val Leu Asn Pro Tyr Tyr Ser Gln
            500                 505                 510

Cys Leu

<210> SEQ ID NO 25

<211> LENGTH: 1611
<212> TYPE: DNA
<213> ORGANISM: Trichoderma reesei

<400> SEQUENCE: 25

```
atgattgtcg gcattctcac cacgctggct acgctggcca cactcgcagc tagtgtgcct      60
ctagaggagc ggcaagcttg ctcaagcgtc tggtaattat gtgaaccctc tcaagagacc     120
caaatactga gatatgtcaa ggggccaatg tggtggccag aattggtcgg gtccgacttg     180
ctgtgcttcc ggaagcacat gcgtctactc caacgactat tactcccagt gtcttcccgg     240
cgctgcaagc tcaagctcgt ccacgcgcgc gcgtcgacg acttctcgag tatccccccac     300
aacatcccgg tcgagctccg cgacgcctcc acctggttct actactacca gagtacctcc     360
agtcggatcg ggaaccgcta cgtattcagg caaccctttt gttggggtca ctccttgggc     420
caatgcatat tacgcctctg aagttagcag cctcgctatt cctagcttga ctggagccat     480
ggccactgct gcagcagctg tcgcaaaggt tccctctttt atgtggctgt aggtcctccc     540
ggaaccaagg caatctgtta ctgaaggctc atcattcact gcagagatac tcttgacaag     600
accectctca tggagcaaac cttggccgac atccgcaccg ccaacaagaa tggcggtaac     660
tatgccggac agttgtggt gtatgacttg ccggatcgcg attgcgctgc ccttgcctcg     720
aatggcgaat actctattgc cgatggtggc gtcgccaaat ataagaacta tatcgacacc     780
attcgtcaaa ttgtcgtgga atattccgat atccggaccc tcctggttat tggtatgagt     840
ttaaacacct gcctccccccc ccccttcctt tcctttcccg ccggcatctt gtcgttgtgc     900
taactattgt tccctcttcc agagcctgac tctcttgcca actggtgac caacctcggt     960
actccaaagt gtgccaatgc tcagtcagcc taccttgagt gcatcaacta cgccgtcaca    1020
cagctgaacc ttccaaatgt tgcgatgtat ttggacgctg ccatgcagg atggcttggc    1080
tggccggcaa accaagaccc ggccgctcag ctatttgcaa atgtttacaa gaatgcatcg    1140
tctccgagag ctcttcgcgg attggcaacc aatgtcgcca actacaacgg gtggaacatt    1200
accagccccc catcgtacac gcaaggcaac gctgtctaca cgagaagct gtacatccac    1260
gctattggac gtcttcttgc caatcacggc tggtccaacg ccttcttcat cactgatcaa    1320
ggtcgatcgg gaaagcagcc taccggacag caacagtggg gagactggtg caatgtgatc    1380
ggcaccggat ttggtattcg cccatccgca aacactgggg actcgttgct ggattcgttt    1440
gtctgggtca agccaggcgg cgagtgtgac ggcaccagcg acagcagtgc gccacgattt    1500
gactcccact gtgcgctccc agatgccttg caaccgcgc ctcaagctgg tgcttggttc    1560
caagcctact ttgtgcagct tctcacaaac gcaaacccat cgttcctgta a             1611
```

<210> SEQ ID NO 26
<211> LENGTH: 471
<212> TYPE: PRT
<213> ORGANISM: Trichoderma reesei

<400> SEQUENCE: 26

```
Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
            20                  25                  30

Gln Cys Gly Gly Gln Asn Trp Ser Gly Pro Thr Cys Cys Ala Ser Gly
        35                  40                  45

Ser Thr Cys Val Tyr Ser Asn Asp Tyr Tyr Ser Gln Cys Leu Pro Gly
    50                  55                  60
```

```
Ala Ala Ser Ser Ser Ser Thr Arg Ala Ser Thr Ser Arg
 65                  70                  75                  80

Val Ser Pro Thr Thr Ser Arg Ser Ser Ala Thr Pro Pro Gly
                     85                  90                  95

Ser Thr Thr Thr Arg Val Pro Pro Val Gly Ser Gly Thr Ala Thr Tyr
                100                 105                 110

Ser Gly Asn Pro Phe Val Gly Val Thr Pro Trp Ala Asn Ala Tyr Tyr
            115                 120                 125

Ala Ser Glu Val Ser Ser Leu Ala Ile Pro Ser Leu Thr Gly Ala Met
        130                 135                 140

Ala Thr Ala Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
            180                 185                 190

Tyr Asp Leu Pro Asp Arg Asp Cys Ala Ala Leu Ala Ser Asn Gly Glu
        195                 200                 205

Tyr Ser Ile Ala Asp Gly Gly Val Ala Lys Tyr Lys Asn Tyr Ile Asp
210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
        275                 280                 285

Gly His Ala Gly Trp Leu Gly Trp Pro Ala Asn Gln Asp Pro Ala Ala
    290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
            340                 345                 350

Tyr Ile His Ala Ile Gly Arg Leu Leu Ala Asn His Gly Trp Ser Asn
        355                 360                 365

Ala Phe Phe Ile Thr Asp Gln Gly Arg Ser Gly Lys Gln Pro Thr Gly
    370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
            420                 425                 430

Pro Arg Phe Asp Ser His Cys Ala Leu Pro Asp Ala Leu Gln Pro Ala
        435                 440                 445

Pro Gln Ala Gly Ala Trp Phe Gln Ala Tyr Phe Val Gln Leu Leu Thr
    450                 455                 460

Asn Ala Asn Pro Ser Phe Leu
465                 470
```

<210> SEQ ID NO 27
<211> LENGTH: 2615
<212> TYPE: DNA
<213> ORGANISM: Trichoderma reesei

<400> SEQUENCE: 27

| | | | | | |
|---|---|---|---|---|---|
| atgggatttg | gccgcaatgc | tgccgagccc | gagtgtttct | gcaacgttat | ccaggagatt | 60 |
| tgcgcttgcc | caagagggag | ttgacgggga | gagtcccaac | tggttccttc | agtaacgcca | 120 |
| ccctggcaga | ctatataact | tgtggacaag | actctgcttt | gttgagttct | tcctaccagt | 180 |
| cttgaccaag | accattctgt | tgagcccaat | cagaaatgcg | ttaccgaaca | gcagctgcgc | 240 |
| tggcacttgc | cactgggccc | tttgctaggg | cagacagtca | gtatagctgg | tccatactgg | 300 |
| gatgtatatg | tatcctggag | acaccatgct | gactcttgaa | tcaaggtagc | tcaacatcgg | 360 |
| gggcctcggc | tgaggcagtt | gtacctcctg | cagggactcc | atgggaaacc | gcgtacgaca | 420 |
| aggcgaaggc | cgcattggca | aagctcaatc | tccaagataa | ggtcggcatc | gtgagcggtg | 480 |
| tcggctggaa | cggcggtcct | tgcgttggaa | acacatctcc | ggcctccaag | atcagctatc | 540 |
| catcgctatg | ccttcaagac | ggaccctcg | gtgttcgata | ctcgacaggc | agcacagcct | 600 |
| ttacgccggc | cgttcaagcg | gcctcgacgt | gggatgtcaa | tttgatccgc | gaacgtggac | 660 |
| agttcatcgg | tgaggaggtg | aaggcctcgg | ggattcatgt | catacttggt | cctgtggctg | 720 |
| ggccgctggg | aaagactccg | cagggcggtc | gcaactggga | gggcttcggt | gtcgatccat | 780 |
| atctcacggg | cattgccatg | ggtcaaacca | tcaacggcat | ccagtcggta | ggcgtgcagg | 840 |
| cgacagcgaa | gcactatatc | ctcaacgagc | aggagctcaa | tcgagaaacc | atttcgagca | 900 |
| acccagatga | ccgaactctc | catgagctgt | atacttggcc | atttgccgac | gcggttcagg | 960 |
| ccaatgtcgc | ttctgtcatg | tgctcgtaca | acaaggtcaa | taccacctgg | gcctgcgagg | 1020 |
| atcagtacac | gctgcagact | gtgctgaaag | accagctggg | gttcccaggc | tatgtcatga | 1080 |
| cggactggaa | cgcacagcac | acgactgtcc | aaagcgcgaa | ttctgggctt | gacatgtcaa | 1140 |
| tgcctggcac | agacttcaac | ggtaacaatc | ggctctgggg | tccagctctc | accaatgcgg | 1200 |
| taaatagcaa | tcaggtcccc | acgagcagag | tcgacgatat | ggtgactcgt | atcctcgccg | 1260 |
| catggtactt | gacaggccag | gaccaggcag | gctatccgtc | gttcaacatc | agcagaaatg | 1320 |
| ttcaaggaaa | ccacaagacc | aatgtcaggg | caattgccag | ggacggcatc | gttctgctca | 1380 |
| agaatgacgc | caacatcctg | ccgctcaaga | agcccgctag | cattgccgtc | gttggatctg | 1440 |
| ccgcaatcat | tggtaaccac | gccagaaact | cgccctcgtg | caacgacaaa | ggctgcgacg | 1500 |
| acggggcctt | gggcatgggt | tggggttccg | gcgccgtcaa | ctatccgtac | ttcgtcgcgc | 1560 |
| cctacgatgc | catcaatacc | agagcgtctt | cgcagggcac | ccaggttacc | ttgagcaaca | 1620 |
| ccgacaacac | gtcctcaggc | gcatctgcag | caagaggaaa | ggacgtcgcc | atcgtcttca | 1680 |
| tcaccgccga | ctcgggtgaa | ggctacatca | ccgtggaggg | caacgcgggc | gatcgcaaca | 1740 |
| acctggatcc | gtggcacaac | ggcaatgccc | tggtccaggc | ggtggccggt | gccaacagca | 1800 |
| acgtcattgt | tgttgtccac | tccgttggcg | ccatcattct | ggagcagatt | cttgctcttc | 1860 |
| cgcaggtcaa | ggccgttgtc | tgggcgggtc | ttccttctca | ggagagcggc | aatgcgctcg | 1920 |
| tcgacgtgct | gtggggagat | gtcagcccct | tctggcaagct | ggtgtacacc | attgcgaaga | 1980 |
| gccccaatga | ctataacact | cgcatcgttt | ccggcggcag | tgcagcttc | agcgagggac | 2040 |
| tgttcatcga | ctataagcac | ttcgacgacg | ccaatatcac | gccgcggtac | gagttcggct | 2100 |
| atggactgtg | taagtttgct | aacctgaaca | atctattaga | caggttgact | gacggatgac | 2160 |

```
tgtggaatga tagcttacac caagttcaac tactcacgcc tctccgtctt gtcgaccgcc    2220
aagtctggtc ctgcgactgg ggccgttgtg ccgggaggcc cgagtgatct gttccagaat    2280
gtcgcgacag tcaccgttga catcgcaaac tctggccaag tgactggtgc cgaggtagcc    2340
cagctgtaca tcacctaccc atcttcagca cccaggaccc ctccgaagca gctgcgaggc    2400
tttgccaagc tgaacctcac gcctggtcag agcggaacag caacgttcaa catccgacga    2460
cgagatctca gctactggga cacggcttcg cagaaatggg tggtgccgtc ggggtcgttt    2520
ggcatcagcg tgggagcgag cagccgggat atcaggctga cgagcactct gtcggtagcg    2580
tagcgcgagg agggtgaagg cggttgacct gtgac                              2615
```

<210> SEQ ID NO 28
<211> LENGTH: 744
<212> TYPE: PRT
<213> ORGANISM: Trichoderma reesei

<400> SEQUENCE: 28

```
Met Arg Tyr Arg Thr Ala Ala Leu Ala Leu Ala Thr Gly Pro Phe
1               5                   10                  15

Ala Arg Ala Asp Ser His Ser Thr Ser Gly Ala Ser Ala Glu Ala Val
                20                  25                  30

Val Pro Pro Ala Gly Thr Pro Trp Gly Thr Ala Tyr Asp Lys Ala Lys
            35                  40                  45

Ala Ala Leu Ala Lys Leu Asn Leu Gln Asp Lys Val Gly Ile Val Ser
        50                  55                  60

Gly Val Gly Trp Asn Gly Gly Pro Cys Val Gly Asn Thr Ser Pro Ala
65                  70                  75                  80

Ser Lys Ile Ser Tyr Pro Ser Leu Cys Leu Gln Asp Gly Pro Leu Gly
                85                  90                  95

Val Arg Tyr Ser Thr Gly Ser Thr Ala Phe Thr Pro Gly Val Gln Ala
            100                 105                 110

Ala Ser Thr Trp Asp Val Asn Leu Ile Arg Glu Arg Gly Gln Phe Ile
        115                 120                 125

Gly Glu Glu Val Lys Ala Ser Gly Ile His Val Ile Leu Gly Pro Val
    130                 135                 140

Ala Gly Pro Leu Gly Lys Thr Pro Gln Gly Gly Arg Asn Trp Glu Gly
145                 150                 155                 160

Phe Gly Val Asp Pro Tyr Leu Thr Gly Ile Ala Met Gly Gln Thr Ile
                165                 170                 175

Asn Gly Ile Gln Ser Val Gly Val Gln Ala Thr Ala Lys His Tyr Ile
            180                 185                 190

Leu Asn Glu Gln Glu Leu Asn Arg Glu Thr Ile Ser Ser Asn Pro Asp
        195                 200                 205

Asp Arg Thr Leu His Glu Leu Tyr Thr Trp Pro Phe Ala Asp Ala Val
    210                 215                 220

Gln Ala Asn Val Ala Ser Val Met Cys Ser Tyr Asn Lys Val Asn Thr
225                 230                 235                 240

Thr Trp Ala Cys Glu Asp Gln Tyr Thr Leu Gln Thr Val Leu Lys Asp
                245                 250                 255

Gln Leu Gly Phe Pro Gly Tyr Val Met Thr Asp Trp Asn Ala Gln His
            260                 265                 270

Thr Thr Val Gln Ser Ala Asn Ser Gly Leu Asp Met Ser Met Pro Gly
        275                 280                 285
```

```
            -continued

Thr Asp Phe Asn Gly Asn Asn Arg Leu Trp Gly Pro Ala Leu Thr Asn
    290                 295                 300

Ala Val Asn Ser Asn Gln Val Pro Thr Ser Arg Val Asp Asp Met Val
305                 310                 315                 320

Thr Arg Ile Leu Ala Ala Trp Tyr Leu Thr Gly Gln Asp Gln Ala Gly
                325                 330                 335

Tyr Pro Ser Phe Asn Ile Ser Arg Asn Val Gln Gly Asn His Lys Thr
                340                 345                 350

Asn Val Arg Ala Ile Ala Arg Asp Gly Ile Val Leu Leu Lys Asn Asp
            355                 360                 365

Ala Asn Ile Leu Pro Leu Lys Lys Pro Ala Ser Ile Ala Val Val Gly
        370                 375                 380

Ser Ala Ala Ile Ile Gly Asn His Ala Arg Asn Ser Pro Ser Cys Asn
385                 390                 395                 400

Asp Lys Gly Cys Asp Asp Gly Ala Leu Gly Met Gly Trp Gly Ser Gly
                405                 410                 415

Ala Val Asn Tyr Pro Tyr Phe Val Ala Pro Tyr Asp Ala Ile Asn Thr
                420                 425                 430

Arg Ala Ser Ser Gln Gly Thr Gln Val Thr Leu Ser Asn Thr Asp Asn
            435                 440                 445

Thr Ser Ser Gly Ala Ser Ala Ala Arg Gly Lys Asp Val Ala Ile Val
    450                 455                 460

Phe Ile Thr Ala Asp Ser Gly Glu Gly Tyr Ile Thr Val Glu Gly Asn
465                 470                 475                 480

Ala Gly Asp Arg Asn Asn Leu Asp Pro Trp His Asn Gly Asn Ala Leu
                485                 490                 495

Val Gln Ala Val Ala Gly Ala Asn Ser Asn Val Ile Val Val His Ser
            500                 505                 510

Ser Val Gly Ala Ile Ile Leu Glu Gln Ile Leu Ala Leu Pro Gln Val
    515                 520                 525

Lys Ala Val Val Trp Ala Gly Leu Pro Ser Gln Glu Ser Gly Asn Ala
530                 535                 540

Leu Val Asp Val Leu Trp Gly Asp Val Ser Pro Ser Gly Lys Leu Val
545                 550                 555                 560

Tyr Thr Ile Ala Lys Ser Pro Asn Asp Tyr Asn Thr Arg Ile Val Ser
                565                 570                 575

Gly Gly Ser Asp Ser Phe Ser Glu Gly Leu Phe Ile Asp Tyr Lys His
            580                 585                 590

Phe Asp Asp Ala Asn Ile Thr Pro Arg Tyr Glu Phe Gly Tyr Gly Leu
        595                 600                 605

Ser Tyr Thr Lys Phe Asn Tyr Ser Arg Leu Ser Val Leu Ser Thr Ala
    610                 615                 620

Lys Ser Gly Pro Ala Thr Gly Ala Val Val Pro Gly Gly Pro Ser Asp
625                 630                 635                 640

Leu Phe Gln Asn Val Ala Thr Val Thr Val Asp Ile Ala Asn Ser Gly
                645                 650                 655

Gln Val Thr Gly Ala Glu Val Ala Gln Leu Tyr Ile Thr Tyr Pro Ser
            660                 665                 670

Ser Ala Pro Arg Thr Pro Pro Lys Gln Leu Arg Gly Phe Ala Lys Leu
        675                 680                 685

Asn Leu Thr Pro Gly Gln Ser Gly Thr Ala Thr Phe Asn Ile Arg Arg
    690                 695                 700

Arg Asp Leu Ser Tyr Trp Asp Thr Ala Ser Gln Lys Trp Val Val Pro
```

```
                705                 710                 715                 720
            Ser Gly Ser Phe Gly Ile Ser Val Gly Ala Ser Ser Arg Asp Ile Arg
                            725                 730                 735

Leu Thr Ser Thr Leu Ser Val Ala
                        740

<210> SEQ ID NO 29
<211> LENGTH: 1377
<212> TYPE: DNA
<213> ORGANISM: Trichoderma reesei

<400> SEQUENCE: 29
atggcgccct cagttacact gccgttgacc acggccatcc tggccattgc ccggctcgtc      60
gccgcccagc aaccgggtac cagcaccccc gaggtccatc ccaagttgac aacctacaag     120
tgtacaaagt ccggggggtg cgtggcccag gacacctcgg tggtccttga ctggaactac     180
cgctggatgc acgacgcaaa ctacaactcg tgcaccgtca acggcggcgt caacaccacg     240
ctctgccctg acgaggcgac ctgtggcaag aactgcttca tcgagggcgt cgactacgcc     300
gcctcgggcg tcacgacctc gggcagcagc ctcaccatga accagtacat gccagcagc     360 tctggcggct acagcagcgt ctctcctcgg ctgtatctcc tggactctga cggtgagtac     420
gtgatgctga agctcaacgg ccaggagctg agcttcgacg tcgacctctc tgctctgccg     480
tgtggagaga acggctcgct ctacctgtct cagatggacg agaacggggg cgccaaccag     540
tataacacgg ccggtgccaa ctacgggagc ggctactgcg atgctcagtg ccccgtccag     600
acatggagga acggcaccct caacactagc caccagggct ctgctgcaa cgagatggat     660 atcctggagg gcaactcgag ggcgaatgcc ttgacccctc actcttgcac ggccacggcc     720
tgcgactctg ccggttgcgg cttcaacccc tatggcagcg gctacaaaag ctactacggc     780
cccggagata ccgttgacac ctccaagacc ttcaccatca tcacccagtt caacacggac     840
aacggctcgc cctcgggcaa ccttgtgagc atcacccgca agtaccagca aaacggcgtc     900
gacatcccca gcgcccagcc cggcggcgac accatctcgt cctgcccgtc cgcctcagcc     960
tacgcgggcc tcgccaccat gggcaaggcc ctgagcagcg gcatggtgct cgtgttcagc    1020
atttggaacg acaacagcca gtacatgaac tggctcgaca gcggcaacgc cggcccctgc    1080
agcagcaccg agggcaaccc atccaacatc tggccaaca accccaacac gcacgtcgtc    1140
ttctccaaca tccgctgggg agacattggg tctactacga actcgactgc gccccgccc    1200 ccgcctgcgt ccagcacgac gttttcgact acacggagga gctcgacgac ttcgagcagc    1260
ccgagctgca cgcagactca ctgggggcag tgcggtggca ttgggtacag cgggtgcaag    1320
acgtgcacgt cgggcactac gtgccagtat agcaacgact actactcgca atgcctt       1377

<210> SEQ ID NO 30
<211> LENGTH: 459
<212> TYPE: PRT
<213> ORGANISM: Trichoderma reesei

<400> SEQUENCE: 30

Met Ala Pro Ser Val Thr Leu Pro Leu Thr Thr Ala Ile Leu Ala Ile
1               5                   10                  15

Ala Arg Leu Val Ala Ala Gln Gln Pro Gly Thr Ser Thr Pro Glu Val
            20                  25                  30

His Pro Lys Leu Thr Thr Tyr Lys Cys Thr Lys Ser Gly Gly Cys Val
        35                  40                  45
```

-continued

```
Ala Gln Asp Thr Ser Val Val Leu Asp Trp Asn Tyr Arg Trp Met His
    50                  55                  60

Asp Ala Asn Tyr Asn Ser Cys Thr Val Asn Gly Gly Val Asn Thr Thr
65                  70                  75                  80

Leu Cys Pro Asp Glu Ala Thr Cys Gly Lys Asn Cys Phe Ile Glu Gly
                85                  90                  95

Val Asp Tyr Ala Ala Ser Gly Val Thr Thr Ser Gly Ser Ser Leu Thr
            100                 105                 110

Met Asn Gln Tyr Met Pro Ser Ser Gly Gly Tyr Ser Ser Val Ser
            115                 120                 125

Pro Arg Leu Tyr Leu Leu Asp Ser Asp Gly Glu Tyr Val Met Leu Lys
        130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175

Gly Ala Asn Gln Tyr Asn Thr Ala Gly Ala Asn Tyr Gly Ser Gly Tyr
            180                 185                 190

Cys Asp Ala Gln Cys Pro Val Gln Thr Trp Arg Asn Gly Thr Leu Asn
            195                 200                 205

Thr Ser His Gln Gly Phe Cys Cys Asn Glu Met Asp Ile Leu Glu Gly
        210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
                245                 250                 255

Ser Tyr Tyr Gly Pro Gly Asp Thr Val Asp Thr Ser Lys Thr Phe Thr
            260                 265                 270

Ile Ile Thr Gln Phe Asn Thr Asp Asn Gly Ser Pro Ser Gly Asn Leu
        275                 280                 285

Val Ser Ile Thr Arg Lys Tyr Gln Gln Asn Gly Val Asp Ile Pro Ser
        290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
                325                 330                 335

Leu Val Phe Ser Ile Trp Asn Asp Asn Ser Gln Tyr Met Asn Trp Leu
            340                 345                 350

Asp Ser Gly Asn Ala Gly Pro Cys Ser Ser Thr Glu Gly Asn Pro Ser
        355                 360                 365

Asn Ile Leu Ala Asn Asn Pro Asn Thr His Val Val Phe Ser Asn Ile
        370                 375                 380

Arg Trp Gly Asp Ile Gly Ser Thr Thr Asn Ser Thr Ala Pro Pro Pro
385                 390                 395                 400

Pro Pro Ala Ser Ser Thr Thr Phe Ser Thr Thr Arg Arg Ser Ser Thr
                405                 410                 415

Thr Ser Ser Ser Pro Ser Cys Thr Gln Thr His Trp Gly Gln Cys Gly
            420                 425                 430

Gly Ile Gly Tyr Ser Gly Cys Lys Thr Cys Thr Ser Gly Thr Thr Cys
        435                 440                 445

Gln Tyr Ser Asn Asp Tyr Tyr Ser Gln Cys Leu
        450                 455
```

<210> SEQ ID NO 31
<211> LENGTH: 1254
<212> TYPE: DNA
<213> ORGANISM: Trichoderma reesei

<400> SEQUENCE: 31

```
atgaacaagt ccgtggctcc attgctgctt gcagcgtcca tactatatgg cggcgccgtc      60
gcacagcaga ctgtctgggg ccagtgtgga ggtattggtt ggagcggacc tacgaattgt     120
gctcctggct cagcttgttc gaccctcaat ccttattatg cgcaatgtat tccgggagcc     180
actactatca ccacttcgac ccggccacca tccggtccaa ccaccaccac cagggctacc     240
tcaacaagct catcaactcc acccacgagc tctggggtcc gatttgccgg cgttaacatc     300
gcgggttttg actttggctg taccacagat ggcacttgcg ttacctcgaa ggtttatcct     360
ccgttgaaga acttcaccgg ctcaaacaac taccccgatg catcggcca gatgcagcac     420
tcgtcaacg aggacgggat gactattttc gcttacctg tcggatggca gtacctcgtc     480
aacaacaatt tgggcggcaa tcttgattcc acgagcattt ccaagtatga tcagcttgtt     540
cagggggtgcc tgtctctggg cgcatactgc atcgtcgaca tccacaatta tgctcgatgg     600
aacggtggga tcattggtca gggcggccct actaatgctc aattcacgag cctttggtcg     660
cagttggcat caaagtacgc atctcagtcg agggtgtggt tcggcatcat gaatgagccc     720
cacgacgtga acatcaacac ctgggctgcc acggtccaag aggttgtaac cgcaatccgc     780
aacgctggtg ctacgtcgca attcatctct ttgcctggaa atgattggca atctgctggg     840
gctttcatat ccgatggcag tgcagccgcc ctgtctcaag tcacgaaccc ggatgggtca     900
acaacgaatc tgattttga cgtgcacaaa tacttggact cagacaactc cggtactcac     960
gccgaatgta ctacaaataa cattgacggc gccttttctc cgcttgccac ttggctccga    1020
cagaacaatc gccaggctat cctgacagaa accggtggtg gcaacgttca gtcctgcata    1080
caagacatgt gccagcaaat ccaatatctc aaccagaact cagatgtcta tcttggctat    1140
gttggttggg gtgccggatc atttgatagc acgtatgtcc tgacggaaac accgactagc    1200
agtggtaact catggacgga cacatccttg gtcagctcgt gtctcgcaag aaag         1254
```

<210> SEQ ID NO 32
<211> LENGTH: 418
<212> TYPE: PRT
<213> ORGANISM: Trichoderma reesei

<400> SEQUENCE: 32

Met Asn Lys Ser Val Ala Pro Leu Leu Ala Ser Ile Leu Tyr
1               5                   10                  15

Gly Gly Ala Val Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser

|           |           |           |           | 115       |           |           |           |           | 120       |           |           |           |           | 125       |           |
Asn Asn Tyr Pro Asp Gly Ile Gly Gln Met Gln His Phe Val Asn Glu
            130                     135                     140

Asp Gly Met Thr Ile Phe Arg Leu Pro Val Gly Trp Gln Tyr Leu Val
145                     150                     155                     160

Asn Asn Asn Leu Gly Gly Asn Leu Asp Ser Thr Ser Ile Ser Lys Tyr
                        165                     170                     175

Asp Gln Leu Val Gln Gly Cys Leu Ser Leu Gly Ala Tyr Cys Ile Val
            180                     185                     190

Asp Ile His Asn Tyr Ala Arg Trp Asn Gly Gly Ile Ile Gly Gln Gly
            195                     200                     205

Gly Pro Thr Asn Ala Gln Phe Thr Ser Leu Trp Ser Gln Leu Ala Ser
    210                     215                     220

Lys Tyr Ala Ser Gln Ser Arg Val Trp Phe Gly Ile Met Asn Glu Pro
225                     230                     235                     240

His Asp Val Asn Ile Asn Thr Trp Ala Ala Thr Val Gln Glu Val Val
                        245                     250                     255

Thr Ala Ile Arg Asn Ala Gly Ala Thr Ser Gln Phe Ile Ser Leu Pro
            260                     265                     270

Gly Asn Asp Trp Gln Ser Ala Gly Ala Phe Ile Ser Asp Gly Ser Ala
            275                     280                     285

Ala Ala Leu Ser Gln Val Thr Asn Pro Asp Gly Ser Thr Thr Asn Leu
    290                     295                     300

Ile Phe Asp Val His Lys Tyr Leu Asp Ser Asp Asn Ser Gly Thr His
305                     310                     315                     320

Ala Glu Cys Thr Thr Asn Asn Ile Asp Gly Ala Phe Ser Pro Leu Ala
                        325                     330                     335

Thr Trp Leu Arg Gln Asn Asn Arg Gln Ala Ile Leu Thr Glu Thr Gly
            340                     345                     350

Gly Gly Asn Val Gln Ser Cys Ile Gln Asp Met Cys Gln Gln Ile Gln
            355                     360                     365

Tyr Leu Asn Gln Asn Ser Asp Val Tyr Leu Gly Tyr Val Gly Trp Gly
    370                     375                     380

Ala Gly Ser Phe Asp Ser Thr Tyr Val Leu Thr Glu Thr Pro Thr Ser
385                     390                     395                     400

Ser Gly Asn Ser Trp Thr Asp Thr Ser Leu Val Ser Ser Cys Leu Ala
                        405                     410                     415

Arg Lys

<210> SEQ ID NO 33
<211> LENGTH: 752
<212> TYPE: DNA
<213> ORGANISM: Trichoderma reesei

<400> SEQUENCE: 33
atggttgcct tttccagcct catctgcgct ctcaccagca tcgccagtac tctggcgatg       60
cccacaggcc tcgagcctga gagcagtgtc aacgtcacag agcgtggcat gtacgacttt      120
gttcttggag ctcacaatga tcatcgccgt cgtgctagca tcaactacga ccaaaactac      180
caaactggcg gacaagtcag ctattcgcct tccaacactg gcttctcagt gaactggaac      240
actcaagatg actttgttgt gggcgttggt tggacgactg atcttctgc gtaggaggac       300 tcctcatcat tctgcacttt gaaagcatct tctgaccaaa agcttctctt agtcccatca      360
actttggcgg ctcttttagt gtcaacagcg gaactggcct gctttccgtc tatggctgga      420

```
gcaccaaccc actggttgag tactacatca tggaggacaa ccacaactac ccagcacagg    480
gtaccgtcaa gggaaccgtc accagcgacg gagccactta caccatctgg gagaataccc    540
gtgtcaacga gccttccatc cagggcacag cgaccttcaa ccagtacatt tccgtgcgga    600
actcgcccag gaccagcgga actgttactg tgcagaacca cttcaatgct gggcctcgc     660 ttggcctgca ccttgggcag atgaactacc aggttgtcgc tgtcgaaggc tggggtggta    720
gtggttctgc ctcacagagt gtcagcaact ag                                  752
```

<210> SEQ ID NO 34
<211> LENGTH: 229
<212> TYPE: PRT
<213> ORGANISM: Trichoderma reesei

<400> SEQUENCE: 34

```
Met Val Ala Phe Ser Ser Leu Ile Cys Ala Leu Thr Ser Ile Ala Ser
1               5                   10                  15

Thr Leu Ala Met Pro Thr Gly Leu Glu Pro Glu Ser Ser Val Asn Val
            20                  25                  30

Thr Glu Arg Gly Met Tyr Asp Phe Val Leu Gly Ala His Asn Asp His
        35                  40                  45

Arg Arg Arg Ala Ser Ile Asn Tyr Asp Gln Asn Tyr Gln Thr Gly Gly
    50                  55                  60

Gln Val Ser Tyr Ser Pro Ser Asn Thr Gly Phe Ser Val Asn Trp Asn
65                  70                  75                  80

Thr Gln Asp Asp Phe Val Val Gly Val Gly Trp Thr Thr Gly Ser Ser
                85                  90                  95

Ala Pro Ile Asn Phe Gly Gly Ser Phe Ser Val Asn Ser Gly Thr Gly
            100                 105                 110

Leu Leu Ser Val Tyr Gly Trp Ser Thr Asn Pro Leu Val Glu Tyr Tyr
        115                 120                 125

Ile Met Glu Asp Asn His Asn Tyr Pro Ala Gln Gly Thr Val Lys Gly
    130                 135                 140

Thr Val Thr Ser Asp Gly Ala Thr Tyr Thr Ile Trp Glu Asn Thr Arg
145                 150                 155                 160

Val Asn Glu Pro Ser Ile Gln Gly Thr Ala Thr Phe Asn Gln Tyr Ile
                165                 170                 175

Ser Val Arg Asn Ser Pro Arg Thr Ser Gly Thr Val Thr Val Gln Asn
            180                 185                 190

His Phe Asn Ala Trp Ala Ser Leu Gly Leu His Leu Gly Gln Met Asn
        195                 200                 205

Tyr Gln Val Val Ala Val Glu Gly Trp Gly Gly Ser Gly Ser Ala Ser
    210                 215                 220

Gln Ser Val Ser Asn
225
```

<210> SEQ ID NO 35
<211> LENGTH: 796
<212> TYPE: DNA
<213> ORGANISM: Trichoderma reesei

<400> SEQUENCE: 35

```
caagaagaca tcaacatggt ctccttcacc tccctcctcg ccggcgtcgc cgccatctcg    60
ggcgtcttgg ccgctcccgc cgccgaggtc gaatccgtgg ctgtggagaa gcgcagacg    120 attcagcccg gcacgggcta caacaacggc tacttctact cgtactggaa cgatggccac    180
```

```
ggcggcgtga cgtacaccaa tggtcccggc gggcagttct ccgtcaactg gtccaactcg    240
ggcaactttg tcggcggcaa gggatggcag cccggcacca agaacaagta agactaccta    300
ctcttacccc ctttgaccaa cacagcacaa cacaatacaa cacatgtgac taccaatcat    360
ggaatcggat ctaacagctg tgttttcaaa aaaaagggtc atcaacttct cgggcagcta    420
caaccccaac ggcaacagct acctctccgt gtacggctgg tcccgcaacc ccctgatcga    480
gtactacatc gtcgagaact ttggcaccta caacccgtcc acgggcgcca ccaagctggg    540
cgaggtcacc tccgacggca gcgtctacga catttaccgc acgcagcgcg tcaaccagcc    600
gtccatcatc ggcaccgcca ccttttacca gtactggtcc gtccgccgca accaccgctc    660
gagcggctcc gtcaacacgg cgaaccactt caacgcgtgg gctcagcaag gcctgacgct    720
cgggacgatg gattaccaga ttgttgccgt ggagggttac tttagctctg gctctgcttc    780
catcaccgtc agctaa                                                    796
```

```
<210> SEQ ID NO 36
<211> LENGTH: 223
<212> TYPE: PRT
<213> ORGANISM: Trichoderma reesei

<400> SEQUENCE: 36

Met Val Ser Phe Thr Ser Leu Leu Ala Gly Val Ala Ala Ile Ser Gly
1               5                   10                  15

Val Leu Ala Ala Pro Ala Ala Glu Val Glu Ser Val Ala Val Glu Lys
            20                  25                  30

Arg Gln Thr Ile Gln Pro Gly Thr Gly Tyr Asn Asn Gly Tyr Phe Tyr
        35                  40                  45

Ser Tyr Trp Asn Asp Gly His Gly Gly Val Thr Tyr Thr Asn Gly Pro
    50                  55                  60

Gly Gly Gln Phe Ser Val Asn Trp Ser Asn Ser Gly Asn Phe Val Gly
65                  70                  75                  80

Gly Lys Gly Trp Gln Pro Gly Thr Lys Asn Lys Val Ile Asn Phe Ser
                85                  90                  95

Gly Ser Tyr Asn Pro Asn Gly Asn Ser Tyr Leu Ser Val Tyr Gly Trp
            100                 105                 110

Ser Arg Asn Pro Leu Ile Glu Tyr Tyr Ile Val Glu Asn Phe Gly Thr
        115                 120                 125

Tyr Asn Pro Ser Thr Gly Ala Thr Lys Leu Gly Glu Val Thr Ser Asp
    130                 135                 140

Gly Ser Val Tyr Asp Ile Tyr Arg Thr Gln Arg Val Asn Gln Pro Ser
145                 150                 155                 160

Ile Ile Gly Thr Ala Thr Phe Tyr Gln Tyr Trp Ser Val Arg Arg Asn
                165                 170                 175

His Arg Ser Ser Gly Ser Val Asn Thr Ala Asn His Phe Asn Ala Trp
            180                 185                 190

Ala Gln Gln Gly Leu Thr Leu Gly Thr Met Asp Tyr Gln Ile Val Ala
        195                 200                 205

Val Glu Gly Tyr Phe Ser Ser Gly Ser Ala Ser Ile Thr Val Ser
    210                 215                 220

<210> SEQ ID NO 37
<211> LENGTH: 1352
<212> TYPE: DNA
<213> ORGANISM: Trichoderma reesei
```

<400> SEQUENCE: 37

```
atgaaagcaa acgtcatctt gtgcctcctg gccccctgg tcgccgctct ccccaccgaa      60
accatccacc tcgaccccga gctcgccgct ctccgcgcca acctcaccga gcgaacagcc    120
gacctctggg accgccaagc tctcaaagc atcgaccagc tcatcaagag aaaaggcaag    180
ctctactttg gcaccgccac cgaccgcggc ctcctccaac gggaaaagaa cgcggccatc    240
atccaggcag acctcggcca ggtgacgccg agaacagca tgaagtggca gtcgctcgag    300
aacaaccaag gccagctgaa ctggggagac gccgactatc tcgtcaactt tgcccagcaa    360
aacggcaagt cgatacgcgg ccacactctg atctggcact cgcagctgcc tgcgtgggtg    420
aacaatatca caacgcgga tactctgcgg caagtcatcc gcacccatgt ctctactgtg    480
gttgggcggt acaagggcaa gattcgtgct tgggtgagtt ttgaacacca catgcccctt    540
ttcttagtcc gctcctcctc ctcttggaac ttctcacagt tatagccgta acaacattc    600
gacaggaaat ttaggatgac aactactgac tgacttgtgt gtgtgatggc gataggacgt    660
ggtcaatgaa atcttcaacg aggatggaac gctgcgctct tcagtcttt ccaggctcct    720
cggcgaggag tttgtctcga ttgccttcg tgctgctcga gatgctgacc cttctgcccg    780
tctttacatc aacgactaca atctcgaccg cgccaactat ggcaaggtca acgggttgaa    840
gacttacgtc tccaagtgga tctctcaagg agttcccatt gacggtattg gtgagccacg    900
accctaaat gtccccatt agagtctctt tctagagcca aggcttgaag ccattcaggg    960
actgacacga gagccttctc tacaggaagc cagtcccatc tcagcggcgg cggaggctct   1020
ggtacgctgg gtgcgctcca gcagctggca acggtacccg tcaccgagct ggccattacc   1080
gagctggaca ttcaggggc accgacgacg gattacaccc aagttgttca gcatgcctg    1140
agcgtctcca gtgcgtcgg catcaccgtg tggggcatca gtgacaaggt aagttgcttc    1200
ccctgtctgt gcttatcaac tgtaagcagc aacaactgat gctgtctgtc tttacctagg   1260
actcgtggcg tgccagcacc aaccctcttc tgtttgacgc aaacttcaac cccaagccgg   1320
catataacag cattgttggc atcttacaat ag                                 1352
```

<210> SEQ ID NO 38
<211> LENGTH: 347
<212> TYPE: PRT
<213> ORGANISM: Trichoderma reesei

<400> SEQUENCE: 38

```
Met Lys Ala Asn Val Ile Leu Cys Leu Leu Ala Pro Leu Val Ala Ala
1               5                   10                  15

Leu Pro Thr Glu Thr Ile His Leu Asp Pro Glu Leu Ala Ala Leu Arg
            20                  25                  30

Ala Asn Leu Thr Glu Arg Thr Ala Asp Leu Trp Asp Arg Gln Ala Ser
        35                  40                  45

Gln Ser Ile Asp Gln Leu Ile Lys Arg Lys Gly Lys Leu Tyr Phe Gly
    50                  55                  60

Thr Ala Thr Asp Arg Gly Leu Leu Gln Arg Glu Lys Asn Ala Ala Ile
65                  70                  75                  80

Ile Gln Ala Asp Leu Gly Gln Val Thr Pro Glu Asn Ser Met Lys Trp
                85                  90                  95

Gln Ser Leu Glu Asn Asn Gln Gly Gln Leu Asn Trp Gly Asp Ala Asp
            100                 105                 110

Tyr Leu Val Asn Phe Ala Gln Gln Asn Gly Lys Ser Ile Arg Gly His
        115                 120                 125
```

```
Thr Leu Ile Trp His Ser Gln Leu Pro Ala Trp Val Asn Asn Ile Asn
        130                 135                 140

Asn Ala Asp Thr Leu Arg Gln Val Ile Arg Thr His Val Ser Thr Val
145                 150                 155                 160

Val Gly Arg Tyr Lys Gly Lys Ile Arg Ala Trp Asp Val Val Asn Glu
                165                 170                 175

Ile Phe Asn Glu Asp Gly Thr Leu Arg Ser Ser Val Phe Ser Arg Leu
            180                 185                 190

Leu Gly Glu Glu Phe Val Ser Ile Ala Phe Arg Ala Ala Arg Asp Ala
        195                 200                 205

Asp Pro Ser Ala Arg Leu Tyr Ile Asn Asp Tyr Asn Leu Asp Arg Ala
    210                 215                 220

Asn Tyr Gly Lys Val Asn Gly Leu Lys Thr Tyr Val Ser Lys Trp Ile
225                 230                 235                 240

Ser Gln Gly Val Pro Ile Asp Gly Ile Gly Ser Gln Ser His Leu Ser
                245                 250                 255

Gly Gly Gly Gly Ser Gly Thr Leu Gly Ala Leu Gln Gln Leu Ala Thr
            260                 265                 270

Val Pro Val Thr Glu Leu Ala Ile Thr Glu Leu Asp Ile Gln Gly Ala
        275                 280                 285

Pro Thr Thr Asp Tyr Thr Gln Val Val Gln Ala Cys Leu Ser Val Ser
    290                 295                 300

Lys Cys Val Gly Ile Thr Val Trp Gly Ile Ser Asp Lys Asp Ser Trp
305                 310                 315                 320

Arg Ala Ser Thr Asn Pro Leu Leu Phe Asp Ala Asn Phe Asn Pro Lys
                325                 330                 335

Pro Ala Tyr Asn Ser Ile Val Gly Ile Leu Gln
            340                 345

<210> SEQ ID NO 39
<211> LENGTH: 2564
<212> TYPE: DNA
<213> ORGANISM: Trichoderma reesei

<400> SEQUENCE: 39
ggacagccgg acgcaatggt gaataacgca gctcttctcg ccgccctgtc ggctctcctg      60
cccacggccc tggcgcagaa caatcaaaca tacgccaact actctgctca gggccagcct    120
gatctctacc ccgagacact tgccacgctc acactctcgt tccccgactg cgaacatggc    180
cccctcaaga caatctcgt ctgtgactca tcggccggct atgtagagcg agcccaggcc    240
ctcatctcgc tcttcaccct cgaggagctc attctcaaca cgcaaaactc gggccccggc    300
gtgcctcgcc tggtcttcc gaactaccaa gtctggaatg aggctctgca cggcttggac    360
cgcgccaact cgccaccaa gggcggccag ttcgaatggg cgacctcgtt ccccatgccc    420
atcctcacta cggcggccct caaccgcaca ttgatccacc agattgccga catcatctcg    480
acccaagctc gagcattcag caacagcggc cgttacggtc tcgacgtcta tgcgccaaac    540
gtcaatggct tccgaagccc cctctggggc cgtggccagg agacgcccgg cgaagacgcc    600
tttttcctca gctccgccta tacttacgag tacatcacgg gcatccaggg tggcgtcgac    660
cctgagcacc tcaaggttgc cgccacggtg aagcactttg ccggatacga cctcgagaac    720
tggaacaacc agtccgtctc ggtttcgac gccatcataa ctcagcagga cctctccgaa    780
tactacactc cccagttcct cgctgcggcc cgttatgcaa agtcacgcag cttgatgtgc    840
```

```
gcatacaact ccgtcaacgg cgtgcccagc tgtgccaaca gcttcttcct gcagacgctt    900
ttgcgcgaga gctggggctt ccccgaatgg ggatacgtct cgtccgattg cgatgccgtc    960
tacaacgttt tcaaccctca tgactacgcc agcaaccagt cgtcagccgc cgccagctca   1020
ctgcgagccg gcaccgatat cgactgcggt cagacttacc cgtggcacct caacgagtcc   1080
tttgtggccg gcgaagtctc ccgcggcgag atcgagcggt ccgtcacccg tctgtacgcc   1140
aacctcgtcc gtctcggata cttcgacaag aagaaccagt accgctcgct cggttggaag   1200
gatgtcgtca agactgatgc ctggaacatc tcgtacgagg ctgctgttga gggcatcgtc   1260
ctgctcaaga cgatggcac tctccctctg tccaagaagg tgcgcagcat tgctctgatc   1320
ggaccatggg ccaatgccac aacccaaatg caaggcaact actatggccc tgccccatac   1380
ctcatcagcc ctctggaagc tgctaagaag gccggctatc acgtcaactt tgaactcggc   1440
acagagatcg ccggcaacag caccactggc tttgccaagg ccattgctgc cgccaagaag   1500
tcggatgcca tcatctacct cggtggaatt gacaacacca ttgaacagga gggcgctgac   1560
cgcacggaca ttgcttggcc cggtaatcag ctggatctca tcaagcagct cagcgaggtc   1620
ggcaaacccc ttgtcgtcct gcaaatgggc ggtggtcagg tagactcatc ctcgctcaag   1680
agcaacaaga aggtcaactc cctcgtctgg ggcggatatc ccggccagtc gggaggcgtt   1740
gccctcttcg acattctctc tggcaagcgt gctcctgccg ccgactggt caccactcag   1800
tacccggctg agtatgttca ccaattcccc cagaatgaca tgaacctccg acccgatgga   1860
aagtcaaacc ctggacagac ttacatctgg tacaccggca aacccgtcta cgagtttggc   1920
agtggtctct tctacaccac cttcaaggag actctcgcca ccacccaa gagcctcaag   1980
ttcaacacct catcgatcct ctctgctcct caccccggat acacttacag cgagcagatt   2040
cccgtcttca ccttcgaggc caacatcaag aactcgggca agacggagtc cccatatacg   2100
gccatgctgt ttgttcgcac aagcaacgct ggcccagccc cgtacccgaa caagtggctc   2160
gtcggattcg accgacttgc cgacatcaag cctggtcact cttccaagct cagcatcccc   2220
atccctgtca gtgctctcgc ccgtgttgat tctcacggaa accggattgt ataccccggc   2280
aagtatgagc tagccttgaa caccgacgag tctgtgaagc ttgagtttga gttggtggga   2340
gaagaggtaa cgattgagaa ctggccgttg gaggagcaac agatcaagga tgctacacct   2400
gacgcataag ggttttaatg atgttgttat gacaaacggg tagagtagtt aatgatggaa   2460
taggaagagg ccatagtttt ctgtttgcaa accatttttg ccattgcgaa aaaaaaaaa   2520
aaaaaaaaaa aaaaaaaaaa aaaaaaaaaa aaaaaaaaaa aaaa                    2564

<210> SEQ ID NO 40
<211> LENGTH: 780
<212> TYPE: PRT
<213> ORGANISM: Trichoderma reesei

<400> SEQUENCE: 40

Met Val Asn Asn Ala Ala Leu Leu Ala Ala Leu Ser Ala Leu Leu Pro
1               5                   10                  15

Thr Leu Ala Gln Asn Asn Gln Thr Tyr Ala Asn Tyr Ser Ala Gln
            20                  25                  30

Gly Gln Pro Asp Leu Tyr Pro Glu Thr Leu Ala Thr Leu Thr Leu Ser
        35                  40                  45

Phe Pro Asp Cys Glu His Gly Pro Leu Lys Asn Asn Leu Val Cys Asp
    50                  55                  60

Ser Ser Ala Gly Tyr Val Glu Arg Ala Gln Ala Leu Ile Ser Leu Phe
```

-continued

```
                65                  70                  75                  80
            Thr Leu Glu Glu Leu Ile Leu Asn Thr Gln Asn Ser Gly Pro Gly Val
                            85                  90                  95
            Pro Arg Leu Gly Leu Pro Asn Tyr Gln Val Trp Asn Glu Ala Leu His
                            100                 105                 110
            Gly Leu Asp Arg Ala Asn Phe Ala Thr Lys Gly Gly Gln Phe Glu Trp
                            115                 120                 125
            Ala Thr Ser Phe Pro Met Pro Ile Leu Thr Thr Ala Ala Leu Asn Arg
                            130                 135                 140
            Thr Leu Ile His Gln Ile Ala Asp Ile Ile Ser Thr Gln Ala Arg Ala
            145                 150                 155                 160
            Phe Ser Asn Ser Gly Arg Tyr Gly Leu Asp Val Tyr Ala Pro Asn Val
                            165                 170                 175
            Asn Gly Phe Arg Ser Pro Leu Trp Gly Arg Gly Gln Glu Thr Pro Gly
                            180                 185                 190
            Glu Asp Ala Phe Phe Leu Ser Ser Ala Tyr Thr Tyr Glu Tyr Ile Thr
                            195                 200                 205
            Gly Ile Gln Gly Gly Val Asp Pro Glu His Leu Lys Val Ala Ala Thr
                            210                 215                 220
            Val Lys His Phe Ala Gly Tyr Asp Leu Glu Asn Trp Asn Asn Gln Ser
            225                 230                 235                 240
            Arg Leu Gly Phe Asp Ala Ile Ile Thr Gln Gln Asp Leu Ser Glu Tyr
                            245                 250                 255
            Tyr Thr Pro Gln Phe Leu Ala Ala Ala Arg Tyr Ala Lys Ser Arg Ser
                            260                 265                 270
            Leu Met Cys Ala Tyr Asn Ser Val Asn Gly Val Pro Ser Cys Ala Asn
                            275                 280                 285
            Ser Phe Phe Leu Gln Thr Leu Leu Arg Glu Ser Trp Gly Phe Pro Glu
                            290                 295                 300
            Trp Gly Tyr Val Ser Ser Asp Cys Asp Ala Val Tyr Asn Val Phe Asn
            305                 310                 315                 320
            Pro His Asp Tyr Ala Ser Asn Gln Ser Ser Ala Ala Ser Ser Leu
                            325                 330                 335
            Arg Ala Gly Thr Asp Ile Asp Cys Gly Gln Thr Tyr Pro Trp His Leu
                            340                 345                 350
            Asn Glu Ser Phe Val Ala Gly Glu Val Ser Arg Gly Glu Ile Glu Arg
                            355                 360                 365
            Ser Val Thr Arg Leu Tyr Ala Asn Leu Val Arg Leu Gly Tyr Phe Asp
                            370                 375                 380
            Lys Lys Asn Gln Tyr Arg Ser Leu Gly Trp Lys Asp Val Val Lys Thr
            385                 390                 395                 400
            Asp Ala Trp Asn Ile Ser Tyr Glu Ala Ala Val Glu Gly Ile Val Leu
                            405                 410                 415
            Leu Lys Asn Asp Gly Thr Leu Pro Leu Ser Lys Lys Val Arg Ser Ile
                            420                 425                 430
            Ala Leu Ile Gly Pro Trp Ala Asn Ala Thr Thr Gln Met Gln Gly Asn
                            435                 440                 445
            Tyr Tyr Gly Pro Ala Pro Tyr Leu Ile Ser Pro Leu Glu Ala Ala Lys
                            450                 455                 460
            Lys Ala Gly Tyr His Val Asn Phe Glu Leu Gly Thr Glu Ile Ala Gly
            465                 470                 475                 480
            Asn Ser Thr Thr Gly Phe Ala Lys Ala Ile Ala Ala Lys Lys Ser
                            485                 490                 495
```

```
Asp Ala Ile Ile Tyr Leu Gly Gly Ile Asp Asn Thr Ile Glu Gln Glu
            500                 505                 510

Gly Ala Asp Arg Thr Asp Ile Ala Trp Pro Gly Asn Gln Leu Asp Leu
        515                 520                 525

Ile Lys Gln Leu Ser Glu Val Gly Lys Pro Leu Val Val Leu Gln Met
    530                 535                 540

Gly Gly Gly Gln Val Asp Ser Ser Ser Leu Lys Ser Asn Lys Lys Val
545                 550                 555                 560

Asn Ser Leu Val Trp Gly Gly Tyr Pro Gly Gln Ser Gly Gly Val Ala
                565                 570                 575

Leu Phe Asp Ile Leu Ser Gly Lys Arg Ala Pro Ala Gly Arg Leu Val
            580                 585                 590

Thr Thr Gln Tyr Pro Ala Glu Tyr Val His Gln Phe Pro Gln Asn Asp
        595                 600                 605

Met Asn Leu Arg Pro Asp Gly Lys Ser Asn Pro Gly Gln Thr Tyr Ile
    610                 615                 620

Trp Tyr Thr Gly Lys Pro Val Tyr Glu Phe Gly Ser Gly Leu Phe Tyr
625                 630                 635                 640

Thr Thr Phe Lys Glu Thr Leu Ala Ser His Pro Lys Ser Leu Lys Phe
                645                 650                 655

Asn Thr Ser Ser Ile Leu Ser Ala Pro His Pro Gly Tyr Thr Tyr Ser
            660                 665                 670

Glu Gln Ile Pro Val Phe Thr Phe Glu Ala Asn Ile Lys Asn Ser Gly
        675                 680                 685

Lys Thr Glu Ser Pro Tyr Thr Ala Met Leu Phe Val Arg Thr Ser Asn
    690                 695                 700

Ala Gly Pro Ala Pro Tyr Pro Asn Lys Trp Leu Val Gly Phe Asp Arg
705                 710                 715                 720

Leu Ala Asp Ile Lys Pro Gly His Ser Ser Lys Leu Ser Ile Pro Ile
                725                 730                 735

Pro Val Ser Ala Leu Ala Arg Val Asp Ser His Gly Asn Arg Ile Val
            740                 745                 750

Tyr Pro Gly Lys Tyr Glu Leu Ala Leu Asn Thr Asp Glu Ser Val Lys
        755                 760                 765

Leu Glu Phe Glu Leu Val Gly Glu Glu Val Thr Ile
    770                 775                 780

<210> SEQ ID NO 41
<211> LENGTH: 2779
<212> TYPE: DNA
<213> ORGANISM: Trichoderma reesei

<400> SEQUENCE: 41
atgtccgcgt ctagtgattt atatgtagaa tgatcacaat tcatgtaact gcgttttcgc      60
acatgcaaaa agccctaacg tgagactgag ccacttccta gttttcgtat catgtcagtt     120
gcaaggttac accacaatgc agctcaacga dacaacgctg ccagcccata taatggata      180 gctggttgta gagagattaa gaagagaatg ctgtttcaga aggaagacta tcatagca      240 gctgctacat ttccctcttt ccctctttcc atcccttaat agatacgtac ccttgcaatt     300
ggccgtttcg gaagagcttt tctgcttatc ctaaccacct acgccagaat accggtggaa     360
taatcagtgc tcaataggga aacccccaac tgcagcatat aagcctatta acaagacgtc     420
ccaacatgca ttttccttca gtccgcagca ggctatagag agtaggcaat ttacacacca     480
```

```
cttttagcct ctgcacatat ctcaccacat ttgcattacg gcatccacta ttacaaccac    540
ttggcacctg atggctttgc tctacccata tcggttttta cgttccgctg tgttcagtcg    600
ttaaatccgt ggtggagcag aacgaccagc ttctcgtatc gggaactccg cttatccgat    660
accctcagtc gaacccttcg tgatactcag cctaaataac atcgcatcgt agcagacaac    720
ttcagtaatt tttgtggggt aatggtcaga tcgctcctct tatatataaa gcagaggtta    780
gtgggctaag gaaattcgtg gttcgcttat agtagagctg tcagttgccc ttcccgaact    840
gttagacggg atggctggta agcttatcct cgtggctcta gcaagccttg tatcactctc    900
tattcagcag aattgcgcag cattattgta agagtgttga gcgtgttgag taccatctgt    960
atcgttgcta acgtaggctt ttagtggcca atgtggaggc atagggtggt ccggcaccac   1020
atgttgcgtt gctggcgccc agtgcagttt tgtcaatgac tggtactccc agtgccttgc   1080
gtcaaccgta tgagctccga tccgggccgt caatatcttc taactccaga ctgtacaggg   1140
cggaaacccc ccaaacggaa caacttcctc tagcttggtt tcacggacgt cgtcagcatc   1200
ctcatccgtc ggctcgtctt cacccggcgg caactcacca actggcagtg cttccaccta   1260
cacaaccaca gatacagcta ccgtggctcc tcattcgcag tctccttacc ccagcattgc   1320
cgcatccagt tgcggatcgt ggaccctcgt ggataatgtt tgctgcccat catattgtgc   1380
taatgatgac acatccgagt catgctcagg ctgcggtacc tgcactacgc cgccctcggc   1440
ggactgcaaa tccggaacca tgtatccaga ggtccatcac gtatccagca acgagagctg   1500
gcactacagt gtaagatgac caacgctggg gtatctaatc ctttgtcttc ctcggcgtgc   1560
tgaccttgga gcatttagag atcaacccac tttggcctaa cgagcggcgg ggcctgtggc   1620
tttggcctgt acggtctctg cacaaagggc agtgttacag ccagctggac ggatcccatg   1680
cttggcgcga cgtgtgacgc ttttttgtaca gcgtatcccc tgcttttgcaa agaccctacc   1740 ggcactaccc ttcgtggcaa cttcgcagct ccaaacggcg attactacac ccaagttggg   1800
gaccccgaga ggcaatcatt ttctggtgta gtattcactg acagtgcgat agttctggtc   1860
ctcgttgcca ggagccctcg ataactacct gtcctgcggc gagtgcattg agctgataca   1920
aacaaagccc gatgggaccg attatgctgt cggagaagcc ggctacacgg atccaattac   1980
tctcgagatt gtggacagct gcccgtgcag cgcgaactcc aagtggtgct gtcagagagc   2040
cccgtccatc ccgtccattg tactacatgc gccaaccgaa tggccctggc taacatctcg   2100
caggtggtcc gggcgccgat cattgcggag agatcgactt caaatacggc tgtcctcttc   2160
ctgctgacag cattcatctc gacctgtcag acattgccat gggccgtttg cagggcaatg   2220
gatcactaac caatggcgtc atcccgactc gatatagaag agtccaatgc cccaaagttg   2280
ggaacgccta catttggctt cgaaatggcg gagggcctta ctattttgct ctcacggcag   2340
tcaacaccaa cggaccgggc tcagtcacca aaatcgagat caagggcgca gacaccgaca   2400
actgggttgc cttggtccat gacccaaact atacgagtag ccgccacaa gaacgctatg    2460 gcagttgggt aatcccacag ggatcagggc cctttaactt gcctgttgga attcgtctga   2520
ctagcccaac gggggaacag attgtgaatg aacaggccat caagacattc actcctccgg   2580
ccacaggtga ccccaatttt tactacattg acattggtgt gcagtttagc cagaattgat   2640
ggcaagcatt gggcaatggg cttcttgctg tgggacaatg atgtaggcta gattctcaat   2700
gcttcaagta tgtggtgtac gtcttcgtgt gtatagatag gtatgctgtt cacttaaata   2760
cacatccttt ggtacgttg                                                2779
```

```
<210> SEQ ID NO 42
<211> LENGTH: 493
<212> TYPE: PRT
<213> ORGANISM: Trichoderma reesei

<400> SEQUENCE: 42
```

| | | | | | | | | | | | | | | | |
|---|---|---|---|---|---|---|---|---|---|---|---|---|---|---|---|
| Met | Ala | Gly | Lys | Leu | Ile | Leu | Val | Ala | Leu | Ala | Ser | Leu | Val | Ser | Leu |
| 1 | | | | 5 | | | | | 10 | | | | | 15 | |
| Ser | Ile | Gln | Gln | Asn | Cys | Ala | Ala | Leu | Phe | Gly | Gln | Cys | Gly | Gly | Ile |
| | | | 20 | | | | | 25 | | | | | 30 | | |
| Gly | Trp | Ser | Gly | Thr | Thr | Cys | Cys | Val | Ala | Gly | Ala | Gln | Cys | Ser | Phe |
| | | | 35 | | | | | 40 | | | | | 45 | | |
| Val | Asn | Asp | Trp | Tyr | Ser | Gln | Cys | Leu | Ala | Ser | Thr | Gly | Gly | Asn | Pro |
| | 50 | | | | | 55 | | | | | 60 | | | | |
| Pro | Asn | Gly | Thr | Thr | Ser | Ser | Ser | Leu | Val | Ser | Arg | Thr | Ser | Ser | Ala |
| 65 | | | | | 70 | | | | | 75 | | | | | 80 |
| Ser | Ser | Ser | Val | Gly | Ser | Ser | Pro | Gly | Gly | Asn | Ser | Pro | Thr | Gly | |
| | | | | 85 | | | | | 90 | | | | | 95 | |
| Ser | Ala | Ser | Thr | Tyr | Thr | Thr | Thr | Asp | Thr | Ala | Thr | Val | Ala | Pro | His |
| | | | 100 | | | | | 105 | | | | | 110 | | |
| Ser | Gln | Ser | Pro | Tyr | Pro | Ser | Ile | Ala | Ala | Ser | Ser | Cys | Gly | Ser | Trp |
| | | | 115 | | | | | 120 | | | | | 125 | | |
| Thr | Leu | Val | Asp | Asn | Val | Cys | Cys | Pro | Ser | Tyr | Cys | Ala | Asn | Asp | Asp |
| | 130 | | | | | 135 | | | | | 140 | | | | |
| Thr | Ser | Glu | Ser | Cys | Ser | Gly | Cys | Gly | Thr | Cys | Thr | Thr | Pro | Pro | Ser |
| 145 | | | | | 150 | | | | | 155 | | | | | 160 |
| Ala | Asp | Cys | Lys | Ser | Gly | Thr | Met | Tyr | Pro | Glu | Val | His | His | Val | Ser |
| | | | | 165 | | | | | 170 | | | | | 175 | |
| Ser | Asn | Glu | Ser | Trp | His | Tyr | Ser | Arg | Ser | Thr | His | Phe | Gly | Leu | Thr |
| | | | 180 | | | | | 185 | | | | | 190 | | |
| Ser | Gly | Gly | Ala | Cys | Gly | Phe | Gly | Leu | Tyr | Gly | Leu | Cys | Thr | Lys | Gly |
| | | | 195 | | | | | 200 | | | | | 205 | | |
| Ser | Val | Thr | Ala | Ser | Trp | Thr | Asp | Pro | Met | Leu | Gly | Ala | Thr | Cys | Asp |
| | 210 | | | | | 215 | | | | | 220 | | | | |
| Ala | Phe | Cys | Thr | Ala | Tyr | Pro | Leu | Leu | Cys | Lys | Asp | Pro | Thr | Gly | Thr |
| 225 | | | | | 230 | | | | | 235 | | | | | 240 |
| Thr | Leu | Arg | Gly | Asn | Phe | Ala | Ala | Pro | Asn | Gly | Asp | Tyr | Tyr | Thr | Gln |
| | | | | 245 | | | | | 250 | | | | | 255 | |
| Phe | Trp | Ser | Ser | Leu | Pro | Gly | Ala | Leu | Asp | Asn | Tyr | Leu | Ser | Cys | Gly |
| | | | 260 | | | | | 265 | | | | | 270 | | |
| Glu | Cys | Ile | Glu | Leu | Ile | Gln | Thr | Lys | Pro | Asp | Gly | Thr | Asp | Tyr | Ala |
| | | | 275 | | | | | 280 | | | | | 285 | | |
| Val | Gly | Glu | Ala | Gly | Tyr | Thr | Asp | Pro | Ile | Thr | Leu | Glu | Ile | Val | Asp |
| | 290 | | | | | 295 | | | | | 300 | | | | |
| Ser | Cys | Pro | Cys | Ser | Ala | Asn | Ser | Lys | Trp | Cys | Cys | Gly | Pro | Gly | Ala |
| 305 | | | | | 310 | | | | | 315 | | | | | 320 |
| Asp | His | Cys | Gly | Glu | Ile | Asp | Phe | Lys | Tyr | Gly | Cys | Pro | Leu | Pro | Ala |
| | | | | 325 | | | | | 330 | | | | | 335 | |
| Asp | Ser | Ile | His | Leu | Asp | Leu | Ser | Asp | Ile | Ala | Met | Gly | Arg | Leu | Gln |
| | | | 340 | | | | | 345 | | | | | 350 | | |
| Gly | Asn | Gly | Ser | Leu | Thr | Asn | Gly | Val | Ile | Pro | Thr | Arg | Tyr | Arg | Arg |
| | | | 355 | | | | | 360 | | | | | 365 | | |
| Val | Gln | Cys | Pro | Lys | Val | Gly | Asn | Ala | Tyr | Ile | Trp | Leu | Arg | Asn | Gly |
| | 370 | | | | | 375 | | | | | 380 | | | | |

-continued

```
Gly Gly Pro Tyr Tyr Phe Ala Leu Thr Ala Val Asn Thr Asn Gly Pro
385                 390                 395                 400

Gly Ser Val Thr Lys Ile Glu Ile Lys Gly Ala Asp Thr Asp Asn Trp
            405                 410                 415

Val Ala Leu Val His Asp Pro Asn Tyr Thr Ser Ser Arg Pro Gln Glu
        420                 425                 430

Arg Tyr Gly Ser Trp Val Ile Pro Gln Gly Ser Gly Pro Phe Asn Leu
    435                 440                 445

Pro Val Gly Ile Arg Leu Thr Ser Pro Thr Gly Glu Gln Ile Val Asn
450                 455                 460

Glu Gln Ala Ile Lys Thr Phe Thr Pro Pro Ala Thr Gly Asp Pro Asn
465                 470                 475                 480

Phe Tyr Tyr Ile Asp Ile Gly Val Gln Phe Ser Gln Asn
                485                 490
```

<210> SEQ ID NO 43
<211> LENGTH: 40
<212> TYPE: DNA
<213> ORGANISM: Aspergillus fumigatus

<400> SEQUENCE: 43
cgcggactgc gcaccatgct ggcctccacc ttctcctacc                              40

<210> SEQ ID NO 44
<211> LENGTH: 48
<212> TYPE: DNA
<213> ORGANISM: Aspergillus fumigatus

<400> SEQUENCE: 44
ctttcgccac ggagcttaat taactacagg cactgagagt aataatca                    48

<210> SEQ ID NO 45
<211> LENGTH: 1131
<212> TYPE: DNA
<213> ORGANISM: Herpes simplex virus

<400> SEQUENCE: 45
atggcttcgt accccggcca tcaacacgcg tctgcgttcg accaggctgc gcgttctcgc       60
ggccatagca accgacgtac ggcgttgcgc cctcgccggc agcaagaagc cacggaagtc      120
cgcccggagc agaaaatgcc cacgctactg cgggtttata tagacggtcc ccacgggatg      180
gggaaaacca ccaccacgca actgctggtg gccctgggtt cgcgcgacga tatcgtctac      240
gtacccgagc gatgactta ctggcgggtg ctgggggctt ccgagacaat cgcgaacatc       300
tacaccacac aacaccgcct cgaccagggt gagatatcgg ccggggacgc ggcggtggta      360
atgacaagcg cccagataac aatgggcatg cctatgccg tgaccgacgc cgttctggct       420
cctcatatcg ggggggaggc tgggagctca catgccccgc cccggccct caccctcatc       480 ttcgaccgcc atcccatcgc cgccctcctg tgctacccgg ccgcgcggta ccttatgggc      540
agcatgaccc cccaggccgt gctggcgttc gtggccctca tcccgccgac cttgccggc      600 accaacatcg tgcttggggc ccttccggag gacagacaca tcgaccgcct ggccaaacgc      660
cagcgccccg cgagcggct ggacctggct atgctggctg cgattcgccg cgtttacggg      720
ctacttgcca atacggtgcg gtatctgcag tgcggcgggt cgtggcggga ggactgggga      780
cagctttcgg ggacgccgt gccgcccag ggtgccgagc ccagagcaa cgcgggccca         840 cgaccccata tcggggacac gttatttacc ctgtttcggg ccccgagtt gctggccccc      900
```

```
aacggcgacc tgtataacgt gtttgcctgg gccttggacg tcttggccaa acgcctccgt    960
tccatgcacg tctttatcct ggattacgac caatcgcccg ccggctgccg ggacgccctg   1020
ctgcaactta cctccgggat ggtccagacc cacgtcacca cccccggctc cataccgacg   1080
atatgcgacc tggcgcgcac gtttgcccgg gagatggggg aggctaactg a            1131
```

<210> SEQ ID NO 46
<211> LENGTH: 376
<212> TYPE: PRT
<213> ORGANISM: Herpes simplex virus

<400> SEQUENCE: 46

```
Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Pro Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Arg Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Gly Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335
```

```
Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375

<210> SEQ ID NO 47
<211> LENGTH: 43
<212> TYPE: DNA
<213> ORGANISM: Trichoderma reesei

<400> SEQUENCE: 47
ttagactgcg gccgcgtggc gaaagcctga cgcaccggta gat            43

<210> SEQ ID NO 48
<211> LENGTH: 41
<212> TYPE: DNA
<213> ORGANISM: Trichoderma reesei

<400> SEQUENCE: 48
agtagttagc ggccgcacgg cacggttaag cagggtcttg c              41

<210> SEQ ID NO 49
<211> LENGTH: 25
<212> TYPE: DNA
<213> ORGANISM: Trichoderma reesei

<400> SEQUENCE: 49
aaaaaacaaa catcccgttc ataac                                25

<210> SEQ ID NO 50
<211> LENGTH: 25
<212> TYPE: DNA
<213> ORGANISM: Trichoderma reesei

<400> SEQUENCE: 50
aacaaggttt accggtttcg aaaag                                25

<210> SEQ ID NO 51
<211> LENGTH: 54
<212> TYPE: DNA
<213> ORGANISM: Trichoderma reesei

<400> SEQUENCE: 51
acgaattgtt taaacgtcga cccaagtatc cagaggtgta tggaaatatc agat  54

<210> SEQ ID NO 52
<211> LENGTH: 44
<212> TYPE: DNA
<213> ORGANISM: Trichoderma reesei

<400> SEQUENCE: 52
cgcgtagatc tgcggccatg gtgcaataca cagagggtga tctt           44

<210> SEQ ID NO 53
<211> LENGTH: 48
<212> TYPE: DNA
<213> ORGANISM: Trichoderma reesei

<400> SEQUENCE: 53
atctacgcgt actagttaat taaggctttc gtgaccgggc ttcaaaca       48
```

<210> SEQ ID NO 54
<211> LENGTH: 46
<212> TYPE: DNA
<213> ORGANISM: Trichoderma reesei

<400> SEQUENCE: 54
gcggccgtta ctagtggatc cactcggagt tgttatacgc tactcg            46

<210> SEQ ID NO 55
<211> LENGTH: 46
<212> TYPE: DNA
<213> ORGANISM: Trichoderma reesei

<400> SEQUENCE: 55
atccatcaca ctggcggccg cgcttcaaac aatgatgtgc gatggt            46

<210> SEQ ID NO 56
<211> LENGTH: 46
<212> TYPE: DNA
<213> ORGANISM: Trichoderma reesei

<400> SEQUENCE: 56
gatgcatgct cgagcggccg cctaccttgg cagccctacg agagag            46

<210> SEQ ID NO 57
<211> LENGTH: 41
<212> TYPE: DNA
<213> ORGANISM: Aspergillus fumigatus

<400> SEQUENCE: 57
ctctgtgtat tgcaccatga agcaccttgc atcttccatc g                 41

<210> SEQ ID NO 58
<211> LENGTH: 40
<212> TYPE: DNA
<213> ORGANISM: Aspergillus fumigatus

<400> SEQUENCE: 58
ccggtcacga aagccttaat taaaaggacg ggttagcgtt                   40

<210> SEQ ID NO 59
<211> LENGTH: 25
<212> TYPE: DNA
<213> ORGANISM: Aspergillus fumigatus

<400> SEQUENCE: 59
agccacatgc cgcatattga caaag                                   25

<210> SEQ ID NO 60
<211> LENGTH: 25
<212> TYPE: DNA
<213> ORGANISM: Aspergillus fumigatus

<400> SEQUENCE: 60
agggattcag tgtgctacag gctgc                                   25

<210> SEQ ID NO 61
<211> LENGTH: 25
<212> TYPE: DNA
<213> ORGANISM: Aspergillus fumigatus

<400> SEQUENCE: 61
aaaaaacaaa catcccgttc ataac                                   25

<210> SEQ ID NO 62
<211> LENGTH: 25
<212> TYPE: DNA
<213> ORGANISM: Aspergillus fumigatus

<400> SEQUENCE: 62
aacaaggttt accggtttcg aaaag                                              25

<210> SEQ ID NO 63
<211> LENGTH: 27
<212> TYPE: DNA
<213> ORGANISM: Aspergillus fumigatus

<400> SEQUENCE: 63
gttaagcata caattgaacg agaatgg                                            27

<210> SEQ ID NO 64
<211> LENGTH: 25
<212> TYPE: DNA
<213> ORGANISM: Aspergillus fumigatus

<400> SEQUENCE: 64
gatgatataa tggagcaaat aaggg                                              25

<210> SEQ ID NO 65
<211> LENGTH: 2077
<212> TYPE: DNA
<213> ORGANISM: Trichoderma reesei

<400> SEQUENCE: 65
atgacggatg cacaaaagaa ttggaggaga gacgaaaacg acgaggacga tgaagcagag        60
caggagctcg atgaggctgt aagtcgccgc gagtcgcatc tggtctgaca agcgtcgtct       120
gacactcttt tctcccatct agagcctcaa ggcgcagaaa gatgcaattc ttctagccat       180
tgaagtcagt ccgtcgatgc ttgagcctcc gccagtctcc agctctagga aagctgatcg       240
ggacagcccc gttcaagctg cgctgaaatg cgcccgccac ctgatggagc agcgcatcat       300
ctccaacccc aaagacatga tgggaatcct cctctttggg acagaaaaga ccaagttccg       360
ggacgacaat ggccgcagtg ggctcgggta tccgaattgc tacctctttta tggacctcga       420
cattccggca gctgaagacg tcaaagcgtt gaaggcgctg accgaggacg aagacgaaga       480
cgaagtgctg aagcccgcca ccaccgacac agtttccatg tccaacgtgt tgttttgcgc       540
caaccagata ttcaccacaa aggcggccaa ctttggcagc cggcgacttt tcattgtgac       600
ggacaatgac gatccgcacg cgtcggacaa ggcggcgagg tctgctgccg ctgttcgggc       660
aaaggacttg tacgatctgg gcatcacgat cgacttgttt ccaatcacca caggagactc       720
caagtttgat ctcagcaaat tttacgatgt aagctatatt tcttcgtttc ttcgctctaa       780
aatcacccac cctccgtcgt gacatagact gacaaggaac taggatattg tctatcgcga       840
cccgaatgcc gaggccaatc gcaccgaagt gcgagcctca aaatcgggcg atggactgtc       900
tcttctcaac tcgctcattt caaacatcaa ttccaagcag acgcccaagc gagcattgtt       960
ccatctgcca tttgagattg cacctggact caagatcact gtcaagggct acaacattgt      1020
gcatcggcaa acgccggcga gaacgtgcta catctggctg aaggggaga aggctcagat       1080
tgcaacaggc gaaacgacgc gagttgcaga ggattctgcc agaacagtcg aaaagcaaga      1140
gataaaaaag gcctacaagt ttggtggcga atacgtatac tttacgcccg aggagcagaa      1200

```
gaagctccgg gattttggcg cgcccacgat ccggatcatt ggattcaaga agcgcagcat   1260
gattcccgtc tgggccagcg tcaagaagtc gacctttatc tttcccagcg aagaggatta   1320
catcggatcg acacgcgtct tttcagccct atggcagaag cttctaaagg atgacaagat   1380
cggcctcgct tggtgcgtgc ttcgatctaa cgcgcagccc atgtttgccg ctctgattcc   1440
atcaagagag cagtccgaag acgacgcggg gacaccatat ctaccagctg gcctgtggct   1500
gtatcctctc cctacggctg acgacctgcg agatataaat gtcgaacgaa agctcgactg   1560
ctcggaggac ctaaaaacca aaatgagagt cattgtacaa cagctcaatc tccccaaggg   1620
catatataac ccactcaagt acccgaaccc ggctctgcaa tggcactaca agatcctcca   1680
gaccctcgcc ttggaggagg agatgccgga agaacccgaa gacttgacgg agcccaaaaa   1740
caaggcgata agcaaacgcg tcggaggtta cttggaggag tggtccgaga ctctgaaaga   1800
cgaggcggac agggccactc gatccaggtc cttgaagcga gagattgaag atgatgcccc   1860
ggagcgcccc gcaaagcaga gaaaggtagc tggagagcgg cccagcggat cgaatcttag   1920
catggcgcag cttagggatg ccattgagag cgggagcatc tcgaagatga cagtggcaca   1980
gctgaaggat gtcgctggcg ccagaggact cagcacgggt ggtaagaagg ctgatttgct   2040
ggagcggata gagcagtggg ttgaggagaa cagctga                            2077
```

<210> SEQ ID NO 66
<211> LENGTH: 649
<212> TYPE: PRT
<213> ORGANISM: Trichoderma reesei

<400> SEQUENCE: 66

```
Met Thr Asp Ala Gln Lys Asn Trp Arg Arg Asp Glu Asn Asp Glu Asp
1               5                   10                  15

Asp Glu Ala Glu Gln Glu Leu Asp Glu Ala Val Ser Arg Arg Asp Leu
            20                  25                  30

Lys Ala Gln Lys Asp Ala Ile Leu Leu Ala Ile Glu Val Ser Pro Ser
        35                  40                  45

Met Leu Glu Pro Pro Val Ser Ser Ser Arg Lys Ala Asp Arg Asp
    50                  55                  60

Ser Pro Val Gln Ala Ala Leu Lys Cys Ala Arg His Leu Met Glu Gln
65                  70                  75                  80

Arg Ile Ile Ser Asn Pro Lys Asp Met Met Gly Ile Leu Leu Phe Gly
                85                  90                  95

Thr Glu Lys Thr Lys Phe Arg Asp Asp Asn Gly Arg Ser Gly Leu Gly
            100                 105                 110

Tyr Pro Asn Cys Tyr Leu Phe Met Asp Leu Asp Ile Pro Ala Ala Glu
        115                 120                 125

Asp Val Lys Ala Leu Lys Ala Leu Thr Glu Asp Glu Asp Glu
    130                 135                 140

Val Leu Lys Pro Ala Thr Thr Asp Thr Val Ser Met Ser Asn Val Leu
145                 150                 155                 160

Phe Cys Ala Asn Gln Ile Phe Thr Thr Lys Ala Asn Phe Gly Ser
                165                 170                 175

Arg Arg Leu Phe Ile Val Thr Asp Asn Asp Pro His Ala Ser Asp
            180                 185                 190

Lys Ala Ala Arg Ser Ala Ala Ala Val Arg Ala Lys Asp Leu Tyr Asp
        195                 200                 205
```

```
Leu Gly Ile Thr Ile Asp Leu Phe Pro Ile Thr Thr Gly Asp Ser Lys
            210                 215                 220

Phe Asp Leu Ser Lys Phe Tyr Asp Asp Ile Val Tyr Arg Asp Pro Asn
225                 230                 235                 240

Ala Glu Ala Asn Arg Thr Glu Val Arg Ala Ser Lys Ser Gly Asp Gly
                245                 250                 255

Leu Ser Leu Leu Asn Ser Leu Ile Ser Asn Ile Asn Ser Lys Gln Thr
            260                 265                 270

Pro Lys Arg Ala Leu Phe His Leu Pro Phe Glu Ile Ala Pro Gly Leu
            275                 280                 285

Lys Ile Thr Val Lys Gly Tyr Asn Ile Val His Arg Gln Thr Pro Ala
290                 295                 300

Arg Thr Cys Tyr Ile Trp Leu Glu Gly Glu Lys Ala Gln Ile Ala Thr
305                 310                 315                 320

Gly Glu Thr Thr Arg Val Ala Glu Asp Ser Ala Arg Thr Val Glu Lys
                325                 330                 335

Gln Glu Ile Lys Lys Ala Tyr Lys Phe Gly Gly Glu Tyr Val Tyr Phe
            340                 345                 350

Thr Pro Glu Glu Gln Lys Lys Leu Arg Asp Phe Gly Ala Pro Thr Ile
            355                 360                 365

Arg Ile Ile Gly Phe Lys Lys Arg Ser Met Ile Pro Val Trp Ala Ser
370                 375                 380

Val Lys Lys Ser Thr Phe Ile Phe Pro Ser Glu Asp Tyr Ile Gly
385                 390                 395                 400

Ser Thr Arg Val Phe Ser Ala Leu Trp Gln Lys Leu Leu Lys Asp Asp
                405                 410                 415

Lys Ile Gly Leu Ala Trp Cys Val Leu Arg Ser Asn Ala Gln Pro Met
            420                 425                 430

Phe Ala Ala Leu Ile Pro Ser Arg Glu Gln Ser Glu Asp Asp Ala Gly
            435                 440                 445

Thr Pro Tyr Leu Pro Ala Gly Leu Trp Leu Tyr Pro Leu Pro Thr Ala
450                 455                 460

Asp Asp Leu Arg Asp Ile Asn Val Glu Arg Lys Leu Asp Cys Ser Glu
465                 470                 475                 480

Asp Leu Lys Thr Lys Met Arg Val Ile Val Gln Leu Asn Leu Pro
                485                 490                 495

Lys Gly Ile Tyr Asn Pro Leu Lys Tyr Pro Asn Pro Ala Leu Gln Trp
            500                 505                 510

His Tyr Lys Ile Leu Gln Thr Leu Ala Leu Glu Glu Met Pro Glu
            515                 520                 525

Glu Pro Glu Asp Leu Thr Glu Pro Lys Asn Lys Ala Ile Ser Lys Arg
            530                 535                 540

Val Gly Gly Tyr Leu Glu Glu Trp Ser Glu Thr Leu Lys Asp Glu Ala
545                 550                 555                 560

Asp Arg Ala Thr Arg Ser Arg Ser Leu Lys Arg Glu Ile Glu Asp Asp
                565                 570                 575

Ala Pro Glu Arg Pro Ala Lys Gln Arg Lys Val Ala Gly Glu Arg Pro
            580                 585                 590

Ser Gly Ser Asn Leu Ser Met Ala Gln Leu Arg Asp Ala Ile Glu Ser
            595                 600                 605

Gly Ser Ile Ser Lys Met Thr Val Ala Gln Leu Lys Asp Val Ala Gly
            610                 615                 620
```

Ala Arg Gly Leu Ser Thr Gly Gly Lys Lys Ala Asp Leu Leu Glu Arg
625                 630                 635                 640

Ile Glu Gln Trp Val Glu Glu Asn Ser
                645

<210> SEQ ID NO 67
<211> LENGTH: 55
<212> TYPE: DNA
<213> ORGANISM: Trichoderma reesei

<400> SEQUENCE: 67
gtgtgcggcc gctcgagcat gcatgtttaa acagcttggc actggccgtc gtttt      55

<210> SEQ ID NO 68
<211> LENGTH: 55
<212> TYPE: DNA
<213> ORGANISM: Trichoderma reesei

<400> SEQUENCE: 68
atcagccccg agacggcgcc gcgtttaaac aattcgtaat catggtcata gctgt      55

<210> SEQ ID NO 69
<211> LENGTH: 55
<212> TYPE: DNA
<213> ORGANISM: Trichoderma reesei

<400> SEQUENCE: 69
catgattacg aattgtttaa acgcggcgcc gtctcggggc tgatcttgtc gagga      55

<210> SEQ ID NO 70
<211> LENGTH: 55
<212> TYPE: DNA
<213> ORGANISM: Trichoderma reesei

<400> SEQUENCE: 70
ggcggccgtt actagtggat ccagcccttg acagtgatct tgagtccagg tgcaa      55

<210> SEQ ID NO 71
<211> LENGTH: 58
<212> TYPE: DNA
<213> ORGANISM: Trichoderma reesei

<400> SEQUENCE: 71
tgcagatatc catcacactg gcggccgcag tttccatgtc caacgtgttg ttttgcgc    58

<210> SEQ ID NO 72
<211> LENGTH: 58
<212> TYPE: DNA
<213> ORGANISM: Trichoderma reesei

<400> SEQUENCE: 72
gccagtgcca agctgtttaa acatgcatgc tcgagcggcc gcacacgccc tctcctcg    58

<210> SEQ ID NO 73
<211> LENGTH: 20
<212> TYPE: DNA
<213> ORGANISM: Trichoderma reesei

<400> SEQUENCE: 73
caatgacgat ccgcacgcgt                                              20

```
<210> SEQ ID NO 74
<211> LENGTH: 20
<212> TYPE: DNA
<213> ORGANISM: Trichoderma reesei

<400> SEQUENCE: 74
caatgacgat ccgcacgcgt                                              20

<210> SEQ ID NO 75
<211> LENGTH: 20
<212> TYPE: DNA
<213> ORGANISM: Trichoderma reesei

<400> SEQUENCE: 75
gacactcttt tctcccatct                                              20

<210> SEQ ID NO 76
<211> LENGTH: 20
<212> TYPE: DNA
<213> ORGANISM: Trichoderma reesei

<400> SEQUENCE: 76
gaggagcaga agaagctccg                                              20

<210> SEQ ID NO 77
<211> LENGTH: 22
<212> TYPE: DNA
<213> ORGANISM: Trichoderma reesei

<400> SEQUENCE: 77
gcatatataa cccactcaag ta                                           22

<210> SEQ ID NO 78
<211> LENGTH: 22
<212> TYPE: DNA
<213> ORGANISM: Trichoderma reesei

<400> SEQUENCE: 78
attatcttgg accggccgca gg                                           22

<210> SEQ ID NO 79
<211> LENGTH: 37
<212> TYPE: DNA
<213> ORGANISM: Aspergillus fumigatus

<400> SEQUENCE: 79
actggattta ccatgacttt gtccaagatc acttcca                           37

<210> SEQ ID NO 80
<211> LENGTH: 40
<212> TYPE: DNA
<213> ORGANISM: Aspergillus fumigatus

<400> SEQUENCE: 80
tcacctctag ttaattaagc gttgaacagt gcaggaccag                        40

<210> SEQ ID NO 81
<211> LENGTH: 17
<212> TYPE: DNA
<213> ORGANISM: Aspergillus fumigatus

<400> SEQUENCE: 81
tgtcccttgt cgatgcg                                                 17
```

```
<210> SEQ ID NO 82
<211> LENGTH: 17
<212> TYPE: DNA
<213> ORGANISM: Aspergillus fumigatus

<400> SEQUENCE: 82
cacatgactt ggcttcc                                                        17

<210> SEQ ID NO 83
<211> LENGTH: 37
<212> TYPE: DNA
<213> ORGANISM: Aspergillus fumigatus

<400> SEQUENCE: 83
ggactgcgca ccatgactt gtccaagatc acttcca                                   37

<210> SEQ ID NO 84
<211> LENGTH: 38
<212> TYPE: DNA
<213> ORGANISM: Aspergillus fumigatus

<400> SEQUENCE: 84
gccacggagc ttaattaatt aagcgttgaa cagtgcag                                 38

<210> SEQ ID NO 85
<211> LENGTH: 37
<212> TYPE: DNA
<213> ORGANISM: Aspergillus fumigatus

<400> SEQUENCE: 85
cgcggtagtg gcgcggtcga ccgaatgtag gattgtt                                  37

<210> SEQ ID NO 86
<211> LENGTH: 36
<212> TYPE: DNA
<213> ORGANISM: Aspergillus fumigatus

<400> SEQUENCE: 86
ttaccaattg gcgcgccact accgcgttcg agaaga                                   36
```